US007439346B2

(12) United States Patent
Johnson et al.

(10) Patent No.: US 7,439,346 B2
(45) Date of Patent: *Oct. 21, 2008

(54) NUCLEIC ACIDS ARRAYS AND METHODS OF USE THEREFOR

(75) Inventors: Robert C. Johnson, Houston, TX (US); Mansoor Mohammed, Mission Viejo, CA (US); Jae Weon Kim, Houston, TX (US); Xan-Yan Lu, Sugarland, TX (US)

(73) Assignee: Perkinelmer Las Inc., Waltham, MA (US)

( * ) Notice: Subject to any disclaimer, the term of this patent is extended or adjusted under 35 U.S.C. 154(b) by 310 days.

This patent is subject to a terminal disclaimer.

(21) Appl. No.: 10/847,149

(22) Filed: May 17, 2004

(65) Prior Publication Data

US 2005/0059041 A1 Mar. 17, 2005

Related U.S. Application Data

(63) Continuation-in-part of application No. 10/273,399, filed on Oct. 15, 2002, now Pat. No. 7,335,470.

(60) Provisional application No. 60/471,216, filed on May 16, 2003, provisional application No. 60/329,030, filed on Oct. 12, 2001.

(51) Int. Cl.
*C07H 21/04* (2006.01)
*C12N 15/00* (2006.01)
*C12Q 1/68* (2006.01)

(52) U.S. Cl. .......................... 536/23.1; 536/24.3; 435/6

(58) Field of Classification Search .................. None
See application file for complete search history.

(56) References Cited

U.S. PATENT DOCUMENTS

| | | | |
|---|---|---|---|
| 4,337,063 A | 6/1982 | Mihara et al. | 436/536 |
| 4,355,153 A | 10/1982 | Radici et al. | 528/191 |
| 4,404,289 A | 9/1983 | Masuda et al. | 436/538 |
| 4,458,066 A | 7/1984 | Caruthers et al. | 536/25.34 |
| 4,652,613 A | 3/1987 | Collins et al. | 525/69 |
| 4,683,195 A | 7/1987 | Mullis et al. | 435/6 |
| 4,683,202 A | 7/1987 | Mullis et al. | 435/91.2 |
| 4,774,339 A | 9/1988 | Haugland et al. | 548/405 |
| 4,806,631 A | 2/1989 | Carrico et al. | 536/25.3 |
| 4,818,681 A | 4/1989 | Dattagupta | 435/6 |
| 4,826,789 A | 5/1989 | Jones et al. | 501/80 |
| 4,826,790 A | 5/1989 | Jones et al. | 501/90 |
| 4,937,188 A | 6/1990 | Giese et al. | 435/41 |
| 4,937,858 A | 6/1990 | Girscher et al. | 379/433.05 |
| 4,963,436 A | 10/1990 | Jones et al. | 428/403 |
| 5,008,220 A | 4/1991 | Brown et al. | 501/81 |
| 5,024,933 A | 6/1991 | Yang et al. | 435/6 |
| 5,047,519 A | 9/1991 | Hobbs et al. | 536/27.14 |
| 5,055,429 A | 10/1991 | James et al. | 501/80 |
| 5,068,269 A | 11/1991 | Diamantoglou | 524/35 |
| 5,135,717 A | 8/1992 | Renzoni et al. | 422/61 |
| 5,143,854 A | 9/1992 | Pirrung et al. | 436/518 |
| 5,151,507 A | 9/1992 | Hobbs et al. | 536/26.7 |
| 5,187,288 A | 2/1993 | Kang et al. | 548/110 |
| 5,188,934 A | 2/1993 | Menchen et al. | 435/6 |
| 5,190,864 A | 3/1993 | Giese et al. | 435/41 |
| 5,215,882 A | 6/1993 | Bahl et al. | 435/6 |
| 5,227,487 A | 7/1993 | Haugland et al. | 546/15 |
| 5,248,782 A | 9/1993 | Haugland et al. | 548/110 |
| 5,266,489 A | 11/1993 | Rey-Senelgonge et al. | 435/320.1 |
| 5,268,486 A | 12/1993 | Waggoner et al. | 548/427 |
| 5,274,113 A | 12/1993 | Kang et al. | 548/405 |
| 5,288,625 A | 2/1994 | Hadlaczky et al. | 435/449 |
| 5,288,641 A | 2/1994 | Roszman | 435/320.1 |
| 5,324,633 A | 6/1994 | Fodor et al. | 435/6 |
| 5,433,896 A | 7/1995 | Kang et al. | 252/700 |
| 5,434,049 A | 7/1995 | Okano et al. | 435/6 |
| 5,472,842 A | 12/1995 | Stokke et al. | 435/6 |
| 5,501,979 A | 3/1996 | Geller et al. | 435/320.1 |
| 5,514,785 A | 5/1996 | Van Ness et al. | 536/22.1 |
| 5,532,226 A | 7/1996 | Demarest et al. | 514/134 |
| 5,539,517 A | 7/1996 | Cabib et al. | 356/453 |
| 5,554,744 A | 9/1996 | Bhongle et al. | 536/25.3 |
| 5,556,752 A | 9/1996 | Lockhart et al. | 435/6 |
| 5,578,832 A | 11/1996 | Trulson et al. | 250/458.1 |
| 5,601,982 A | 2/1997 | Sargent et al. | 435/6 |

(Continued)

FOREIGN PATENT DOCUMENTS

| | | |
|---|---|---|
| WO | WO 96/17958 | 6/1996 |
| WO | WO 96/39154 | 12/1996 |
| WO | WO 97/03211 | 1/1997 |
| WO | WO 97/46313 | 12/1997 |
| WO | WO 99/09217 | 2/1999 |
| WO | WO 99/09218 | 2/1999 |
| WO | WO 99/13319 | 3/1999 |
| WO | WO 99/51773 | 10/1999 |
| WO | WO 99/60163 | 11/1999 |
| WO | WO 00/09650 | 2/2000 |
| WO | WO 00/26412 | 5/2000 |

(Continued)

OTHER PUBLICATIONS

Molecular Biology Reagents/Protocols 1992, United States Biochemical Corporation, 1991, Cleveland, Ohio, pp. 218-219.*

(Continued)

*Primary Examiner*—James Martinell
(74) *Attorney, Agent, or Firm*—Lowrie, Lando & Anastasi, LLP

(57) ABSTRACT

Compilations of nucleic acids, articles of manufacture which are surfaces comprising multiple blocks of arrays comprising such compilations, methods of use of the compilations and arrays for detection of chromosomal disorders, such as a chromosomal aneuploidies, deletions, amplifications, and diagnosis and prognosis of syndromes associated with a contiguous gene abnormality and kits are provided.

30 Claims, 31 Drawing Sheets

U.S. PATENT DOCUMENTS

| | | | |
|---|---|---|---|
| 5,610,287 A | 3/1997 | Nikiforov et al. | 536/24.3 |
| 5,614,386 A | 3/1997 | Metzker et al. | 435/91.1 |
| 5,630,932 A | 5/1997 | Lindsay et al. | 205/645 |
| 5,632,957 A | 5/1997 | Heller et al. | 422/68.1 |
| 5,635,351 A | 6/1997 | Feuerstein et al. | 435/6 |
| 5,637,687 A | 6/1997 | Wiggins | 536/25.4 |
| 5,641,630 A | 6/1997 | Snitman et al. | 435/6 |
| 5,652,099 A | 7/1997 | Conrad | 435/6 |
| 5,665,549 A | 9/1997 | Pinkel et al. | 435/6 |
| 5,684,148 A | 11/1997 | Caruthers et al. | 536/26.1 |
| 5,700,637 A | 12/1997 | Southern | 435/6 |
| 5,714,386 A | 2/1998 | Roederer | 436/546 |
| 5,721,098 A | 2/1998 | Pinkel et al. | 435/6 |
| 5,721,118 A | 2/1998 | Scheffler | 435/69.1 |
| 5,744,305 A | 4/1998 | Fodor et al. | 435/6 |
| 5,770,456 A | 6/1998 | Holmes | 435/518 |
| 5,776,745 A | 7/1998 | Ketner et al. | 435/477 |
| 5,790,727 A | 8/1998 | Dhadwal et al. | 385/38 |
| 5,795,557 A | 8/1998 | Pajonk et al. | 423/338 |
| 5,800,992 A | 9/1998 | Fodor et al. | 435/6 |
| 5,807,522 A | 9/1998 | Brown et al. | 422/50 |
| 5,830,645 A | 11/1998 | Pinkel et al. | 435/6 |
| 5,843,767 A | 12/1998 | Beattie | 435/287.1 |
| 5,846,708 A | 12/1998 | Hollis et al. | 435/6 |
| 5,856,097 A | 1/1999 | Pinkel et al. | 435/6 |
| 5,856,174 A | 1/1999 | Lipshutz et al. | 435/286.5 |
| 5,863,504 A | 1/1999 | Heffelfinger et al. | 422/82.08 |
| 5,874,259 A | 2/1999 | Szybalski | 435/91.1 |
| 5,880,473 A | 3/1999 | Ginestet | 250/458.1 |
| 5,922,617 A | 7/1999 | Wang et al. | 436/518 |
| 5,925,525 A | 7/1999 | Fodor et al. | 435/6 |
| 5,939,261 A | 8/1999 | Loewy et al. | 435/6 |
| 5,943,129 A | 8/1999 | Hoyt et al. | 356/318 |
| 5,959,098 A | 9/1999 | Goldberg et al. | 536/25.3 |
| 5,962,674 A | 10/1999 | Iyer et al. | 536/25.34 |
| 5,965,362 A | 10/1999 | Pinkel et al. | 435/6 |
| 5,965,452 A | 10/1999 | Kovacs | 436/149 |
| 5,976,790 A | 11/1999 | Pinkel et al. | 435/6 |
| 5,981,175 A | 11/1999 | Loring et al. | 435/6 |
| 6,001,982 A | 12/1999 | Ravikumar et al. | 536/22.1 |
| 6,013,440 A | 1/2000 | Lipshutz et al. | 435/6 |
| 6,022,963 A | 2/2000 | McGall et al. | 536/25.3 |
| 6,024,872 A | 2/2000 | Mahendran et al. | 210/500.25 |
| 6,025,155 A | 2/2000 | Hadlaczky et al. | 435/69.1 |
| 6,027,709 A | 2/2000 | Little et al. | 424/1.65 |
| 6,028,190 A | 2/2000 | Mathies et al. | 536/26.6 |
| 6,031,092 A | 2/2000 | Just et al. | 536/25.34 |
| 6,040,138 A | 3/2000 | Lockhart et al. | 435/6 |
| 6,045,996 A | 4/2000 | Cronin et al. | 435/6 |
| 6,048,457 A | 4/2000 | Kopaciewicz et al. | 210/321.6 |
| 6,048,695 A | 4/2000 | Bradley et al. | 435/6 |
| 6,048,982 A | 4/2000 | Waggoner | 548/148 |
| 6,049,380 A | 4/2000 | Goodwin et al. | 356/317 |
| 6,051,719 A | 4/2000 | Benson et al. | 548/416 |
| 6,054,270 A | 4/2000 | Southern | 435/6 |
| 6,054,279 A | 4/2000 | Nadeau et al. | 435/6 |
| 6,055,325 A | 4/2000 | Garini et al. | 382/129 |
| 6,060,324 A | 5/2000 | Naguib | 436/71 |
| 6,063,338 A | 5/2000 | Pham et al. | 422/61 |
| 6,066,459 A | 5/2000 | Garini et al. | 435/6 |
| 6,077,673 A | 6/2000 | Chenchik et al. | 435/6 |
| 6,096,817 A | 8/2000 | McNamara | 524/406 |
| 6,110,426 A * | 8/2000 | Shalon et al. | 422/68.1 |
| 6,140,044 A | 10/2000 | Besemer et al. | 435/6 |
| 6,143,495 A | 11/2000 | Lizardi et al. | 435/6 |
| 6,159,685 A | 12/2000 | Pinkel et al. | 435/6 |
| 6,183,957 B1 | 2/2001 | Cole et al. | 435/6 |
| 6,191,425 B1 | 2/2001 | Imai | 250/458.1 |
| 6,197,501 B1 | 3/2001 | Cremer et al. | 435/6 |
| 6,197,506 B1 | 3/2001 | Fodor et al. | 435/6 |
| 6,235,504 B1 | 5/2001 | Zhang et al. | 435/91.2 |
| 6,251,601 B1 | 6/2001 | Bao et al. | 435/6 |
| 6,252,664 B1 | 6/2001 | Barbera-Guillem | 356/417 |
| 6,258,606 B1 | 7/2001 | Kovacs | 436/149 |
| 6,261,776 B1 | 7/2001 | Pirrung et al. | 435/6 |
| 6,268,132 B1 | 7/2001 | Conrad | 435/6 |
| 6,277,489 B1 | 8/2001 | Abbott et al. | 428/403 |
| 6,277,581 B1 | 8/2001 | O'Brien et al. | 435/6 |
| 6,277,621 B1 | 8/2001 | Horsburgh et al. | 435/235.1 |
| 6,277,628 B1 | 8/2001 | Johann et al. | 435/287.2 |
| 6,294,331 B1 | 9/2001 | Ried et al. | 435/6 |
| 6,294,338 B1 | 9/2001 | Nunomura | 435/6 |
| 6,309,822 B1 | 10/2001 | Fodor et al. | 435/6 |
| 6,344,316 B1 | 2/2002 | Lockhart et al. | 435/6 |
| 6,403,320 B1 | 6/2002 | Read et al. | 435/6 |
| 2001/0012537 A1 | 8/2001 | Anderson et al. | 428/357 |
| 2001/0014448 A1 | 8/2001 | Chappa et al. | 435/6 |
| 2001/0014449 A1 | 8/2001 | Nerenberg et al. | 435/6 |
| 2001/0016322 A1 | 8/2001 | Caren et al. | 435/6 |
| 2001/0018514 A1 | 8/2001 | McGall et al. | 536/26.6 |
| 2001/0018642 A1 | 8/2001 | Balaban et al. | 702/19 |
| 2001/0019827 A1 | 9/2001 | Dawson et al. | 435/6 |

FOREIGN PATENT DOCUMENTS

| | | |
|---|---|---|
| WO | WO 00/42222 | 7/2000 |
| WO | WO 00/47600 | 8/2000 |
| WO | WO 01/01144 | 1/2001 |
| WO | WO 03/091426 | 11/2003 |
| WO | 0233044 A2 | 4/2005 |

OTHER PUBLICATIONS

Kern et al., "Direct Hybridization of Large-Insert Genomic Clones on High-Density Gridded cDNA Filter Arrays," *Bio Techniques*, 23:120-124, Jul. 1997.

Rice et al., "Comparative Genomic Hybridization in Pediatric Acute Lymphoblastic Leukemia," *Pediatric Hematology and Oncology*, 17:141-147, 2000.

Houldsworth et al., "Comparative Genomic Hybridization: An Overview," *Amer. Journal of Pathology*, vol. 145, No. 6, Dec. 1994.

Wa'el Fi-Rital et al., "High-Resolution Deletion Mapping of Chromosome 14 in Stromal Tumors of the Gastrointestinal 14 in Stromal Tumors of the Gastrointestinal Tract Suggests Two Distinct Tumor Suppressor Loci," *Genes, Chromosomes & Cancer*, 27: 387-391, 2000.

Stewart D.J., "Making and Using DNA Microarrays: A Short Course at Cold Spring Harbor Laboratory," *Genome Research*, vol. 10 (1), 1-3. www. genome.org.

Suzuki et al., "Construction and evaluation of a porcine bacterial artificial chromosome library," *Anim. Genet.*, 31(1) 8, (Feb. 2000).

Zhao et al., "High-density cDMA filter analysis: a novel approach for large-scale, quantitative analysis of gene expression," *Gene*, 156(2): 207, Apr. 24, 1995.

DeRisi et al., "Genomics and array technology," *Current Opinion Oncology*, 11(1) Jan. 1999.

Issa, J.P., "CpG-Island Methylation in Aging and Cancer," *Curr. Top Microbiol. Immunol.*, 249:101-118, 2000.

Pfeifer et al., "Mutation Hotspots and DNA Methylation," *Curr. Top Microbiol. Immunol.*, 249:1-19. 2000.

Pogribny et al., "A Sensitive New Method for Rapid Detection of Abnormal Methylation Patterns in Global DNA and winin CpG Islands," *Biochemical and Biophysical Res. Communications*, 262:624-628, 1999.

Oakeley E.J., "DNA methylation analysis: a review of current methodolgies," *Pharmacology & Therapeutics*, vol. 84, No. 3: 389-400, Dec. 1999.

Robertson et al., "DNA methylation: past, present and future directions," *Carcinogenesis*, vol. 21, No. 3:461-467, Mar. 2000.

Fan et al., "Parallel Genotyping of Human SNP's Using Generic High-density Oligonucleotide Tag Arrays," *Research*, vol. 10, No. 6:853-860, Jun. 2000.

Sapolsky et al., "High-throughput polymorphism screening and genotyping with high-density oligonucleotide arrays," *Genetic Analysis Biomolecular Engineering*, vol. 14., Nos. 5-6:187-192, Feb. 1999.

Emerson et al., "LXIII Cold Spring Harbor Symposium on Quantitative Biology: Mechanisms of Transcription," *Biochemica et Biophysica Acta* 1423: R45-R51, 1998.

DeRisi et al., "Use of a cDNA microarray to analyze gene expression patterns in human cancer," *Nature Genetics*, 14:457-460, 1996.

Schena et al., "Parallel human genome analysis: Microarray-based expression monitoring of 1000 genes," *Proc. Nat'l Acad. Sci.*, vol. 93:10614-10619, Oct. 1996.

Schena et al., "Quantitative Monitoring of Gene Expression Patterns with a Complementary DNA Microarray," *Science*, vol. 270:467-470, Oct. 20, 1995.

Shalon et al., A DNA Microarray System for Analyzing Complex DNA Samples Using Two-color Fluorescent Probe Hybridization,: *Genome Research*, 6:639-645, 1996.

Maskos et al., Oligonucleotide hybridizations on glass supports: a novel linker for oligonucleotide synthesis and hybridization properties of oligonucleotides synthesized in situ, *Nucleic Acids Research*, vol. 20, No. 7:1679-1684, Mar. 1992.

Hacia et al, "Detection of heterozygous mutations in BGRCA1 using high density oligonucleotide arrays and two -colour fluorescence analysis," *Nature Genetics*, vol. 14: 441-447, Dec. 1996.

Lockhart et al., "Expression monitoring by hybridization to high-density oligonucleotide arrays," *Nature Biology*, vol. 14: 1675-1680, Dec. 1996.

Guo et al., "Direct fluorescence analysis of genetic polymorphisms by hybridization with oligonucleotide arrays on glass supports," *Nucleic Acids Res.*, vol. 22, No. 24:5456-5465, 1994.

Ramsay, Graham, "DNA chips: State-of-the-Art," *Nature Biotechnology*, vol. 16: 40-44, Jan. 1998.

Marshall et al., "DNA chips: An array of possibilities," *Nature Biotechnology*, vol. 16: 27-31, Jan. 1998.

Castellino Alexander M.., "When the Chips are Down," *Genome Research*, vol. 7:943-946, 1997.

Schena, Mark, "Genome analysis with gene expression microarrays," *BioEssays*, vol. 18, No. 5:427-431, Jan. 1996.

Beattie et al., "Hybridization of DNA Targets to Glass-Tethered Oligonucleotide Probes," *Molecular Biotechnology*, vol. 4:213-225, 1995.

Anderson et al, "Quantitative Fiber Hybridization," *Nucleic and hybridization a practical approach*IRL Press, pp. 98-99, 1985.

Eisen et al., Methods Enzymol, 303: 179, 1999.

Chen, *J. Biochem. Biophys. Methods*, 42:147-151, 2000.

Samstag, *Antisense Nucleic Acid Drug Dev.*, 6:153-156, 1996.

Milligan, *J. Med Chem.*, 36:1923-1937, 1993.

Strauss-Soukup, *Biochemistry*, 36:8692-8698, 1997.

Mata, *Toxicol. Appl. Pharmacol.*, 144:189-197, 1997.

Carruthers, Cold Spring Harbor Symp. Quant. Biol., 47:411-418, 1982.

Adams, *J. Am. Chem. Soc.*, 105: 661 (1983).

Frenkel, *Free Radic. Biol. Med.* 19:373-380, 1995.

Blommers, *Biochemistry*, 33:7886-7896, 1994.

Narang, *Meth. Enzymol.*, 68:90, 1979.

Brown, *Meth. Enzymol.*, 68:109, 1979.

Beaucage, *Trtra. Lett.* 22:1859, 1981.

Ascenzioni, *Cancer Lett.* 118:135-142, 1997.

Kuroiwa, *Nat. Biotechnol.* 18:1086-1090, 2000.

Mejia, *Am. J. Hum. Genet.*, 69:315-326, 2001.

Warburton, *Nature*, 386:553-555, 1997.

Roush, *Science*, 276:38-39, 1997.

Rosenfeld, *Nat. Genet.* 15:333-335, 1997.

Csonka, *J. Cell Sci.*, 113 (Pt. 18):3207-3216, 2000.

Feingold, *Proc. Nat'l. Acad.Sci. USA*, 87:8637-8641, 1990.

Tucker, *Gene*, 199:25-30, 1997.

Adam, *Plant J.*, 11:1349-1358, 1997.

Zeschnigk, *Nucleic Acids Res.*, 27:21, 1999.

Asakawa, *Gene*, 69-79, 1997.

Cao, *Genome Res.* 9:763-774, 1999.

Boren, *Genome Res.* 6:1123-1130, 1996.

Ioannou, *Nature Genet.* 6:84-89, 1994.

Mejia, *Genome Res.*, 7:179-186, 1997.

Ashworth, *Analytical Biochem.* 224:564-571, 1995.

Wu, *Genomics*, 4:560, 1989.

Barringer, *Gene*, 89:117, 1990.

Kwoh, *Proc. Nat;l Acad. Sci.*, USA, 86:1173, 1989.

Guatelli, *Proc. Nat;l Acad. Sci.*, USA, 87:1874, 1990.

Smith, *J. Clin. Microbiol.* 35:1477-1491, 1997.

Burg, *Mol. Cell. Probes*, 10:257-271, 1996.

Birch, *Lett. Appl. Microbiol.* 33:296-301, 2001.

Greijer, *J. Virol. Methods*, 96:133-147, 2001.

Kimmel et al, Methods Enzymol. 152:307-316 (1987).

Herrera, J. Mol. Biol., 236:405-411, 1994.

Suck, J. Mol. Recognit. 7:65-70, 1994.

Fitzgerald, *Nucleic Acids Res.*, 20:3753-3762, 1992.

Deininger, *Anal. Biochem.*, 129:216-223, 1983.

Ordahl, *Nucleic Acids Res.*, 3:2985-2999, 1976.

Siles, *J. Chromatogr. A.*, 771:319-329, 1997.

Chiu, *Nucleic Acids Res.*, 28:E31, 2000.

Ichikawa, *Asian J. Androl.* 2(3): 167-171, 2000.

Cui et al., *Cancer Genet. Cytolgenet*, 107:51, 1998.

Matsuyama et al., *Aktuel Urol.* 34:247, 2003.

Matsuyama et al., *Prostrate*, 54,103, 2003.

Eugster, *Amer. J. Med. Genet.*, 40(4):409-412, 1997.

Reish, *Amer. J. Med. Genet.*, 59(4):467-475, 1995.

Smeets, *Genet. Couns.* 12(1):85-89, 2001.

Battaglia, *Adv. Pediatr.*, 48:75-113, 2001.

Marcelis, *Genet. Couns,*. 12:35-48, 2001.

Kant, *J. Med. Genet.*, 34(7):569-572, 1997.

Pollin, *Amer. J. Med. Genet.*, 85(4):369-375, 1999.

Hilton, *Genomics*, 71(2):192-199, 2001.

Nardmann, *Hum. Genet.*, 99(5):638-643, 1997.

George, *J. Eur. Acad. Dermatol. Venereol.* 11(1):66-68, 1998.

Naselli, *Pediatr. Radio.* 28(11):851-855, 1998.

Chilosi, *Amer. J. Med. Genet.*, 100(2):138-144, 2001.

Kobayashi, *J. Craniomaxillofac. Sugy.*, 28(3):165-170, 2000.

Epstein, *Trends Genet*.17(10):S13-17, 2001.

Crolla, *J. Med. Genet.* 34(3):207-212, 1997.

Ariel, *Pediatr. Pathol. Lab. Med.* 16(6):1013-1021, 1996.

Li, *Genomics*, 74(3):370-376, 2001.

Torrisi, *Am. J. Med. Genet.*, 106(2):125-128, 2001.

Baumer, *Hum. Genet*, 105(6):598-602, 1999.

Greger, *Am. J. Hum. Genet*, 60(3):574-580, 1997.

Manni, *Clin. Neurophysiol.*, 112(5):800-805, 2001.

Vilella, *Arch. Dis. Child.* 83(4):360-361, 2000.

Mersiyanova, *Hum. Mutat.* 15(4):340-347, 2000.

Chance, *Phys. Med. Rehabil. Clin N. Am.* 12(2):277-291, 2001.

Lane, *J. Hand Surg.* [Am] 26(4):670-674, 2001.

King, *Acta Neuropathol* (Berl) 99(4):425-427, 2000.

Honda *Brain Dev*. 20(3):190-192, 1998.

Juyal, *Am. J. Hum. Genet.* 58(5):998-1007, 1996.

Thomas, *Fetal Diagn. Ther.* 15(6):335-337, 2000.

DeLeersnyder, *J. Pediatr.* 139(1):111-116, 2001.

Yuan, *Acta Paediatr.* Jpn 39(6):647-652, 1997.

Hol, *Hum. Genet.* 95(6):687-690, 1995.

Smith, *Am. J. Med. Genet.* 81(2): 186-191, 1998.

Fokstuen, *Eur. J. Pediatr.* 160(1):54-57, 2001.

Cole, *Clin. Chem.* 40(11 Pt. 1):2099-2103, 1994.

Grain, *Neuromuscul. Disord.* 11(2):186-191, 2001.

Crilley, *J. Am. Coll. Cardio.* 36(6): 1953-1958, 2000.

Sjarif, *J. Inherit. Metab. Dis.* 23(6):529-547, 2000.

Scheuerle, *J. Pediatr.* 126(5 Pt 1):764-767, 1995.

Weissortel, *Clin. Genet.* 54(1):45-51, 1998.

Santolaya-Forgas, *Fetal Diagn. Ther.* 12(1):36-39, 1997.

Damiani, *J. Pediatr Endocrinol. Metab.* 12(6):827-831, 1999.

Kadandale, *Microb. Comp. Genomics* 5(2):71-74, 2000.

Yu, *Nat. Genet.* 20(4):353-357, 1998.

Vasquez, *Genet. Couns.* 10(3):301-304, 1999.

Maya-Nunez, *Clin. Endocrinol.* (Oxf) 50(2):157-162, 1999.

Zappia, *J. Otolaryngol.* 21(1):16-19, 1992.

Guerrini, *Epilepsia* 42 Suppl 3:36-41, 2001.

Shanske, *Am. J. Med. Genet.* 102(3):231-236, 2001.

Rickard, *Hum. Genet.* 108(5):398-403, 2001.

DiCicco, *Int. J. Pediatr. Otohinolaryngol* 59(2):147-150, 2001.

Moore, *Eur. J. Hum. Genet.* 8:223-228, 2000.
Djalali, *Prenat. Diagn.* 20:934-935, 2000.
Harrison, *Hum. Genet.* 92:353-358, 1993.
Fung, *J. Histochem. Cytochem.* 49:797-798, 2001.
Sanz, *Fetal Diagn. Ther.* 16:95-97, 2001.
Ibanez, *Mol. Reprod. Dev.* 58:166-172, 2001.
Theillet, *Bull. Cancer* 88:261-268, 2001.
Werner, *Pharmacogenomis* 2:25-36,2001.
Jain, *Pharmacogenomics* 1:289-307, 2000.
Johnston, *Curr.. Biol.* 8:R171-R174, 1998.
Schummer, *Biotechniques*, 23:1087-1092, 1997.
Mansfield, *Mol. Cell Probes* 9:145-156, 1995.
Jameson, *Methods Enzymol.* 278:363-390, 1997.
Pollack, *Nature Genetics*, 23:41-46, 1999.
Kaboev, Nucleic Acids Res., 28:e94 (2000).
Smirnov, Biochemistry, 39:1462-1468, 2000.
Kim et al., "Putative Chromosomal Deletions on 9P, 9Q and 22Q Occur Preferentially in L=Malignant Gastrointestinal Stromal Tumors," Int J. Cancer, 85:633-638, 2000.
Bertucci et al., "Sensitivity issues in DNA array-based expression measurements and performance of nylon microarrays for small samples," Human Mol. Genet., 8(9): 1715, Sep. 1999.
Yan et al., "CpG Island Arrays: An Application toward Deciphering Epigenetic Signatures of Breast Cancer," Clinical Cancer Research, vol. 6, No. 4, pp. 1432-1438, Apr. 2000.
Huang et al., Methylation profiling of CpG islands in human breast cancer cells, Human Molecular Genetics, vol. 8, No. 3m 459-470, 1999.
Cross et al., "CpG island libraries from human Chromosomes 18 and 22: landmarks for novel genes," Mammalian Genome, vol. 11, No. 5, May 2000, pp. 373-383.
Eads et al., MethyLight: a high-throughput assay to measure DNA methylation,: Nucleic Acids Res., vol. 28, No. 8, E32-00, 2000.
Chen, J. Org. Chem., 65:2900-2906, 2000.
Belousov, Nucleic Acids Res. 25:3440-3444, 1997.
Woon, Genomics, 50:306-316, 1998.
Reid, Genomics, 43:366-375, 1997.
Nothwang, Genomics, 41:370-378, 1997.
Baker, Nucleic Acids Res. 25:1950-1956, 1997.
Landegren, Science, 241:1077, 1988.
Berger, Methods Enzymol, 152:307-316, 1987.
Thorstenson, Genome Res., 8:848-855, 1998.
Oefner, Nucleic Acids Res., 24:3879-3886, 1996.

Goldberg, Am. J. Hum. Genet. 67(2): 417-431, 2000.
Barghorn, J. Pathol. 194(4):451-458, 2001.
Maitra, Am. J. Pathol., 159(1):119-130, 2001.
McGaughran, Am. J. Med. Genet. 94(4):311-315, 2000.
Zollino, Amer. J. Med. Genet., 82(5):371-375, 1999.
Mainardi, J. Med. Genet., 38(3):151-158, 2001.
VanBugenhout, Amer. J. Med. Genet., 90(3):203-215, 2000.
Mutchinick, Amer. J. Med. Genet., 85(2):99-104, 1999.
Donnai, Amer. J. Med. Genet., 91:157-158, 2000.
Wouters. Amer. J. Med. Genet., 102:(3):261-265, 2001.
Dasouki, Amer. J. Med. Genet., 73(1):72-75, 1997.
Lichtner, J. Med. Genet., 37(1):33-37, 2000.
Horike, Hum. Mol. Genet. 9(14):2075-2083, 2000.
Wu, Am. J. Hum. Genet. 67(5):1327-1332, 2000.
Petrij, J. Med. Genet, 37(3):168-176, 2000.
Badano, Clin. Chem. 47(5):838-843, 2001.
Potocki, Nat. Genet. 24(1):84-87, 2000.
Natacci, Am. J. Hum. Genet. 66:100-109.
DeLeersnyder, J. Med. Genet. 38(9):586-590, 2001.
Eliez, Am. J. Psychiatry 158(3):447-453, 2001.
Duke, Arch. Otolaryngol. Head Neck Surg. 126(9):1141-1145, 2000.
Peter, J. Clin. Endocrinol. Metab. 83(8):2666-2674, 1998.
Hobson, Hum. Mutat. 17(2):152, 2001.
Hodes, Am. J. Hum. Genet. 67(1):14-22, 2000.
Valdes-Flores, Am. J. Med. Genet. 102(2) 146-148, 2001.
Kadandale, Am. J. Hum. Genet. 95(1):71-74, 2000.
Schmidt, et al, Am. J. Hum. Genet. 69 (4), 876-882, 2001.
Khoo, Oncogene 20(37):5239-5242, 2001.
Spranger, Am. J. Med. Genet 83(5):367-371, 1999.
Jalal, Mayo Clin. Proc. 72:705-710, 1997.
Solinas-Toldo, Genes, Chromosomes & Cancer 20:399-407, 1997.
Bowtell, Nature Genetics Supp. 21:25-32, 1999.
Zhu, Nucleic Acids Res., 22:3418-3422, 1994.
Bartosiewicz, Archives of Biochem. Biophysics 376:66-73, 2000.
Schena, Proc. Nat;l Acad. Sci., USA, 93:10614-10619, 1996.
Pinkel, Nature Genetics, 20:207-211, 1998.
Henegariu, Nat. Biotechnol., 18:345-349, 2000.
Sokol, Proc. Nat'l. Acad. Sci. USA, 95:11538-11543, 1998.
Antony, Biochemistry, 40:9387-9395, 2001.
Hamaguchi, Anal. Biochem., 294:126-131, 2001.
Poddar, Mol Cell. Probes, 15:161-167, 2001.
Yamamoto, Nucleic Acids Res., 5:389-396, 2000.

* cited by examiner

CHROMOSOME 5

NUMBER OF CLONES: 15 CLONES + 7 pter *
p15.33 ***
p15 * Cri-du-Chat

| Clone ID | Cyto | Linear (Mb) | Disorder |
|---|---|---|---|
| GS-189N21 | 5pter | 0 | |
| RP11-811I15 | 5p15.33 | 0.1 | |
| 84C11 | 5p15 | 0.4 | Cri-du-Chat |
| RP11-94J21 | 5p15.33 | 1.4 | |
| RP11-121L11 | 5p15.33 | 3.5 | |
| RP11-91M12 | 5p15.2 | 9.9 | ← |
| RP11-91L13 | 5p14 | 24.4 | ← |
| RP11-67N10 | 5p13 | 35.9 | ← |
| RP11-91C10 | 5q12 | 67.3 | ← |
| RP11-90M19 | 5q15-5q21 | 98 | ← |
| RP11-81L23 | 5q23.3 | 128.9 | ← |
| RP11-31B18 | 5q33.2 | 155.7 | ← |
| RP11-88L12 | 5q35.2 | 172.6 | |
| RP11-125L2 | 5q35.2 | 173.5 | |
| CTC-355H1 | 5q35 | 175.2 | Sotos Syndrome + C92s |
| RP11-1006E8 | 5q35 | 175.9 | |
| RP11-606E24 | 5q35 | 176.3 | |
| RP1-118M12 | 5q35 | 176.6 | |
| RP11-933K12 | 5q35 | 176.8 | |
| RP11-158F10 | 5q35 | 177.7 | |
| RP11-2I16 | 5q35.2 | 177.8 | |
| GS-240G13 | 5qter | 181 | | q35 ****** Sotos Syndrome + C92s
q35.2 ***
qter *

CHROMOSOME 6

NUMBER OF CLONES: 10 CLONES + 4 pter *
p25.3 ***
p22.3 **

| Clone ID | Cyto | Linear (Mb) | Disorder |
|---|---|---|---|
| RP5-856G1 | 6pter | 1 | |
| RP11-42D22 | 6p25.3 | 1.5 | |
| RP11-82M9 | 6p25.3 | 1.8 | |
| RP11-299J5 | 6p25.3 | 2.5 | |
| RP1-239K6 | 6p22.3 | 19.1 | |
| 125B1 | 6p | 20 | |
| RP3-357H1 | 6p12.1-6p12.3 | 51.8 | ← |
| RP11-79L15 | 6q14 | 78.6 | ← |
| RP11-80B14 | 6q22 | 123.8 | ← |
| RP3-468K18 | 6q24.1-6q24.3 | 144.1 | ← |
| RP11-91O16 | 6q27 | 167.5 | |
| RP3-366N23 | 6q27 | 167.6 | |
| RP3-495K2 | 6q27 | 169.1 | |
| RP1-191N21 | 6qter | 170.7 | | q27 ***
qter *

CHROMOSOME 9

NUMBER OF CLONES: 8 CLONES + 5 (chr9 mosaicism)

| Clone ID | Cyto | Linear (Mb) | Disorder |
|---|---|---|---|
| GS-43N6 | 9pter | 0.6 | |
| RP11-31F19 | 9p24.3 | 0.6 | |
| RP11-459D20 | 9p24.3 | 1.2 | |
| RP11-48M17 | 9p24.3 | 2.2 | |
| RP11-399M15 | 9p21.2-9p22.1 | 18.6 | ← |
| RP11-327L3 | 9p13.1-9p13.3 | 35.9 | ← |
| RP11-89K20 | 9q13 | 67.1 | ← |
| RP11-80J10 | 9q22 | 86.8 | ← |
| RP11-451E16 | 9q33 | 114.6 | ← |
| RP11-432J22 | 9q34.3 | 134.3 | |
| RP11-216L13 | 9q34.3 | 135 | |
| RP11-424E7 | 9q34.3 | 136.2 | |
| GS-112N13 | 9qter | 136.3 | |

CHROMOSOME 12

NUMBER OF CLONES: 9 CLONES + 4

| Clone ID | Cyto | Linear (Mb) | Disorder |
|---|---|---|---|
| GS-496A11 | 12pter | 0 | |
| RP11-598F7 | 12p13.33 | 0.1 | |
| RP11-359B12 | 12p13.33 | 0.9 | |
| RP11-440E12 | 12p13.33 | 1 | |
| RP11-407G6 | 12p12.32 | 2.5 | |
| RP11-434C1 | 12p13.1-12p13.2 | 11.6 | ← |
| RP11-681G7 | 12q13.2 | 54.6 | ← |
| RP11-79B17 | 12q21.3 | 87.3 | ← |
| RP11-90F3 | 12q24.2 | 112.4 | ← |
| RP11-669N7 | 12q24.33 | 127.9 | |
| RP11-117L5 | 12q24.33 | 129.3 | |
| RP11-897M7 | 12q24.33 | 130.3 | |
| GS-221K18 | 12qter | 132 | |

CHROMOSOME 15

NUMBER OF CLONES: 15 CLONES + 3 q11.2 ******  Prader-Willi Syndrome (PWS) / Angelman Region (AR)

q14 **** q34 ***
qter *

| Clone ID | Cyto | Linear (Mb) | Disorder |
|---|---|---|---|
| RP11-289D12 | 15q11.2 | 20.4 | Prader-Willi Syndrome (PWS) / Angelman Region (AR) |
| RP11-26F2 | 15q11.2 | 20.6 | |
| 14I12 | 15q11.2 | 21 | |
| 398C20 | 15q11.2 | 22 | |
| 5E9 | 15q11.2 | 23 | |
| RP11-231D12 | 15q11.2 | 31.1 | |
| RP11-602M11 | 15q14 | 32.3 | |
| RP11-122P18 | 15q14 | 32.3 | |
| RP11-64O3 | 15q14 | 32.7 | |
| RP11-814P5 | 15q11.2 | 32.7 | Prader-Willi Syndrome (PWS) / Angelman Region (AR) |
| RP11-323I15 | 15q14 | 33.1 | |
| RP11-390M11 | 15q21.3 | 52 | ← |
| RP11-101C13 | 15q22 | 67.6 | ← |
| RP11-79A7 | 15q26.1 | 90.4 | ← |
| RP11-397C10 | 15q34 | 97.2 | |
| RP11-90E5 | 15q34 | 98.4 | |
| RP11-168G16 | 15q34 | 98.6 | |
| RP11-341B7 | 15qter | 99 | |

CHROMOSOME 16

NUMBER OF CLONES: 14 CLONES + 5

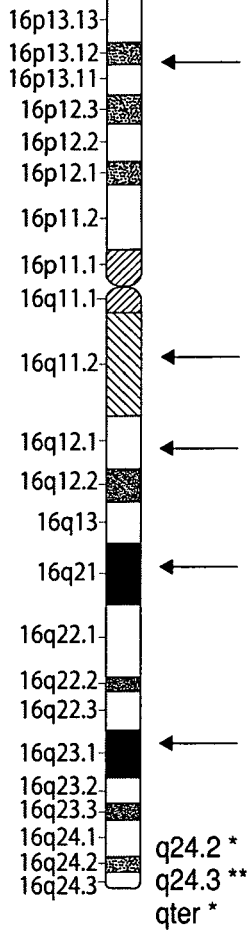

pter *
p13.3 ** Tuberous sclerosis-2 (TSC2) / Polycystic kidney disease,
p13.3 *** adult type I (PKD1)
p13.3 **** Rubinstein - Taybi Syndrome (RTS)

q24.2 *
q24.3 **
qter *

| Clone ID | Cyto | Linear (Mb) | Disorder |
|---|---|---|---|
| GS-12I4 | 16pter | 0.2 | |
| RP11-568F1 | 16p13.3 | 0.5 | |
| RP11-616M22 | 16p13.3 | 1.2 | |
| RP11-157H9 | 16p13.3 | 1.8 | Tuberous sclerosis-2 (TSC2) / Polycystic kidney disease, adult type I (PKD1) |
| CTD-2517G10 | 16p13.3 | 2 | |
| RP11-657D15 | 16p13.3 | 2.2 | |
| RP11-461A8 | 16p13.3 | 3.7 | Rubinstein - Taybi Syndrome (RTS) |
| RT100 | 16p13.3 | 3.8 | |
| RP11-75P12 | 16p13.3 | 3.8 | |
| RP11-95J11 | 16p13.3 | 3.9 | |
| RP11-81F1 | 16p13.1 | 11.4 | ← |
| RP11-474B12 | 16q11.2-16q12.1 | 47.1 | ← |
| RP11-79E10 | 16q12.1 | 52.4 | ← |
| RP11-89G14 | 16q21 | 61.2 | ← |
| RP11-91O9 | 16q23 | 77.9 | ← |
| RP11-106D4 | 16q24.2 | 87.2 | |
| RP11-21B21 | 16q24.3 | 88.3 | |
| RP11-566K11 | 16q24.3 | 89.7 | |
| GS-240G10 | 16qter | 90 | |

Fig. 16

CHROMOSOME 18

NUMBER OF CLONES: 14 CLONES + 1 (Chr18 Trisomies)

| Clone ID | Cyto | Linear (Mb) | Disorder |
|---|---|---|---|
| GS-52M11 | 18pter | 0.1 | |
| RP11-78H1 | 18p11.3 | 2.2 | |
| RP11-55N14 | 18p11.3 | 2.8 | |
| RP11-106O1 | 18p11.3 | 3.6 | |
| RP11-105C15 | 18p11.3 | 5.9 | |
| RP11-151D11 | 18p11.2 | 13.1 | |
| RP11-411B10 | 18p11.2 | 14 | |
| RP11-90G7 | 18q11.2 | 26.1 | ← |
| RP11-63N12 | 18q12 | 30.9 | |
| RP11-160B24 | 18q21 | 51.9 | |
| RP11-49H23 | 18q22 | 64.9 | |
| RP11-90L3 | 18q23 | 73.5 | |
| RP11-91C19 | 18q23 | 75 | |
| RP11-89N1 | 18q23 | 75.9 | |
| GS-964M9 | 18qter | 77 | |

CHROMOSOME 19

NUMBER OF CLONES: 5 CLONES + 2

| Clone ID | Cyto | Linear (Mb) | Disorder |
|---|---|---|---|
| RP13-609M15 | 19p13.3 | 0.3 | |
| RP11-75H6 | 19pter | 1 | |
| RP11-554A7 | 19p13.3 | 3.2 | |
| RP11-56K21 | 19p13.12 | 14.4 | ← |
| RP11-91H20 | 19q13.1 | 43.1 | ← |
| RP11-1129C9 | 19q13.4 | 59.3 | |
| RP11-45K21 | 19q13.43 | 61.1 | |

CHROMOSOME 21

NUMBER OF CLONES: 7 CLONES + 1 (Chr21 Trisomies)

| Clone ID | Cyto | Linear (Mb) | Disorder |
|---|---|---|---|
| RP11-89M24 | 21q21 | 15.7 | ← |
| RP11-143A3 | 21q21 | 18.2 | |
| RP11-108H5 | 21q21 | 26.8 | |
| RP11-17O20 | 21q22.1 - 22.2 | 35.3 | DownSyndrome CriticalRegion Gene 1 (DSCR1) |
| RP11-88N2 | 21q22.3 | 43.7 | |
| RP11-190A24 | 21q22.3 | 44.1 | |
| RP11-640F21 | 21q22.3 | 46.2 | |
| GS-63H24 | 21qter | 46.9 | | q21 ** q22.1 * Down Syndrome Critical Region Gene 1 (DSCR1)

q22.3 ***
qter

Chromosome X

Number of clones : 59 clones +3 clones

| Clone ID | Cyto | Linear (Mb) | Disorder |
|---|---|---|---|
| GS-98C4 | X pter | 0.5 | |
| RP11-28P6 | Xp22.33 | 1.3 | |
| RP11-483M24 | Xp22.32 | 6.4 | |
| GS1-227L7 | Xp22.32 | 6.6 | Placental steroid sulfatase deficiency (STS) |
| RP11-143E20 | Xp22.3 | 7.1 | |
| RP11-589J20 | Xp22.32 | 7.7 | |
| RP11-606J16 | Xp22.32 | 8 | Kallmann Syndrome (KAL) |
| 8D11 | Xp22.31 | 8.2 | |
| 55C5 | Xp22.31 | 8.4 | |
| 239F12 | Xp22.31 | 8.6 | |
| 232B2 | Xp22.22 | 10.2 | |
| RP1-27C22 | Xp22.31 | 10.3 | |
| RP1-39D12 | Xp22.31 | 10.3 | MLS Syndrome Deletion |
| RP1-134G1 | Xp22.31 | 10.3 | |
| RP1-185L21 | Xp22.31 | 10.3 | |
| CTC-285I15 | Xp22.31 | 10.3 | |
| GS1-602M16 | Xp22.31 | 10.5 | |
| GS1-590J6 | Xp22.31 | 11.1 | |
| RP11-79B3 | Xp22.1 | 23.7 | |
| RP4-540A13 | Xp21 | 24.5 | |
| AD8E10 | Xp21 | 25 | |
| 36E6 | Xp21 | 26 | |
| 222F5 | Xp21 | 27 | |
| RP11-487M22 | Xp21.3 | 27.9 | Glycerol kinase deficiency (GK) |
| RP6-27C10 | Xp21.3 | 28.5 | |
| RP11-89L23 | Xp21.3 | 30 | Glycerol kinase deficiency (GK) / Adrenal hypoplasia, congenital (AHC) |
| GS1-484O17 | Xp21.3 | 30 | |
| RP11-242C19 | Xp21.3 | 30.1 | |
| RP11-480I16 | Xp21.3 | 30.3 | |
| RP11-46A23 | Xp21.3 | 30.5 | |
| RP11-338L12 | Xp21.2 | 30.7 | |
| RP11-122N14 | Xp21.2 | 30.9 | |
| RP11-124H12 | Xp21.3 | 31.2 | |
| RP11-377J16 | Xp21.3 | 31.2 | |
| RP11-509C1 | Xp21.3 | 31.4 | Duchenne Muscular Dystrophy (DMD) |
| RP4-639D23 | Xp21.3 | 31.6 | |
| RP5-1147O16 | Xp21.3 | 31.8 | |
| RP5-1145L23 | Xp21.2 | 32.1 | |
| RP11-357F9 | Xp21.2 | 32.1 | |
| RP5-1174H9 | Xp21.2 | 32.2 | |
| RP4-672M15 | Xp21.2 | 32.5 | |
| RP4-769D20 | Xp21.2 | 32.6 | |
| RP11-70D7 | Xp21.2 | 33.7 | |
| RP11-258I23 | Xp11.3-Xp11.4 | 40.1 | ← |
| RP11-38O23 | Xp11.1 | 47 | |
| RP11-246G22 | Xq13 | 81.5 | |
| RP11-88F12 | Xq21.3 | 90.8 | ← |
| 125A1 | Xq22.2 | 101.7 | Pelizaeus-Merzbacher Disease (PMD) |
| RP11-832L2 | Xq22.2 | 101.7 | |
| RP11-462K21 | Xq22.2 | 102 | |
| RP11-79N19 | Xq23 | 109.6 | |
| RP11-79C15 | q25 | 123.6 | ← |
| RP11-481F23 | Xq26.3 | 133.3 | |
| RP11-963J21 | Xq27.3 | 143 | Fragile X mental retardation-1 (FMR1) |
| RP11-15O20 | Xq27.3 | 143.5 | |
| RP11-243C2 | Xq28 | 144.5 | |
| RP1-161L9 | Xq27.3 | 144.6 | Fragile X mental retardation-1 (FMR1) |
| RP11-406D14 | Xq28 | 144.7 | |
| RP11-37P24 | Xq27.3 | 145.6 | Fragile X mental retardation-1 (FMR1) |
| RP11-949I9 | Xq27.3 | 145.6 | |
| RP11-489K19 | Xq27.3 | 145.7 | |
| GS-202M24 | Xqter | 147 | |

Fig.23B

NUCLEIC ACIDS ARRAYS AND METHODS OF USE THEREFOR

RELATED APPLICATIONS

This application claims the benefit of U.S. provisional patent application Ser. No. 60/471,216 filed May 16, 2003, and is a continuation-in-part of U.S. patent application Ser. No. 10/273,399 filed Oct. 15, 2002 now U.S. Pat. No. 7,335,470, which claims the benefit of U.S. provisional patent application Ser. No. 60/329,030 filed Oct. 12, 2001, all of which are incorporated herein by reference in their entireties.

TECHNICAL FIELD

This invention provides sets of nucleic acids, and articles of manufacture that are surfaces having multiple arrays, and methods for the detection of chromosomal abnormalities, such as chromosomal aneuploidies, amplifications, deletions, and the like, and a diagnosis or prognosis of syndromes associated with a contiguous gene abnormality. Articles of manufacture are provided that have multiple arrays, each array providing identical blocks having a set of cloned nucleic acids selected as associated with a chromosomal disorder, and having another set of cloned nucleic acids that are selected as not associated with a known disorder.

BACKGROUND

Genomic DNA microarray based comparative genomic hybridization (CGH) has the potential to perform faster, more efficiently and cheaper than traditional CGH methods, which rely on comparative hybridization on individual metaphase chromosomes. Array-based CGH uses immobilized nucleic acids arranged as an array on a biochip or a microarray platform. The so-called array or chip CGH approach can provide DNA sequence copy number information across the entire genome in a single, timely, cost-effective and sensitive procedure. The resolution of chip CGH is primarily dependent upon the number, size and map positions of the DNA elements within the array. Bacterial artificial chromosomes, or BACs, can each accommodate on average about 150 kilobases (kb) of cloned genomic DNA, and are often used in the production of the array.

Array CGH uses genomic DNA from cells of a series of samples to be compared, for example, a test sample and a reference sample (e.g., a sample from cells ideally free of known chromosomal aberrations). The two samples are labeled with different fluorescent dyes, and are mixed and co-hybridized to immobilized nucleic acids, e.g., BACs, or other clones that contain a set of cloned genomic DNA fragments that collectively include a pre-determined portion of a genome or an entire genome. The resulting co-hybridization produces a fluorescently labeled array, and the extent of fluorescence of each of the dyes on each spot reflects competitive hybridization of sequences in the test and reference genomic DNAs to the homologous sequences within the immobilized nucleic acids. Theoretically, the copy number ratio of homologous sequences in the test and reference genomic DNA samples should be directly proportional to the ratio of their respective fluorescent signal intensities at discrete BACs within the array. The versatility of the approach allows detection of constitutional variations in DNA copy number in clinical cytogenetic samples such as amniotic samples, chorionic villus samples (CVS), blood samples and tissue biopsies. It also allows detection of somatically acquired genomic changes in tumorigenically altered cells, for example, from bone marrow, blood or solid tumor samples.

SUMMARY

A feature of the invention is a surface for identifying a chromosomal disorder in a sample taken from a subject, the surface having a plurality of non-contiguous microarrays, such that each microarray comprises a plurality of cloned genomic nucleic acids immobilized on the surface at discrete and known spots, and each microarray comprises a first set of spots having nucleic acids associated with the chromosomal disorder and a second set of spots having control nucleic acids for the chromosome, the control nucleic acids not being associated with any chromosomal disorder on the chromosome. Further provided is a combination comprising this surface. A related embodiment of the combination further has a cover for at least one of the plurality of microarrays. In this combination, the cover functions to separate fluid above at least one microarray from fluid above other microarrays of the plurality. Generally, the surface is planar, and the cover is planar or arcuate in cross section.

The surface material is selected from the group consisting of a metal, silicon, a polymer plastic, paper, ceramic, quartz, gallium arsenide, metal, metalloid, cellulose, celluose acetate, nitrocellulose, and a glass. For example, a glass microscope slide is exemplary for this material. In embodiments in which the material is a plastic, examplary materials are nylon, polycarbonate, polyethylene, polystyrene, teflon, polypropylene, poly(4-methylbuene), polystyrene/latex, polymethacrylate, poly(ethylene terephthalate), rayon, polyvinylbutyrate, and polyvinylidene difluoride.

The surface in one embodiment has nucleic acids associated with a plurality of chromosomes. For example, the plurality of chromosomes comprises the genome of the subject, although a portion of the genome is also within the scope of the claims. Accordingly, the plurality of chromosomes can comprise autosomes. Alternatively or additionally, the plurality of chromosomes comprises at least one sex chromome. Thus in one embodiment, the plurality of chromosomes further comprises an X chromosome and a Y chromosome. In an alternate embodiment the surface has nucleic acids associated with a single chromosome.

In general, the surface of the microarray comprises a plurality of cloned genomic nucleic acids associated with the chromosomal disorder and a plurality of cloned genomic nucleic acids that are not associated with a known chromosomal disorder, i.e., a plurality of control portions of the chromosome. In one embodiment, the plurality of cloned nucleic acids associated with the chromosomal disorder are located on a chromosome that is pre-selected by the user of the surface provided herein. Either or both of the chromosome of interest, or the disorder of interest, can be preselected. Alternatively, the plurality of cloned nucleic acids associated with the chromosomal disorder are located on a plurality of chromosomes, for example, a subset of chromosomes in the genome of the subject, or all of the chromosomes of the subject. Accordingly, both the plurality of control (i.e., backbone) portions and the plurality of disorder-associated portions are distributed among the plurality of chromosomes of the subject.

In general, the microarray further contains a plurality of cloned nucleic acids associated with a plurality of chromosomal disorders. Although embodiments of the microarray having cloned nucleic acids associated with a single disorder are within the scope of the invention, in other embodiments the plurality chromosomal disorders is at least about 5 chromosomal disorders, or is at least about 10 chromosomal disorders, or is at least about 50 chromosomal disorders, or is at least about 100 or 200 chromosomal disorders. In general, the number of chromosomal disorders is less than about 1,000, for example, the microarray contains about 5 to about 1,000 chromosomal disorders, or about 10 to about 300 chromosomal disorders, or about 20 to about 200 chromosomal disorders, or about 40 to about 100 chromosomal disorders. An embodiment of the surface has microarrays having nucleic acids associated with each of about 40 chromosomal disorders. This is a useful number of inherited disorders, since a large majority of inherited chromosomal disorders falls within this group of disorders, and such a surface is valuable for diagnosis and prognosis of a set of most commonly inherited chromosomal disorders.

The microarrays herein may further have at least one calibration spot. For example, the calibration spot includes a mixture of the plurality of cloned genomic nucleic acid not associated with known disorders, and so is a positive control for binding nucleic acids in a reference sample, and also in a test sample. In one embodiment a calibration spot has cloned genomic nucleic acid not associated with known disorders, and also located on the chromosome closely linked to centromere. Exemplary calibration spots of this embodiment can have centromere-linked nucleic acid for any one, or any plurality or all of the chromosomes of a subject organism. An alternative calibration spot has a nucleic acid from an unrelated source, for example, has DNA from a bacterium, an amphibian, or a piscean. Such calibration spots are used with calibration samples, including bacterial, amphibian or piscean nucleic acid, to monitor hybridization efficiency. The calibration samples have a known amount of labeled nucleic acid capable of annealing to, or hybridization with, the calibration spot, hence the efficiency of hybridization of the calibration sample to the calibration spot is useful as a positive control, and for adjustment of the photomultiplier for reading data from the arrays.

The surface in another embodiment has at least one fluid barrier located between at least two of the microarrays, such that the barrier functions to separate hybridization fluid, which is a thin layer of fluid above each microarray, from fluid above other microarrays of the plurality on the surface. In examples of this embodiment, a barrier can be located between each of two microarrays; alternatively, two barriers can be located between each microarray in a linear series of three microarrays. The surface barrier is in one embodiment an elevated structure of hydrophobic composition contiguous with the surface; alternatively, the barrier is a hydrophobic strip printed on the surface. An example of the elevated structure is a glass barrier; alternatively, the elevated structure is a hydrophobic polymer barrier. Exemplary hydrophobic strip are strips printed from solutions or suspensions of polyethylene, silicone, paraffin, or Teflon®. Conditions of the application of strips, such as temperature of the applied material, nature of solvent, printing apparatus, are adjusted for each material.

The invention features in other embodiments a set of cloned genomic nucleic acids comprising portions of nucleotide sequences of at least one chromosome of a subject, the set including a first subset of cloned nucleic acids associated with at least one chromosomal disorder, and a second subset of control cloned nucleic acids not associated with known chromosomal disorders. Generally, the set has a plurality of chromosomal disorders, and the cloned nucleic acids are known to be located at sites on a plurality of chromosomes, for example, autosomes, and/or sex chromosomes. The subject can be a mammal, although the set is useful for any nucleic acid bearing life form such as a virus, a bacterium, a fungus, a protozoan, an alga, a multicellular invertebrate, a cold-blooded vertebrate such as a fish or amphibian, or any bird or reptile. In general, the subject is a human, however the method is also useful for mammals that are rodents, carnivores, ungulates, equines, bovines, caprines, farm animals, zoo animals, agricultural animals, and agricultural plants such as corn, wheat, sorghum, rice and soy.

An embodiment of the invention is a compilation or set of nucleic acids, or an array containing this set, or a surface having multiples of arrays, the set having a plurality of chromosomal disorders each having a substantial frequency in a human population. A substantial frequency is at least one in about $10^5$ births, is at least one in about $10^4$ births, is at least one in about $10^3$ births, or is at least one in about $10^2$ births. Examples of chromosomal disorders are inherited diseases due to chromosomal deletions, insertions, inversions, translocations, and duplications.

In an alternative embodiment, chromosomal disorders are associated with a variety of cancers, and the sets of cloned genomic nucleic acids can be associated with particular cancers, such as cancers of the prostate, the skin, lymphomas and leukemias, breast, pancreatic, liver, and brain, and lung. In an alternative embodiment, the set can contain a subset of cloned nucleic acids commonly associated with various hazardous chemical or physical exposures, to be used for detection of such exposure in a sample obtained from a subject. The sample can be any tissue or bodily fluid containing a source of a nucleic acid. Commonly used are cheek swabs and blood samples, however any tissue or fluid having a cellular component is a source of nucleic acid for the uses and methods herein.

It is a finding of the examples herein that chromosomal disorders are generally associated with or are located near to ends of chromosome or telomeres, and that portions of a chromosome closely linked to centromeres are more commonly free of chromosomal disorders. Closely linked means that the portion of the chromosome is located between the tip of the chromosome and the centromere, for example, and closer to the centromer than to the tip, a distance which varies as measured either in Mb or in CM according to the length of the chromosome. In a long chromosome such as chromosome 1, a centromere-linked portion can be within 10, 20, 50 or even 100 or 150 Mb from the centromere. In a small chromosome, a centromere-linked portion can be within 10, 20, 30 or 40 Mb from the centromere. Accordingly, an embodiment of the invention herein, in addition to providing a set of nucleic acids associated with chromosomal disorders or a "first subset", also provides a second subset which are "backbone" or control cloned nucleic acids, i.e., portions of one or more chromosomes that are closely linked to the centromere (previously referred to as a kinetochore in plants), i.e., the set of cloned nucleic acids generally features a subset of control cloned nucleic acids not associated with known chromosomal disorders that are portions of the chromosome as closely linked to the centromere as possible.

The set can be a set of cloned nucleic acids associated with chromosomal disorders such as: 1p36; Adrenal Hypoplasia Congenita; Alagille Syndrome; Angelman Syndrome; Azospermia Factor A; Azospermia Factor B; Azospermia Factor C; Bruton Agammaglobulinemia Tyrosine Kinase; Beckwith-Wiedemann Syndrome; Charcot-Marie Tooth 1A; Cri-du-chat Syndrome; DiGeorge 1/VCF Syndrome; DiGeorge 2 (10p13); Down Syndrome; Duchenne Muscular Dystrophy; Fragile X syndrome; Glycerol Kinase Deficiency; Greig Syndrome (GLI3), Hereditary Neuropathy with Liability to Pressure Palsies; Hypoparathyroidism, Sensorineural Deafness and Renal Dysplasia; Kallman Syndrome; Langer-Giedion Syndrome (Ext1 and TrpsI); Miller-Dieker Syndrome; Potocki-Shaffer Syndrome (with Multiple Exostoses 2); Neurofibromatosis 1; Pelizaeus-Merzbacher Disorder; Polycystic Kidney Disorder Type I; Prader-Willi Syndrome; Retinoblastoma 1; Rubinstein-Taybi Syndrome; Saethre-Chotzen Syndrome; Sex determining region Y; Smith-Magenis Syndrome; Sotos Syndrome; Steroid Sulfatase Deficiency; Trichorhinophalangeal Syndrome; Tuberous Sclerosis 1; Williams-Beuren Syndrome; Wilm's Tumor; Wilms Tumor-Aniridia-Genitourinary anomalies-Mental retardation (WAGR Syndrome); and Wolf-Hirschhorn Syndrome.

Alternatively, the set of chromosomal disorders is at least one selected from the group of: 1p36; Adrenal Hypoplasia Congenita; Alagille Syndrome; Angelman Syndrome; Azospermia Factor A; Azospermia Factor B; Azospermia Factor C; Bruton Agammaglobulinemia Tyrosine Kinase; Beckwith-Wiedemann Syndrome; Charcot-Marie Tooth 1A; Cri-du-chat Syndrome; DiGeorge 1/VCF Syndrome; DiGeorge 2 (10p13); Down Syndrome; Duchenne Muscular Dystrophy; Fragile X syndrome; Glycerol Kinase Deficiency; Greig Syndrome (GLI3), Hereditary Neuropathy with Liability to Pressure Palsies; Hypoparathyroidism, Sensorineural Deafness and Renal Dysplasia; Kallman Syndrome; Langer-Giedion Syndrome (Ext1 and TrpsI); Miller-Dieker Syndrome; Potocki-Shaffer Syndrome (with Multiple Exostoses 2); Neurofibromatosis 1; Pelizaeus-Merzbacher Disorder; Polycystic Kidney Disorder Type I; Prader-Willi Syndrome; Retinoblastoma 1; Rubinstein-Taybi Syndrome; Saethre-Chotzen Syndrome; Sex determining region Y; Smith-Magenis Syndrome; Sotos Syndrome; Steroid Sulfatase Deficiency; Trichorhinophalangeal Syndrome; Tuberous Sclerosis 1; Williams-Beuren Syndrome; Wilm's Tumor; Wilms Tumor-Aniridia-Genitourinary anomalies-Mental retardation (WAGR Syndrome); and Wolf-Hirschhorn Syndrome.

Alternatively, the set of chromosomal disorders provided herein is related to cancer, and includes cloned nucleic acids associated with tumors or proliferative disorders, for example, from chromosome 8, in particular from the long arm of chromosome 8, in particular the telomeric end of the long arm of chromosome 8, and from chromosomes 9 and 22, in particular, a translocation involving chromosomes 9 and 22 associated with leukemias and forming the oncogene abl. Similar sets or compilations of nucleic acids are envisioned for diagnosing and prognosing exposure to hazardous materials and/or to radiation in the environment. These sets or compilations, and the arrays, or surfaces including arrays such as surfaces having multiple copies of arrays, can be used in conjunction with tester cells, for example, cells of a cell culture that is used to monitor the environment for mutagenic chemical agents and ionizing radiation.

Also featured herein is a method of detecting a chromosomal disorder in nucleic acid samples, the method including: providing a substrate including a surface having a plurality of non-contiguous arrays, each array comprising a plurality of cloned genomic nucleic acids immobilized on the surface at discrete and known spots; contacting a first array with a first solution comprising a detectably labeled first nucleic acid mixture under conditions allowing hybridization between nucleic acids in the first array to nucleci acids in the first mixture, and contacting a second array with a second solution comprising a detectably labeled second nucleic acid mixture under the conditions allowing hybridization, such that the first and second solutions are not in contact; and analyzing amounts of detectable label associated with each spot in the first and second arrays, thereby analyzing the samples to detect the chromosomal disorder in the nucleic acid samples. This method is also a method of performing a plurality of nucleic acid hybridizations on a single surface of a substrate.

In various embodiments of the method, the first and second nucleic acid mixtures include nucleic acid sequences from a test subject and a reference subject. In a related embodiment, the first nucleic acid mixture has test subject nucleic acid detectably labeled with a first fluorescent dye and reference nucleic acid detectably labeled with a second fluorescent dye, and the second nucleic acid mixture has test subject nucleic acid detectably labeled with the second fluorescent dye and reference nucleic acid detectably labeled with the first fluorescent dye. The reference subject is a member of the same species from the test subject and does not carry known chromosomal disorders. Alternatively, the reference subject is a member of a different species as the test subject. In related embodiments, the second nucleic acid is at least one cloned portion of a chromosome. For example, the cloned portion is at least one BAC clone, or is a plurality of BAC clones. Further, the plurality of cloned genomic nucleic acids immobilized in each array includes at least one cloned portion of the genome associated with a chromosomal disorder on a chromosome, and at least one cloned portion of the genome not associated with a chromosomal disorder on the chromosome. In certain embodiments, the first and second solutions further comprise a viscosity increasing solute. The method further includes, after contacting the first array and the second array with the solutions, disposing a cover on each of the first and second solutions.

A feature of the present invention is a method of analyzing genomic nucleic acid of a subject for the presence of a chroosomal disorder, the method comprising: contacting a surface comprising a surface having a first microarray and a second microarray with a first nucleic acid mixture and a second nucleic acid mixture, respectively, the microarrays being non-contiguous on the surface, wherein each microarray comprises a plurality of cloned nucleic acids immobilized on the surface at discrete and known spots; wherein the first mixture comprises test subject nucleic acids linked to a first detectable label and reference nucleic acids linked to a second detectable label, and the first mixture is applied to the first microarray; and the second mixture comprises reference nucleic acids linked to the first detectable label and test nucleic acids linked to the second detectable label, wherein the first mixture and the second mixture are separately contacted to the first and second microarrays, respectively; hybridizing the solution nucleic acids to the microarray nucleic acids under suitable conditions; and, analyzing amounts of first and second labels bound to spots in each of the first and second microarrays, thereby analyzing the sample for the presence of the chromosomal disorders.

Accordingly, the method further involves, after contacting the surface with each of the first mixture and the second mixture, separately applying a cover to each of the first mixture and the second mixture. In a related embodiment, the first and second mixtures further comprise a viscosity-increasing solute. For example, the viscosity-increasing solute is selected from glycerol, polyethylene glycol, albumin, gelatin, and dextran, or any other macromolecule capable of increasing viscosity at low concentration, without affecting rate of nucleic acid hybridization. In the method, analyzing amounts further is measuring the first and second labels bound to spots in the microarrays using an automated scanner. In a related embodiment, analyzing amounts further is measuring labels bound to spots in the microarrays using a laser scanner. Alternatively, using the automated scanner is using a CCD.

For specific embodiments of the method, the first and second microarrays comprise a plurality of cloned portions of the genome associated with a chromosomal disorder on a chromosome, and a plurality of cloned portions of the genome not associated with a chromosomal disorder on the chromosome. In certain embodiments, the first and second microarrays further comprise at least one calibration spot. The calibration spot comprises a mixture of the plurality of cloned genomic nucleic acid from portions of chromosomes not associated with known disorders. Further, the calibration spot comprises cloned genomic nucleic acid from a portion of chromosomes not associated with known disorders and further having locations on the chromosomes closely linked to a centromere. Accordingly, analyzing the amounts is contrasting amount of label bound to the reference nucleic acid spots, with amount of label bound to calibration spots. In alternative embodiments, the calibration spot comprises nucleic acids from a species different than the test subject, and wherein positive control samples comprise predetermined quantities of complementary nucleic acid sequences capable of hybridizing to the calibration spots, and analyzing the positive control data to determine copy number of a gene in the test sample.

Another feature of the invention is a kit comprising a surface having a multiplicity of micro-arrays as described herein, a container, and instructions for use. The kit can further include nucleic acid of a reference subject. The kit can further include a first detectable label and a second detectable label.

In one aspect, the stringent hybridization conditions comprise post-hybridization washing conditions comprising: prewarming the following hybridization solutions at 50° C. in individual Petri dishes: 2×SSC, 50% deionized formamide, 2×SSC, 0.1% NP-40, 0.2×SSC; soaking the array (e.g., a slide) in 2×SSC, 0.5% SDS briefly at room temperature (RT), or alternatively, just 2×SSC can be used; transferring the array (slide) to the pre-warmed 2×SSC, 50% formamide; washing the slides by incubating in the shaking incubator at 50° C. for 20 minutes. In one aspect, the post-hybridization washing conditions comprise repeating the wash using a pre-warmed 2×SSC, 0.1% NP-40. In one aspect, the post-hybridization washing conditions comprise repeating the wash using a pre-warmed 0.2×SSC for 10 minutes. In one aspect, the post-hybridization washing conditions comprise rinsing the slides with distilled deionized water. In one aspect, this last wash does not exceed 10 seconds. In one aspect, the arrays (slides) are immediately dried under forced air.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patent, and GenBank sequences and other references mentioned herein are incorporated by reference in their entirety. In the case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

In FIGS. 1-24, loci for map positions of chromosomal disorders for each chromosome are indicated, as are loci not associated with known chromosomal disorders (leftward pointing arrows). The identifiers of BAC clones carrying nucleic acid sequences for each locus are shown in the first column of the table in the figure. The second column indicates the cytological position on the short or long arm. The third column indicates the position on the chromosome in megabases, from the p terminus at the top.

FIG. 2 is a drawing of human chromosome 2, with arms, loci, positions and clones marked as indicated for FIG. 1.

FIG. 3 is a drawing of human chromosome 3, with arms, loci, positions and clones marked as indicated for FIG. 1.

FIG. 4 is a drawing of human chromosome 4, with arms, loci, positions and clones marked as indicated for FIG. 1.

FIG. 5 is a drawing of human chromosome 5, with arms, loci, positions and clones marked as indicated for FIG. 1.

FIG. 6 is a drawing of human chromosome 6, with arms, loci, positions and clones marked as indicated for FIG. 1.

FIG. 7 is a drawing of human chromosome 7, with arms, loci, positions and clones marked as indicated for FIG. 1.

FIG. 8 is a drawing of human chromosome 8, with arms, loci, positions and clones marked as indicated for FIG. 1.

FIG. 9 is a drawing of human chromosome 9, with arms, loci, positions and clones marked as indicated for FIG. 1.

FIG. 10 is a drawing of human chromosome 10, with arms, loci, positions and clones marked as indicated for FIG. 1.

FIG. 11 is a drawing of human chromosome 11, with arms, loci, positions and clones marked as indicated for FIG. 1.

FIG. 12 is a drawing of human chromosome 22, with arms, loci, positions and clones marked as indicated for FIG. 1.

FIG. 13 is a drawing of human chromosome 13, with arms, loci, positions and clones marked as indicated for FIG. 1.

FIG. 14 is a drawing of human chromosome 14, with arms, loci, positions and clones marked as indicated for FIG. 1.

FIG. 15 is a drawing of human chromosome 15, with arms, loci, positions and clones marked as indicated for FIG. 1.

FIG. 16 is a drawing of human chromosome 16, with arms, loci, positions and clones marked as indicated for FIG. 1.

FIG. 17 is a drawing of human chromosome 17, with arms, loci, positions and clones marked as indicated for FIG. 1.

FIG. 18 is a drawing of human chromosome 18, with arms, loci, positions and clones marked as indicated for FIG. 1.

FIG. 19 is a drawing of human chromosome 19, with arms, loci, positions and clones marked as indicated for FIG. 1.

FIG. 20 is a drawing of human chromosome 20, with arms, loci, positions and clones marked as indicated for FIG. 1.

FIG. 21 is a drawing of human chromosome 12, with arms, loci, positions and clones marked as indicated for FIG. 1.

FIG. 22 is a drawing of human chromosome 22, with arms, loci, positions and clones marked as indicated for FIG. 1.

FIG. 23B is a table related to the drawing of human chromosome X in FIG. 23A.

FIG. 24 is a drawing of human chromosome Y, with arms, loci, positions and clones marked as indicated for FIG. 1.

DETAILED DESCRIPTION OF EMBODIMENTS

Figure 1:
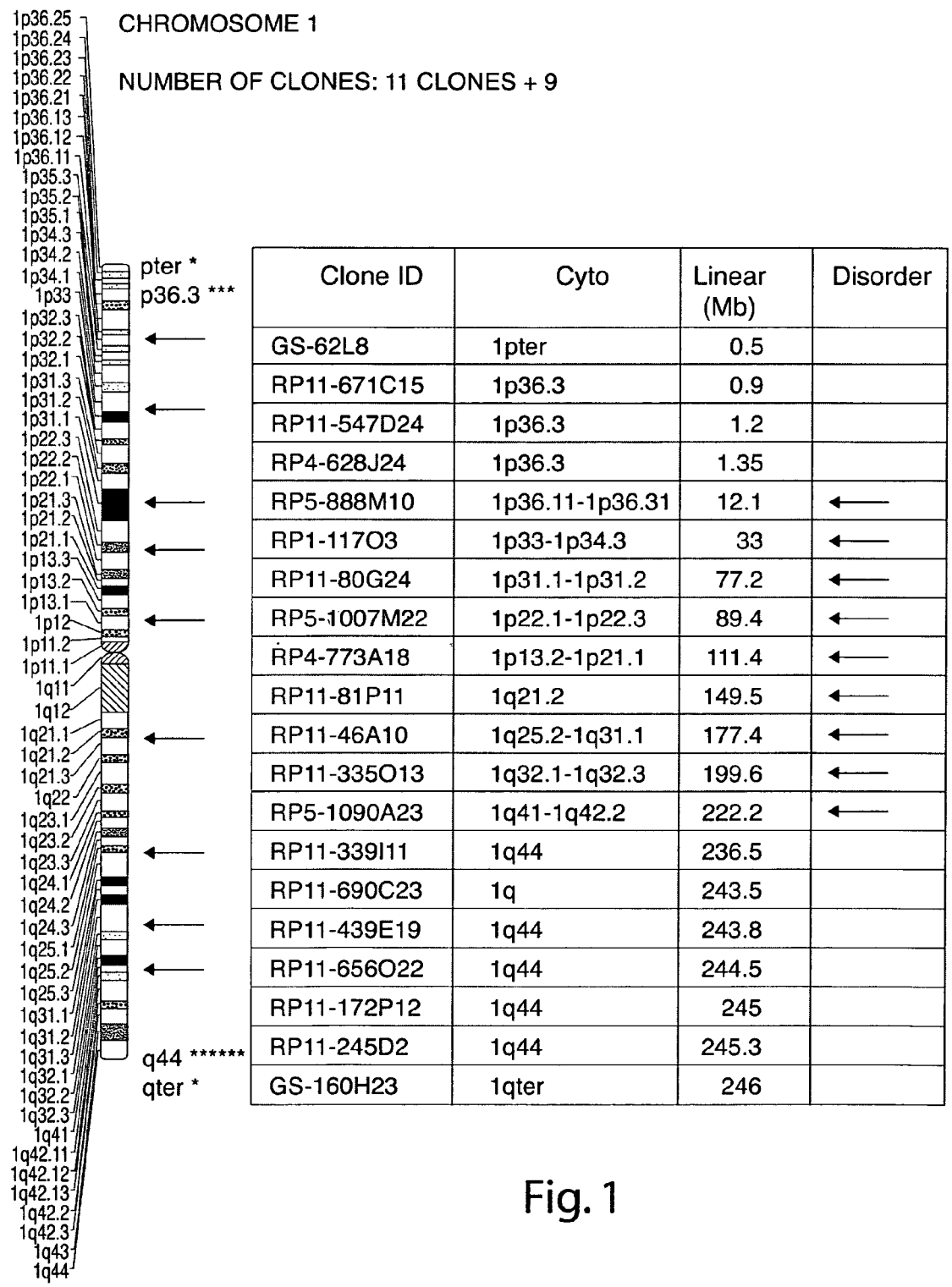
FIG. 1 is drawing of human chromosome 1, with the ideogram showing p, the short arm, at the top and q, the long arm, at the bottom, and the centromere as a constriction.

Novel compilations, or sets (e.g., clone sets), libraries or collections, of nucleic acids and articles of manufacture which are surfaces, i.e., arrays, are shown in application PCT/US02/33044, WO 03/091426A1 published 6 Nov. 2003, the entire contents of which are incorporated herein by reference. In one aspect, these compilations, or sets, libraries or collections, of nucleic acids and arrays are used in the detection of a chromosomal disorder or abnormality, such as a chromosomal aneuploidy (an abnormality involving a chromosome number that is not an exact multiple of the haploid number). They can also be used in the diagnosis or prognosis of a syndrome associated with a contiguous gene abnormality.

The invention in one embodiment provides compilations, or sets, libraries or collections, of nucleic acids and arrays and methods for the detection of a chromosomal abnormality or a diagnosis or prognosis of a syndrome associated with a contiguous gene abnormality. These or sets of nucleic acids and/or arrays can be used for routine or directed genetic screening of embryos, fetuses, children or adults. These sets of nucleic acids and/or arrays can be used to aid in the diagnosis or prognosis of a syndrome, particularly when it is suspected that a patient may have symptoms associated with one or more chromosomal abnormalities, but those symptoms are not definitively diagnostic. Screening of individuals before symptoms appear will allow preventative or prophylactic treatment regimes.

The invention provides methods for selecting genomic fragments, or clone sets (including, e.g., libraries, collections or compilations of fragments or clones), that are effective as hybridization targets in the detection of chromosomal disorder abnormalities, such as aneuploidies (i.e., abnormalities involving a chromosome number that is not an exact multiple of the haploid number), amplification, deletions and the like. In one aspect, these libraries, collections or compilations of genomic fragments or clones are immobilized on articles of manufacture, e.g., arrays. In one aspect, articles of manufacture, e.g., arrays, comprising these libraries, collections or compilations of genomic fragments or clones (e.g., clone sets) are used to perform comparative genomic hybridization (CGH) to detect chromosomal aneuploidies.

The selection process comprises choosing a clone containing a specific region of the chromosome that hybridizes only to a single locus. The selection process can also comprise selection of chromosome fragments (e.g., a plurality of clones) each containing a portion of the genome containing at least 15% unique sequences, i.e., sequences that are not present in the other regions of the genome. Choice of a plurality of clones each of which contains a non-overlapping portion of closely linked portions of a chromosome increases extent of resolution of the technique.

In another aspect, the article of manufacture is a surface having one or a multiple of arrays or microarrays, each array comprising a plurality of as few as about 10 and up to at least about 2500 chromosome fragments (e.g., clones) selected by this method, for example, as described below. Each array of about 10, 40, 125, 250 or more clones is provided in a plurality, i.e., multiple copies which are at least two non-contiguous copies. The genomic clones can be BAC, PAC, MAC, plasmids, recombinant viruses or phagemids and/or cosmids and the like. In one aspect, the selected chromosome fragments (e.g., clones) are cross-linked (immobilized) to a solid surface, e.g., an article of manufacture such as an array.

In one aspect, the selected chromosome fragments (e.g., clones) are immobilized as described in U.S. Pat. No. 6,048,695, the methods therein producing covalent linkage of the nucleic acids to the surface, while minimizing non-specific binding of labeled sample nucleic acid as might otherwise arise using a derivatized surface.

The article of manufacture can be an array comprising the selected chromosome fragments (e.g., clones) immobilized on a surface, for example, a glass slide. In one aspect, the slide is hybridized with fluorescently labeled test and control target DNA. In one aspect, the libraries, collections or compilations of fragments or clones of the invention comprise from about 5 up to about 1,000 or 2,500, for example, about 40 different chromosome fragments (e.g., clones) selected by this method, for example, as described below. Further, each fragment is present in at least one copy in the array, for example, is present in two copies or three copies.

In one aspect, the articles of manufacture, e.g., plurality arrays, each comprises a plurality of nucleic acids segments immobilized on a surface, for example, as an array, or "biochip." In a typical array or array-like format, each segment can be immobilized onto a discrete and known area, or "spot," on the array. Each "spot" comprises a segment of genomic nucleic acid associated with a chromosomal abnormality, a contiguous gene abnormality, a genetically linked disease or a syndrome. In one aspect, while there may be many nucleic acids molecules immobilized on a particular spot, there is only one specie or representation of a genomic nucleic acid segment associated with a chromosomal abnormality per spot.

A subset of the spots of the array of the invention includes a plurality of genomic nucleic acid segments, each associated with a chromosomal abnormality. Another subset of the spots are genomic nucleic acids not associated with any known chromosomal abnormalities. In alternative embodiments, as noted above, varying subpopulations of array spots comprise such genomic nucleic acid segments. In certain embodiments, a set of spots includes nucleic acid segments that serve as positive and/or negative controls. In one aspect, the test samples comprise calibration spots, for example, test and or reference samples are "spiked" with known types and amounts of nucleic acids, such as heterologous nucleic acids, to serve as positive and negative controls.

Also provided are kits comprising the compilations, or sets, libraries or collections of the invention, and/or arrays of the invention. In one aspect, the compilations, or sets, libraries or collections of the invention, and/or arrays of the invention comprise, or consist of at least one, or, all, of the clones as set forth in Tables and Figures herein. The kits can include instructions for use of the compilations, or sets, libraries or collections, of nucleic acids and/or arrays and practicing the methods of the invention, and, for the convenience of the practitioner, materials for extracting genomic DNA from a sample and preparing that DNA, including labeling of the genomic nucleic acid. In one aspect, the kits can also include labeled "wild type" or reference genomic nucleic acid, e.g., human genomic nucleic acid that is provided to serve as a "wild type," i.e., genomic nucleic acid from a subject known not to have any or substantially having no known chromosomal abnormalities and/or any known contiguous gene abnormalities. The "wild type" genomic nucleic acid comprises a substantially complete genome; which is useful if the practitioner is performing a comparative genomic hybridization (CGH). The reference nucleic acid can be a mixture of genomic nucleic acids from several subjects known not to have chromosomal abnormalities or disorders.

BAC clones containing insert DNA, e.g., human genomic DNA, are stored in 25% glycerol, and are kept frozen, for example, at minus 80° C. (stored in a −80° C. freezer).

Definitions

Unless defined otherwise, all technical and scientific terms used herein have the meaning commonly understood by a person skilled in the art to which this invention belongs. As used herein, the following terms have the meanings ascribed to them unless specified otherwise.

The terms "array" or "microarray" or "DNA array" or "nucleic acid array" or "chip" or "biochip" as used herein is a plurality of target elements, each target element comprising a defined amount of one or more biological molecules, e.g., genomic nucleic acid segments, immobilized on a defined location on a substrate surface; as described in further detail, below. In an embodiment of the invention herein, a surface has a plurality, or multiple copies of the array in a non-contiguous arrangement, so that a plurality of hybridizations can be conducted on the surface.

The term "aryl-substituted 4,4-difluoro-4-bora-3a,4a-diaza-s-indacene dye" as used herein includes all "boron dipyrromethene difluoride fluorophore" or "BODIPY" dyes and "dipyrrometheneboron difluoride dyes" (see, e.g., U.S. Pat. No. 4,774,339), or equivalents, are a class of fluorescent dyes commonly used to label nucleic acids for their detection when used in hybridization reactions; see, e.g., Chen (2000) J. Org Chem. 65:2900-2906: Chen (2000) J. Biochem. Biophys. Methods 42:137-151. See also U.S. Pat. Nos. 6,060,324; 5,994,063; 5,614,386; 5,248,782; 5,227,487; 5,187,288.

The terms "cyanine 5" or "Cy5™" and "cyanine 3" or "Cy3™" refer to fluorescent cyanine dyes produced by Amersham Pharmacia Biotech (Piscataway, N.J.) (Amersham Life Sciences, Arlington Heights, IL.), as described in detail, below, or equivalents. See U.S. Pat. Nos. 6,027,709; 5,714,386; 5,268,486; 5,151,507; 5,047,519. These dyes are typically incorporated into nucleic acids in the form of 5-aminopropargyl-2'-deoxycytidine 5'-triphosphate coupled to Cy5™ or Cy3™.

The terms "fluorescent dye" and "fluorescent label" as used herein includes all known fluors, including rhodamine dyes (e.g., tetramethylrhodamine, dibenzorhodamine, see, e.g., U.S. Pat. No. 6,051,719); fluorescein dyes; "BODIPY" dyes and equivalents (e.g., dipyrrometheneboron difluoride dyes, see, e.g., U.S. Pat. No. 5,274,113); derivatives of 1-[isoindolyl]methylene-isoindole (see, e.g., U.S. Pat. No. 5,433,896); and all equivalents. See also U.S. Pat. Nos. 6,028,190; 5,188,934.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which one nucleic acid will hybridize preferentially to second sequence (e.g., a sample genomic nucleic acid hybridizing to an immobilized nucleic acid probe in an array), and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions as used herein can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Those of ordinary skill will readily recognize that alternative but comparable hybridization and wash conditions can be utilized to provide conditions of similar stringency.

The selection of a hybridization format is not critical, as is known in the art, as it is the stringency of the wash conditions that set forth the conditions which are determinative as to whether a soluble, sample nucleic acid will specifically hybridize to an immobilized nucleic acid. Wash conditions can include, e.g.: a salt concentration of about 0.02 molar at pH 7 and a temperature of at least about 50° C. or about 55° C. to about 60° C.; or, a salt concentration of about 0.15 M NaCl and a temperature of at least about 72° C. for at least about 15 minutes; or, a salt concentration of about 0.2×SSC at a temperature of at least about 50° C. or about 55° C. to about 60° C. for at least about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2 ×SSC/0.1% SDS at 42° C. See Sambrook, Ausubel, or Tijssen (cited herein) for detailed descriptions of equivalent hybridization and wash conditions and for reagents and buffers, e.g., SSC buffers and equivalent reagents and conditions.

The phrase "labeled with a detectable composition" or "labeled with a detectable moiety" as used herein refers to a nucleic acid comprising a detectable composition, i.e., a label, as described in detail, below. The label can also be another biological molecule, as a nucleic acid, e.g., a nucleic acid in the form of a stem-loop structure as a "molecular beacon," as described below. This includes incorporation of labeled bases (or, bases which can bind to a detectable label)

into the nucleic acid by, e.g., nick translation, random primer extension, amplification with degenerate primers, and the like. The label can be detectable by any means, e.g., visual, spectroscopic, photochemical, biochemical, immunochemical, physical or chemical means. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin.

The term "nucleic acid" as used herein refers to a deoxyribonucleotide or ribonucleotide in either single- or double-stranded form. The term encompasses nucleic acids containing known analogues of natural nucleotides. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbarniate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). The term nucleic acid is used interchangeably with gene, DNA, RNA, cDNA, mRNA, oligonucleotide primer, probe and amplification product.

The term "genomic DNA" or "genomic nucleic acid" includes nucleic acid isolated from a nucleus of one or more cells, and, includes nucleic acid derived from (e.g., isolated from, amplified from, cloned from, synthetic versions of) genomic DNA. The genomic DNA can be from any source, as discussed in detail, below. The term "wild type genomic nucleic acid" means a sample of genomic nucleic acid having no known or substantially no known contiguous gene abnormalities.

The term "a sample comprising a nucleic acid" or "sample of nucleic acid" as used herein refers to a sample comprising a DNA or an RNA, or nucleic acid representative of DNA or RNA isolated from a natural source, in a form suitable for hybridization (e.g., as a soluble aqueous solution) to another nucleic acid or polypeptide or combination thereof (e.g., immobilized probes). The nucleic acid may be isolated, cloned or amplified; it may be, e.g., genomic DNA, episomal DNA, mitochondrial DNA, mRNA, or cDNA; it may be a genomic segment that includes, e.g., particular promoters, enhancers, coding sequences, and the like; it may also include restriction fragments, cDNA libraries or fragments thereof, etc. The nucleic acid sample may be extracted from particular cells, tissues or body fluids, or, can be from cell cultures, including cell lines, or from preserved tissue sample, as described in detail, below.

As used herein, the terms "computer" and "processor" are used in their broadest general contexts and incorporate all such devices. The methods of the invention can be practiced using any computer/processor and in conjunction with any known software or methodology. For example, a computer/processor can be a conventional general-purpose digital computer, e.g., a personal "workstation" computer, including conventional elements such as microprocessor and data transfer bus. The computer/processor can further include any form of memory elements, such as dynamic random access memory, flash memory or the like, or mass storage such as magnetic disc optional storage.

Generating and Manipulating Nucleic Acids

Making and using the compilations, or sets, libraries or collections of the invention and/or arrays of the invention, and practicing the methods of the invention may involve the isolation, synthesis, cloning, amplification, labeling and hybridization (e.g., CGH) of nucleic acids. The compilations, or sets, libraries or collections of the invention comprise nucleic acid segments. These nucleic acid segments and/or immobilized nucleic acid on the array can be representative of genomic DNA, including defined parts of, or entire, chromosomes, or entire genomes. Comparative genomic hybridization (CGH) reactions, see, e.g., U.S. Pat. Nos. 5,830,645; 5,976,790, are discussed in further detail, below. Nucleic acid samples, the compilations, or sets, libraries or collections of the invention (comprising nucleic acid segments), and, in some aspects, immobilized nucleic acids, can be labeled with a detectable moiety, e.g., a fluorescent dye(s) or equivalent. For example, a first sample can be labeled with a fluor and a second sample labeled with a second dye (e.g., Cy3™ and Cy5™). In one aspect, each sample nucleic acid is labeled with at least one different detectable moiety, e.g., different fluorescent dyes, than those used to label the other samples of nucleic acids.

In some cases, the nucleic acids may be amplified using standard techniques such as PCR. Amplification can also be used to subclone or label the nucleic acid prior to the hybridization. The sample and/or the immobilized nucleic acid can be labeled, as described herein. The sample or the probe on the array an be produced from and collectively can be representative of a source of nucleic acids from one or more particular (pre-selected) portions of, e.g., a collection of polymerase chain reaction (PCR) amplification products, substantially an entire chromosome or a chromosome fragment, or substantially an entire genome, e.g., as a collection of clones, e.g., BACs, PACs, YACs, and the like (see below). The array-immbolilized nucleic acid or genomic nucleic acid sample may be processed in some manner, e.g., by blocking or removal of repetitive nucleic acids or by enrichment with selected nucleic acids.

In one aspect, samples are applied to the immobilized probes (e.g., on the array) and, after hybridization and washing, the location (e.g., spots on the array) and amount of each dye are read. The compilations, or sets, libraries or collections, of nucleic acids or plurality of immobilized nucleic acid segments can be representative of any segment of genomic nucleic acid associated with a chromosomal abnormality, a contiguous gene abnormality, a genetically linked disease or a syndrome; including, e.g., part of or all of a chromosome or genome. The compilations, or sets, libraries or collections, of nucleic acids or array-immobilized nucleic acid can be in the form of cloned DNA, e.g., YACs, BACs, PACs, and the like, as described herein. As is typical of array technology, in one aspect, each "spot" on the array has a known sequence, e.g., a known segment of genome or other sequence. The invention can be practiced in conjunction with any method or protocol or device known in the art, which are well described in the scientific and patent literature.

General Techniques

The nucleic acids used to practice this invention, whether RNA, cDNA, genomic DNA, vectors, viruses or hybrids thereof, may be isolated from a variety of sources, genetically engineered, amplified, and/or expressed/generated recombinantly. Any recombinant expression system can be used, including, in addition to bacterial cells, e.g., mammalian, yeast, insect or plant cell expression systems.

Alternatively, these nucleic acids can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with a primer sequence.

Techniques for the manipulation of nucleic acids, such as, e.g., subcloning, labeling probes (e.g., random-primer labeling using Klenow polymerase, nick translation, amplification), sequencing, hybridization, G-banding, CGH, SKY, FISH and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Cloning of Genomic Nucleic Acids

The compilations, or sets, libraries or collections of the invention, and arrays of the invention, comprise nucleic acids, e.g., genomic nucleic acid segments. The nucleic acids used in the arrays, compilations and methods of the invention, e.g., those immobilized onto arrays or used as samples, can be obtained and manipulated by cloning into various vehicles. If necessary, genomic nucleic acid samples can be screened and re-cloned or amplified from any source of genomic DNA. Thus, in various aspects, forms of genomic nucleic acid used in the methods of the invention (including arrays and samples) include genomic DNA, e.g., genomic libraries, contained in mammalian and human artificial chromosomes, satellite artificial chromosomes, yeast artificial chromosomes, bacterial artificial chromosomes, P1 artificial chromosomes, recombinant vectors and viruses, plasmids, and the like.

Mammalian artificial chromosomes (MACs) and human artificial chromosomes (HAC) are, e.g., described in Ascenzioni (1997) Cancer Lett. 118:135-142; Kuroiwa (2000) Nat. Biotechnol. 18:1086-1090; U.S. Pat. Nos. 5,288,625; 5,721,118; 6,025,155; 6,077,697). MACs can contain inserts larger than 400 kilobase (Kb), see, e.g., Mejia (2001) Am. J. Hum. Genet. 69:315-326. Auriche (2001) EMBO Rep. 2:102-107, has built a human minichromosomes having a size of 5.5 kilobase.

Satellite artificial chromosomes, or, satellite DNA-based artificial chromosomes (SATACs), are, e.g., described in Warburton (1997) Nature 386:553-555; Roush (1997) Science 276:38-39; Rosenfeld (1997) Nat. Genet. 15:333-335). SATACs can be made by induced de novo chromosome formation in cells of different mammalian species; see, e.g., Hadlaczky (2001) Curr. Opin. Mol. Ther. 3:125-132; Csonka (2000) J. Cell Sci. 113 ( Pt 18):3207-3216.

Yeast artificial chromosomes (YACs) can also be used and typically contain inserts ranging in size from 80 to 700 kb. YACs have been used for many years for the stable propagation of genomic fragments of up to one million base pairs in size; see, e.g., U.S. Pat. Nos. 5,776,745; 5,981,175; Feingold (1990) Proc. Natl. Acad. Sci. USA 87:8637-8641; Tucker (1997) Gene 199:25-30; Adam (1997) Plant J.11:1349-1358; Zeschnigk (1999) Nucleic Acids Res. 27:21.

Bacterial artificial chromosomes (BACs) are vectors that can contain cloned inserted DNA of length 120 kb or greater, see, e.g., U.S. Pat. Nos. 5,874,259; 6,277,621; 6,183,957. BACs are based on E. coli F factor plasmid cloning vehicle systems, and are simple to manipulate and purify in microgram quantities. Because BAC plasmids are maintained in vivo at one to two copies per E. coli cell, the problems of rearrangement observed with YACs, which can also be employed in the present methods, are substantially reduced or even eliminated; see, e.g., Asakawa (1997) Gene 69-79; Cao (1999) Genome Res. 9:763-774.

P1 artificial chromosomes (PACs), bacteriophage P1-derived vectors are, e.g., described in Woon (1998) Genomics 50:306-316; Boren (1996) Genome Res. 6:1123-1130; Ioannou (1994) Nature Genet. 6:84-89; Reid (1997) Genomics 43:366-375; Nothwang (1997) Genomics 41:370-378; Kern (1997) Biotechniques 23:120-124). P1 is a bacteriophage that infects E. coli that can contain 75 to 100 kb DNA inserts (see, e.g., Mejia (1997) Genome Res 7:179-186; Ioannou (1994) Nat Genet 6:84-89). PACs are screened in much the same way as lambda libraries. See also Ashworth (1995) Analytical Biochem. 224:564-571; Gingrich (1996) Genomics 32:65-74.

Other cloning vehicles can also be used, for example, recombinant viruses; cosmids, plasmids or cDNAs; see, e.g., U.S. Pat. Nos. 5,501,979; 5,288,641; 5,266,489.

These vectors can include marker genes, such as, e.g., luciferase and green fluorescent protein genes (see, e.g., Baker (1997) Nucleic Acids Res 25:1950-1956). Sequences, inserts, clones, vectors and the like can be isolated from natural sources, obtained from such sources as ATCC or GenBank libraries or commercial sources, or prepared by synthetic or recombinant methods.

Amplification of Nucleic Acids

Amplification using oligonucleotide primers can be used to generate or manipulate, e.g., subclone, nucleic acids of the compilations, or sets, libraries or collections of the invention, nucleic acids used in the arrays of the invention and for practicing the methods of the invention, or to incorporate label into immobilized or sample nucleic acids, or to detect or measure levels of nucleic acids hybridized to an array, and the like. Amplification, typically with degenerate primers, is also useful for incorporating detectable probes (e.g., Cy5™- or Cy3™-cytosine conjugates) into nucleic acids representative of test or control genomic DNA to be used to hybridize to immobilized genomic DNA. Amplification can be used to quantify the amount of nucleic acid is in a sample, see, e.g., U.S. Pat. No. 6,294,338. The skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATE- GIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques, e.g., nucleic acid sequence based amplification, or, "NASBA," see, e.g., Birch (2001) Lett. Appl. Microbiol. 33:296-301; Greijer (2001) J. Virol. Methods 96:133-147. See also Berger (1987) Methods Enzymol. 152:307-316; Sambrook; Ausubel; U.S. Pat. Nos. 4,683, 195 and 4,683,202.

Hybridizing Nucleic Acids

In practicing the methods of the invention, samples of nucleic acid, e.g., isolated, cloned or amplified genomic nucleic acid, are hybridized to the compilations, or sets, libraries or collections of the invention or arrays of the invention, including immobilized nucleic acids. In alternative aspects, the hybridization and/or wash conditions are carried out under moderate to stringent conditions. The invention provides methods for selecting a genomic nucleic acid segment for use as a hybridization target in a hybridization reaction, e.g., a comparative genomic hybridization (CGH) reaction, for the detection of a chromosomal abnormality comprising, inter alia, selecting a chromosomal segment that hybridizes to a single locus under stringent conditions. Exemplary hybridization conditions, including stringent hybridization conditions, are set forth below.

An extensive guide to the hybridization of nucleic acids is found in, e.g., Sambrook Ausubel, Tijssen. Stringent hybridization and wash conditions can be selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

Exemplary stringent hybridization conditions for hybridization of complementary nucleic acids which have more than 100 complementary residues on an array can comprise 42° C. using standard hybridization solutions (see, e.g., Sambrook), with the hybridization being carried out overnight. Exemplary highly stringent wash conditions can also comprise 0.15 M NaCl at 72° C. for about 15 minutes. Exemplary stringent wash conditions can also comprise a 0.2×SSC wash at 65° C. for 15 minutes (see, e.g., Sambrook). In one aspect, a high stringency wash is preceded by a medium or low stringency wash to remove background probe signal. An exemplary medium stringency wash for a duplex of, e.g., more than 100 nucleotides, comprises 1×SSC at 45° C. for 15 minutes. An exemplary low stringency wash for a duplex of, e.g., more than 100 nucleotides, can comprise 4× to 6×SSC at 40° C. for 15 minutes.

In embodiments herein, in making the compilations, or sets, libraries or collections, of nucleic acids or arrays, and practicing the methods of the invention, the fluorescent dyes Cy3™ and Cy5™ are used to differentially label nucleic acid fragments from two samples, e.g., nucleic acid generated from a control (e.g., "wild type" or reference nucleic acid), to be compared to a test cell or tissue sample (sample nucleic acid). In general, both the reference and sample nucleic acids are labeled with each of Cy3™ and Cy5™, and two mixtures are made for a "dye swap" analysis. An embodiment of the methods and surfaces herein is that in providing at least two copies of an array on a single surface, both mixtures of nucleic acids needed to perform the dye swap can be hybridized to the same surface simultaneously. A variety of different techniques can be used alone or in combination to maintain separate fluids for the multiple hybridizations so that each sample is restricted to one array on the surface. As described herein, a cover can be used; other techniques include use of a barrier which is a hydrophobic strip, or a raised barrier above the plane of the surface; and a viscosity-increasing solute can be used to decrease fluidity sufficiently to maintain the position of the fluid above the array. A cover can hold a predetermined volume of the fluid above the microarray by surface tension, for example, a cover slip, or can physically impede movement of the fluid.

Many commercial instruments are designed to accommodate the detection of these two dyes. To increase the stability of Cy5™, or fluors or other oxidation-sensitive compounds, antioxidants and free radical scavengers can be used in hybridization mixes, the hybridization and/or the wash solutions. Thus, Cy5™ signals are dramatically increased and longer hybridization times are possible.

In alternative aspects, the methods of the invention are carried out in a controlled, unsaturated humidity environment, and, the compilations, or sets, libraries or collections, of nucleic acids or arrays of the invention can further comprise apparatus or devices capable of controlling humidity. Controlling humidity is one parameter that can be manipulated to increase hybridization sensitivity. Thus, in one aspect, in practicing the methods of the invention, hybridization can be carried out in a controlled, unsaturated humidity environment; hybridization efficiency is significantly improved if the humidity is not saturated. The hybridization efficiency can be improved if the humidity is dynamically controlled, i.e., if the humidity changes during hybridization. Array devices comprising housings and controls that allow the operator to control the humidity during pre-hybridization, hybridization, wash and/or detection stages can be used. The device can have detection, control and memory components to allow pre-programming of the humidity (and temperature and other parameters) during the entire procedural cycle, including pre-hybridization, hybridization, wash and detection steps.

In alternative aspects, the methods of the invention can incorporate hybridization conditions comprising temperature fluctuations and, the compilations, or sets, libraries or collections, of nucleic acids or arrays of the invention can further comprise apparatus or devices capable of controlling temperature, e.g., an oven. Hybridization has much better efficiency in a changing temperature environment as compared to conditions where the temperature is set precisely or at relatively constant level (e.g., plus or minus a couple of degrees, as with most commercial ovens). Reaction chamber temperatures can be fluctuatingly modified by, e.g., an oven, or other device capable of creating changing temperatures.

In alternative aspects, the methods of the invention can comprise hybridization conditions comprising osmotic fluctuations, and, the compilations, or sets, libraries or collections, of nucleic acids or arrays of the invention can further comprise apparatus or devices capable of controlling osmotic conditions, e.g., generate a e.g., a solute gradient. Hybridization efficiency (i.e., time to equilibrium) can also be enhanced by a hybridization environment that comprises changing hyper-/hypo-tonicity, e.g., a solute gradient. A solute gradient is created in a device. For example, a low salt hybridization solution is placed on one side of the array hybridization chamber and a higher salt buffer is placed on the other side to generate a solute gradient in the chamber.

Fragmentation and Digestion of Nucleic Acid

In practicing the methods of the invention, the compilations, or sets, libraries or collections of nucleic acids, the immobilized and/or sample nucleic acids can be cloned, labeled or immobilized in a variety of lengths. For example, in one aspect, the genomic nucleic acid segments can have a length smaller than about 200 bases. Use of labeled genomic DNA limited to this small size significantly improves the resolution of the molecular profile analysis, e.g., in array-based CGH. For example, use of such small fragments allows for significant suppression of repetitive sequences and other unwanted, "background" cross-hybridization on the immobilized nucleic acid. Suppression of repetitive sequence hybridization greatly increases the reliability of the detection of copy number differences (e.g., amplifications or deletions) or detection of unique sequences.

The resultant fragment lengths can be modified by, e.g., treatment with DNase. Adjusting the ratio of DNase to DNA polymerase in a nick translation reaction changes the length of the digestion product. Standard nick translation kits typically generate 300 to 600 base pair fragments. If desired, the labeled nucleic acid can be further fragmented to segments below 200 bases, down to as low as about 25 to 30 bases, random enzymatic digestion of the DNA is carried out, using, e.g., a DNA endonucleases, e.g., DNase (see, e.g., Herrera (1994) J. Mol. Biol. 236:405-411; Suck (1994) J. Mol. Recognit. 7:65-70), or, the two-base restriction endonuclease CviJI (see, e.g., Fitzgerald (1992) Nucleic Acids Res. 20:3753-3762) and standard protocols, see, e.g., Sambrook, Ausubel, with or without other fragmentation procedures.

Other procedures can also be used to fragment genomic DNA, e.g. mechanical shearing, sonication (see, e.g., Deininger (1983) Anal. Biochem. 129:216-223), and the like (see, e.g., Sambrook, Ausubel, Tijssen). For example, one mechanical technique is based on point-sink hydrodynamics that result when a DNA sample is forced through a small hole by a syringe pump, see, e.g., Thorstenson (1998) Genome Res. 8:848-855. See also, Oefner (1996) Nucleic Acids Res. 24:3879-3886; Ordahl (1976) Nucleic Acids Res. 3:2985-2999. Fragment size can be evaluated by a variety of techniques, including, e.g., sizing electrophoresis, as by Siles (1997) J. Chromatogr. A. 771:319-329, that analyzed DNA fragmentation using a dynamic size-sieving polymer solution in a capillary electrophoresis. Fragment sizes can also be determined by, e.g., matrix-assisted laser desorption/ionization time-of-flight mass spectrometry, see, e.g., Chiu (2000) Nucleic Acids Res. 28:E31.

Syndromes Associated with a Contiguous Gene Abnormality

In one aspect, the invention provides compilations, or sets, libraries or collections of nucleic acids and arrays and methods for the detection of a chromosomal abnormality or for the diagnosis or prognosis of a syndrome associated with a contiguous gene abnormality. Any set or combination of genomic nucleic acid segments associated with a chromosomal abnormality, a contiguous gene abnormality, a genetically linked disease or a syndrome, without limitation, can be used in making and using the compilations, or sets, libraries or collections, of nucleic acids or arrays and practicing the methods of the invention, including genomic nucleic acid segments described herein and genomic nucleic acid segments or other nucleic acids not specifically exemplified herein. For example, the compilations, or sets, libraries or collections of nucleic acids and/or arrays of the invention can comprise, or consist of, at least one, or all of the clones set forth in Table 1.

The compilations, or sets, libraries or collections, of nucleic acids or arrays and methods of the invention also can comprise genomic nucleic acid segments set forth in the literature, see, e.g., Charles R. Scriver, et al., (2000) "The Metabolic and Molecular Bases of Inherited Disease," 8$^{th}$ edition, New York, McGraw-Hill; Pat Gilbert (2000) "The A-Z Reference Book of Syndromes and Inherited Disorders: A Manual for Health, Social and Education Workers" 3 Ed edition, Stanley Thornes Pub Ltd.; Suzanne B. Cassidy, et al. (Ed), (2001) "Management of Genetic Syndromes," Wiley-Liss.

The compilations, or sets, libraries or collections of the invention and/or arrays and methods of the invention can be used for the differential diagnosis of genetically linked diseases or syndromes, formulating appropriate treatment plans and estimating a prognosis. The methods of the invention can be used in situations where the causality, diagnosis, or prognosis (e.g., severity, metastatic potential) of a pathology or condition is associated with one or more genetic defects, e.g., a syndrome caused by a contiguous chromosomal disorder or defect.

A "chromosomal disorder" as used herein means one due to mutations in the genomic nucleic acid, primarily DNA, that are due to amplifications, deletions, inversions, translocations, and generally fall into the category of aneuploidy or deviation of the correct dosage of a chromosome or a portion of a chromosome. Chromosomal disorders can be "congenital" or inherited, i.e., present at or before birth, or can be somatic, i.e., associated with a disease such as cancer or exposure to hazardous materials or radiation. Somatic chromosomal disorders are likely to be characterized as mosaic, i.e., affecting a portion of cells of a tissue or organism.

Considering for example the somatic chromosomal disorders in cancer, determining the presence of a contiguous gene defect can be helpful in predicting or diagnosing and the prognosis of the cancer, classifying a cancer or formulating a treatment plan or prognosis. For example, metastasis suppressor genes on human chromosomes for cutaneous melanoma, as well as a variety of other forms of human cancer, have been located on, e.g., 7q21-22, 7q31.2-32, 8p21-12, 10q11-22, 11p13-11.2, 12p11-q13, 12q24-ter, and 17pter-q23 (see, e.g., Goldberg (2000) Am. J. Hum. Genet. 67(2): 417-431; Ichikawa (2000) Asian J. Androl. 2(3):167-171). Chromosomal abnormalities are common in prostate cancer, including but not limited to, trisomy, hyperdiploidy and aneusomy of chromosomes 7 and 17 (Cui et al., Cancer Genet Cytogenet 107: 51, 19998), amplifications of 6p, 7q, 8q, 9q, and 16q (van Dekken et al., Lab Invest. 83: 789, 2003), deletions of 3q, 6q, 8p, 10q, 13q, 16q, 17p and 20q (Matsuyama et al., Aktuel Urol 34: 247, 2003 and Prostate 54, 103, 2003).

Accordingly, the methods and arrays of the invention can be used for predicting, diagnosing and the prognosis of cancers; chromosomal damage from exposure to hazardous chemical and physical agents and certain inherited conditions. As is well known to those of ordinary skill in oncology, certain chromosomal disorders are correlated with less severe or more severe prognostic outcomes. It is contemplated that as arrays herein become widely standard and data is accumulated for a variety of cancers, additional correlations are made between chromosomal disorders and associated diagnoses and prognoses.

A list below of inherited chromosomal disorders is exemplary of this type of disorder and not further limiting, nor are the methods, compilations, arrays, and surfaces herein limited to inherited disorders.

1p Deletion Syndrome

In one aspect, the compilations, or sets, libraries or collections, of nucleic acids or arrays of the invention comprise a segment of genomic nucleic acid comprising chromosome 1, locus 1p;36, and the syndrome detected is 1p Deletion Syndrome. Patients with deletion of band 1p36.33, have had clinical findings of obesity and hyperphagia; and the overlap of manifestations with Prader-Willi syndrome. See, e.g., Eugster (1997) Am. J. Med. Genet. 70(4):409-412. Patients with karyotypic abnormalities resulting in monosomy for a portion of 1p36.3 can have microcephaly, mental retardation, prominent forehead, deep-set eyes, depressed nasal bridge, flat midface, relative prognathism, and abnormal ears. See, e.g., Reish (1995) Am. J. Med. Genet. 59(4):467-475.

3p Deletion Syndrome

In one aspect, the compilations, or sets, libraries or collections, of nucleic acids or arrays of the invention comprise a segment of genomic nucleic acid comprising chromosome 3, locus 3p25-pter, and the syndrome detected is 3p Deletion Syndrome. Chromosome 3p deletions are thought to be involved in the pathogenesis of sporadic endocrine pancreatic tumors (EPTs); also, von Hippel-Lindau's disease (VHL gene at 3p25.5) has been associated with EPTs. Chromosome 3p deletion is frequently involved in solid human tumors. See, e.g., Barghorn (2001) J. Pathol. 194(4):451-458. Allele loss in some regions of chromosome 3p has been detected in primary breast tumors. See, e.g., Maitra (2001) Am. J. Pathol. 159(1): 119-130.

3p Duplication Syndrome and "C Syndrome"

In one aspect, the compilations, or sets, libraries or collections, of nucleic acids or arrays of the invention comprise a segment of genomic nucleic acid comprising chromosome 3, locus 3p21-pter, and the syndrome detected is 3p Duplication Syndrome. A partial trisomy of chromosome 3P, an inverted duplication 3p22-->3pter (dup(3)(pter-->p26::p22(p26:: p26-->ter)), was found to be associated with psychomotor retardation and slight dysmorphism. A partial 3p trisomy, a 3p/17p translocation: t(3;7)(p253;p133), was found to be associated with mental retardation and poor speech development. See, e.g., Smeets (2001) Genet. Couns. 12(1):85-89. "C syndrome," a multiple congenital anomaly/mental retardation (MCA/MR) syndrome, was found to be associated with a duplication of 3p. See, e.g., McGaughran (2000) Am. J. Med. Genet. 94(4):311-315.

Wolf-Hirschhorn Syndrome and Pitt-Rogers-Danks syndrome

In one aspect, the compilations, or sets, libraries or collections, of nucleic acids or arrays of the invention comprise a segment of genomic nucleic acid comprising chromosome 4, locus 4p16.3, and the syndrome detected is Wolf-Hirschhorn Syndrome. Wolf-Hirschhorn syndrome (WHS) is a well-known congenital malformation syndrome caused by deletion of the short arm of chromosome 4 (4p-). Most cases occur de novo and are of paternal origin. WHS children have severe developmental disabilities. The phenotype of adult WHS is in general similar to that of childhood WHS. Growth retardation, microcephaly and mental retardation are the rule in both adults and children. Facial dysmorphism also remains similar. The main difference lies in the absence of serious internal (cardiac) abnormalities in adult WHS. See, e.g., Battaglia (2001) Adv. Pediatr. 48:75-113; Marcelis (2001) Genet. Couns. 12:35-48. See, e.g., Kant (1997) J. Med. Genet. 34(7): 569-572. Pitt-Rogers-Danks syndrome has also been associated with deletions on chromosome 4p16.

4p Duplication Syndrome

In one aspect, the compilations, or sets, libraries or collections, of nucleic acids or arrays of the invention comprise a segment of genomic nucleic acid comprising chromosome 4, locus 4p15.2-16.1, and the syndrome detected is 4p Duplication Syndrome. Duplications of the distal half of 4p give rise to the partial trisomy 4 syndrome, characterized by a "boxer" nose configuration and deep-set eyes. These signs are usually observed even in cases of small terminal duplications. A "tandem" duplication of 4p16.1p16.3 has been detected in association with a subtle deletion of 4p16.3pter on the same chromosome in a patient with the WHS phenotype. See, e.g., Zollino (1999) Am. J. Med. Genet. 82(5):371-375.

Cri du Chat Syndrome

In one aspect, the compilations, or sets, libraries or collections, of nucleic acids or arrays of the invention comprise a segment of genomic nucleic acid comprising chromosome 5, locus 5p 15.2-pter, and the syndrome detected is Cri du Chat Syndrome. Most patients with cri-du-chat syndrome have a de novo deletion of the short arm of chromosome 5 (5p). Patients show phenotypic and cytogenetic variability. Examples of deletions include: terminal-46,XX,del(5) (pter - - - p15.2:); interstitial-46,XX,del(5) (pter - - - p15.2:: p13.3 - - - qter);46,XX,der(5)t(5;11) (p15;q25)mat. Clinically, younger patients can have a typical high-pitched cry, psychomotor retardation, microcephaly, growth rate failure, and craniofacial abnormalities including round face, hypertelorism, broad nasal bridge, downward slanting palpebral fissures, and micrognathia. See, e.g., Mainardi (2001) J. Med. Genet. 38(3):151-158; Van Buggenhout (2000) Am. J. Med. Genet. 90(3):203-215.

Miller-Dieker Syndrome

In one aspect, the compilations, or sets, libraries or collections, of nucleic acids or arrays of the invention comprise a segment of genomic nucleic acid comprising chromosome 7, locus 7p13.3, and the syndrome detected is Miller-Dieker Syndrome. Trisomy 5p and Miller-Dieker syndromes frequently are the result of unbalanced segregations of reciprocal translocations of chromosomes 5 and 17 with other autosomes. Miller-Dieker Syndrome has been associated with a breakpoint in chromosome 17p13. Miller-Dieker syndrome patients can present with mental retardation, postnatal growth deficiency, generalized muscular hypotonia, seizures, microcephaly, cortical atrophy, partial agenesis of corpus callosum, cerebral ventriculomegaly, facial anomalies. See, e.g., Mutchinick (1999) Am. J. Med. Genet. 85(2):99-104; Pollin (1999) Am. J. Med. Genet. 85(4):369-375.

Williams Syndrome

In one aspect, the compilations, or sets, libraries or collections, of nucleic acids or arrays of the invention comprise a segment of genomic nucleic acid comprising chromosome 7, locus 7q11.23, and the syndrome detected is William's Syndrome. Williams syndrome is typically due to a contiguous gene deletion at 7q11.23, and has been associated with a distinctive facial appearance, cardiac abnormalities, infantile hypercalcemia, and growth and developmental retardation, including mild to severe mental retardation. For example, Williams syndrome was seen in a karyotype having microdeletions at 7q11.23 and 7q36 and additional chromosomal material at 7q36. See, e.g., Donnai (2000) Am. J. Med. Genet. 97(2):164-171; Wouters (2001) Am. J. Med. Genet. 102(3): 261-265.

Langer-Giedion Syndrome (LGS) or TRPS II

In one aspect, the compilations, or sets, libraries or collections, of nucleic acids or arrays of the invention comprise a segment of genomic nucleic acid comprising chromosome 8, locus 8q24.1, and the syndrome detected is Langer-Giedion Syndrome (LGS) or tricho-rhino-phalangeal syndrome type II (TRPS II). It comprises the clinical features of two autosomal dominant diseases, TRPS I, and a form of multiple cartilaginous exostoses caused by mutations in the EXT1 gene. In contrast to TRPS I patients, most TRPS II patients have cytogenetically visible deletions and are often mentally retarded. See, e.g., Hilton (2001) Genomics 71(2):192-199; Nardmann (1997) Hum. Genet. 99(5):638-643. Other syndromes with contiguous deletions of chromosome 8q include Cohen syndrome (8q22-q23), Klip-Feil syndrome (8q22.2), hereditary spastic paraplegia (8q24), and benign adult familial myoclonic epilepsy (8q23.3-q24. 1).

Trichorhinophalangeal Syndrome (TRPS) or TRPS I

In one aspect, the compilations, or sets, libraries or collections, of nucleic acids or arrays of the invention comprise a segment of genomic nucleic acid comprising chromosome 8, locus 8q24.1, and the syndrome detected is Trichorhinophalangeal Syndrome (TRPS) or TRPS I. TRPS I individuals typically have dysmorphic features and severe short stature. TRPS comprises a distinctive combination of hair, facial and bony abnormalities with variable expression. The absence of generalized shortness of all phalanges, metacarpals and metatarsals distinguish it from TRPS III, and absence of exostosis and mental retardation rule out TRPS II. See, e.g., George (1998) J. Eur. Acad. Dermatol. Venereol. 11(1):66-68; Naselli (1998) Pediatr. Radiol. 28(11):851-855.

9p Deletion Syndrome

In one aspect, the compilations, or sets, libraries or collections, of nucleic acids or arrays of the invention comprise a segment of genomic nucleic acid comprising chromosome 9, locus 9p, e.g., locus 9p22-pter, and the syndrome detected is 9p Deletion Syndrome. This syndrome has been associated with de novo deletions in the short arm of chromosome 9. Patients can have developmental delay/mental retardation, seizures and learning disabilities. Mental retardation can be of variable degrees and there can be a marked deficit in visuo-praxic and visuo-spatial skills associated with memory disturbance. See, e g., Chilosi (2001) Am. J. Med. Genet. 100(2):138-144. In contrast, cases of tetrasomy 9p are extremely rare; the principal clinical manifestations of this condition are characteristic craniofacial abnormalities, generalized hypotonia and severe mental retardation, see, e g., Kobayashi (2000) J. Craniomaxillofac. Surg. 28(3):165-170.

DiGeorge Syndrome II

In one aspect, the compilations, or sets, libraries or collections, of nucleic acids or arrays of the invention comprise a segment of genomic nucleic acid comprising chromosome 10, locus 10p13-p14, and the syndrome detected is DiGeorge Syndrome II. This syndrome is characterized by neural-crest-related developmental defects. Partial monosomy 10p is a rare chromosomal condition and a significant proportion of patients show features of DiGeorge syndrome (DGS) and velocardiofacial syndrome (VCFS). One patient with DiGeorge syndrome (DGS) phenotype had an unbalanced translocation [45,XY,−10,−22,+der(10),t(10;22)(p13;q11)] resulting in monosomy of 10p13-pter and 22q11 -pter. See, e.g., Dasouki (1997) Am. J. Med. Genet. 73(1):72-75; Lichtner (2000) J. Med. Genet. 37(1):33-37; Epstein (2001) Trends Genet. 17(10):S13-17.

WAGR Syndrome II

In one aspect, the compilations, or sets, libraries or collections, of nucleic acids or arrays of the invention comprise a segment of genomic nucleic acid comprising chromosome 11, locus 11p13, and the syndrome detected is WAGR Syndrome. The Wilms' tumor-aniridia-genital anomalies-mental retardation (WAGR) syndrome is associated with an increased risk for developing Wilms' tumor. WAGR (Wilms' tumor, aniridia, genital anomalies, and mental retardation) syndrome anomalies have been associated with balanced reciprocal 7;11 translocation and an 11p13 breakpoint. See, e.g., Crolla (1997) J. Med. Genet. 34(3):207-212; Ariel (1996) Pediatr. Pathol. Lab. Med. 16(6):1013-1021.

Beckwith-Wiedemann Syndrome (BWS)

In one aspect, the compilations, or sets, libraries or collections, of nucleic acids or arrays of the invention comprise a segment of genomic nucleic acid comprising chromosome 11, locus 11p15.5, and the syndrome detected is Beckwith-Wiedemann Syndrome. Beckwith-Wiedemann syndrome (BWS) is an imprinting disorder characterized by somatic overgrowth, congenital malformations, and predisposition to childhood tumors. Chromosome 11p15.5 have been reported to have an imprinted gene cluster of 1 Mb, which has been implicated in a wide variety of malignancies and BWS. See, e.g., Li (2001) Genomics 74(3):370-376; Horike (2000) Hum. Mol. Genet. 9(14):2075-2083.

Potocki-Shaffer Syndrome (Multiple Exostoses II Locus)

In one aspect, the compilations, or sets, libraries or collections, of nucleic acids or arrays of the invention comprise a segment of genomic nucleic acid comprising chromosome 11, locus 11p11.2, and the syndrome detected is Potocki-Shaffer Syndrome (Multiple Exostoses II Locus). Potocki-Shaffer Syndrome is caused by a proximal deletion in the short arm of chromosome 11. Patients having the syndrome can have oval defects of the parietal bones (parietal foramina). See, e.g., Wu (2000) Am. J. Hum. Genet. 67(5): 1327-1332.

Angelman Syndrome (AS)

In one aspect, the compilations, or sets, libraries or collections, of nucleic acids or arrays of the invention comprise a segment of genomic nucleic acid comprising chromosome 15, locus 15q12 or 15q13, and the syndrome detected is Angelman Syndrome. It has been reported to be caused by the haploinsufficiency of the 15q11-q13 region, and, de novo deletions of chromosome 15q11-q13. It has also been reported that Angelman syndrome can be caused by genetic abnormalities affecting the maternal copy of chromosome region 15q12. It has been observed that extra copies of this same genomic region, in the form of inv-dup(15) or intrachromosomal duplications, of maternal origin, are usually associated with a severe neurological phenotype characterized by developmental delay and untreatable seizures. See, e.g., Torrisi (2001) Am. J. Med. Genet. 106(2):125-128; Baumer (1999) Hum. Genet. 105(6):598-602; Greger (1997) Am. J. Hum. Genet. 60(3):574-580.

Prader-Willi Syndrome (PWS)

In one aspect, the compilations, or sets, libraries or collections, of nucleic acids or arrays of the invention comprise a segment of genomic nucleic acid comprising chromosome 15, locus 15q12, and the syndrome detected is Prader-Willi Syndrome (PWS). PWS is a neuroendocrine disorder reported to be due to: a large paternally derived chromosome deletion of 15q11q13, to maternal uniparental disomy (UPD), or imprinting mutation (IC). Severe learning disabilities (e.g., attention-deficit hyperactivity disorder), dyslexia, and excessive daytime sleepiness are common symptoms in PWS. See, e.g., Manni (2001) Clin. Neurophysiol. 112(5):800-805; Fernandez-Novoa (2001) Rev. Neurol. 32(10):935-938.

Rubinstein-Taybi Syndrome (RTS)

In one aspect, the compilations, or sets, libraries or collections, of nucleic acids or arrays of the invention comprise a segment of genomic nucleic acid comprising chromosome 16, locus distal 16p13.3, and the syndrome detected is Rubinstein-Taybi Syndrome (RTS). RTS is a malformation syndrome characterized by facial abnormalities, broad thumbs, broad big toes, and mental retardation. In a subset of RTS patients, microdeletions, translocafions, and inversions involving chromosome band 16p13.3 can be detected. Immunodeficiency can be a prominent feature of this syndrome and may predispose these patients to recurrent infections. See, e.g., Petrij (2000) J. Med. Genet. 37(3):168-176; Villella (2000) Arch. Dis. Child. 83(4):360-361.

Charcot-Marie-Tooth Disease Type 1A(CMT-1A)

In one aspect, the compilations, or sets, libraries or collections, of nucleic acids or arrays of the invention comprise a segment of genomic nucleic acid comprising chromosome 17, locus 17p12, and the syndrome detected is Charcot-Marie-Tooth Disease Type 1A(CMT-1A). Charcot-Marie-Tooth neuropathy type 1 (CMT1) is a genetically heterogeneous group of chronic demyelinating polyneuropathies with loci mapping to chromosome 17 (CMT1A), chromosome 1 (CMT1B) and to another unknown autosome (CMT1C). CMT1A accounts for 70-90% of cases of Charcot-Marie-Tooth Disease Type 1 and is most frequently caused by the tandem duplication of a 1.4-Mb genomic fragment on chromosome 17p12. Locus 17p12 is also associated with the peripheral neuropathies, such as hereditary neuropathy with liability to pressure palsies (HNPP) (see below). Some analyses have suggested that the syndrome is associated with de novo 17p11.2 duplication, paternal in origin, arising from unequal crossing over due to homologous recombination between flanking repeat gene clusters. X-linked dominant Charcot-Marie-Tooth (CMTX) disease is a motor and sensory neuropathy caused by mutations in the connexin 32 (CX32) gene. See, e.g., Badano (2001) Clin. Chem. 47(5): 838-843; Potocki (2000) Nat. Genet. 24(1):84-87.

Hereditary Neuropathy (HNPP)

In one aspect, the compilations, or sets, libraries or collections, of nucleic acids or arrays of the invention comprise a segment of genomic nucleic acid comprising chromosome 17, locus 17p12, and the syndrome detected is Hereditary Neuropathy with Liability to Pressure Palsies (HNPP). HNPP is an autosomal dominant disorder that results in a recurrent, episodic demyelinating neuropathy. It also can be characterized by reversible episodes of sensorimotor deficits after neural compression injuries. Also known as tomaculous neuropathy, HNPP is further characterized ultrastructurally by multiple focal thickenings (tomacula) of peripheral myelin and has an autosomal dominant inheritance. HNPP is associated with a 1.5-Mb deletion in chromosome 17p11.2-12 and results from reduced expression of the PMP22 gene. See, e.g., Mersiyanova (2000) Hum. Mutat.15(4):340-347; Chance (2001) Phys. Med. Rehabil. Clin. N. Am. 12(2):277-291; Lane (2001) J. Hand Surg. [Am] 26(4):670-674.

Miller-Dieker Syndrome/Isolated Lissencephaly

In one aspect, the compilations, or sets, libraries or collections, of nucleic acids or arrays of the invention comprise a segment of genomic nucleic acid comprising chromosome 17, locus 17p13.3, and the syndrome detected is Miller-Dieker Syndrome/Isolated Lissencephaly. The Miller-Dieker syndrome (type I lissencephaly) is a neuronal migration disorder that is associated with microdeletions in the short arm of chromosome 17, at locus 17p13.3. For example, one patient was found to have a de novo balanced translocation with breakpoint at 8p11.23 and 17p13.3. In contrast, neurofibromatosis type I (NF1) is an autosomal dominant condition associated with mutations in the long arm of chromosome 17, and characterized by neurofibromas, cafe-au-lait spots and axillary freckling. See, e.g., King (2000) Acta Neuropathol. (Berl) 99(4):425-427; Honda (1998) Brain Dev. 20(3):190-192.

Smith-Magenis Syndrome (SMS)

In one aspect, the compilations, or sets, libraries or collections, of nucleic acids or arrays of the invention comprise a segment of genomic nucleic acid comprising chromosome 17, locus 17p11.2, and the syndrome detected is Smith-Magenis Syndrome (SMS). SMS is a clinically recognizable syndrome comprising multiple congenital anomalies and mental retardation. Its symptoms can include facial anomalies, brachydactyly, severe mental retardation, and self-injuring behavior. SMS is associated with a microdeletion (an interstitial deletion) of the short arm of chromosome 17, locus 17p11.2. Interestingly, a patient with a del(1 7)(p11.2p12) karyotype displayed symptoms of both SMS and Joubert syndrome (JS), the later characterized by cerebellar vermis hypoplasia, hypotonia, ataxic gait, developmental delay, and abnormal respiratory pattern. A prenatal case of SMS found dysmorphic facial features, tetralogy of Fallot, a thymic duct remnant, pancreatic islet cell hyperplasia, and abnormal lung fissuring. See, e.g., Juyal (1996) Am. J. Hum. Genet. 58(5): 998-1007; Natacci (2000) Am. J. Med. Genet. 95(5):467-472; Thomas (2000) Fetal Diagn. Ther. 15(6):335-337. SMS patients have a phase shift of their circadian rhythm of melatonin with a paradoxical diurnal secretion of the hormone. See, e.g., De Leersnyder (2001) J. Med. Genet. 38(9):586-590; De Leersnyder (2001) J. Pediatr. 139(1):111-116; Smith (1998) Am. J. Med. Genet. 81(2):186-191.

Alagille Syndrome (AGS)

In one aspect, the compilations, or sets, libraries or collections, of nucleic acids or arrays of the invention comprise a segment of genomic nucleic acid comprising chromosome 20, locus 20p11.2-p12, and the syndrome detected is Alagille Syndrome (AGS), also known as arteriohepatic dysplasia. Patients can have a deletion in chromosome 20p, with 20p11.23-p12.2 as the area of minimal overlap. One AGS case had a paracentric inversion (PAI) of chromosome 20p12.2p13. Locus 20p11.2-p12 encodes a ligand for the Notch1 transmembrane receptor, which plays a key role in cell-to-cell signaling during differentiation. See, e.g., Yuan (1997) Acta Paediatr. Jpn 39(6):647-652; Hol (1995) Hum. Genet. 95(6):687-690.

Digeorge/Velocardiofacial Syndrome (VCFS)

In one aspect, the compilations, or sets, libraries or collections, of nucleic acids or arrays of the invention comprise a segment of genomic nucleic acid comprising chromosome 22, locus 22q11.2, and the syndrome detected is Digeorge/Velocardiofacial Syndrome (VCFS). VCFS can result from a microdeletion on chromosome 22, locus 22q11.2. VCFS is associated with a broad clinical spectrum characterized by multiple congenital malformations, including cleft palate and cardiac anomalies, that frequently overlaps the DiGeorge syndrome. Estimates suggest that the 22q11.2 deletion occurs in approximately 1 in 4000 live births. Clinical studies indicate that more than 30% of children with VCFS will develop schizophrenia. Velofacial hypoplasia (Sedlackova syndrome) and velocardiofacial (Shprintzen) syndrome are also both associated with del 22q11.2. See, e.g., Eliez (2001) Am. J. Psychiatry 158(3):447-453; Fokstuen (2001) Eur. J. Pediatr. 160(1):54-57; Duke (2000) Arch. Otolaryngol. Head Neck Surg. 126(9):1141-1145.

Adrenal Hypoplasia Congenita (AHC)

In one aspect, the compilations, or sets, libraries or collections, of nucleic acids or arrays of the invention comprise a segment of genomic nucleic acid comprising chromosome X, locus Xp21, and the syndrome detected is Adrenal Hypoplasia Congenita (AHC). AHC patients have a deletion on the short arm of the X chromosome, locus p21.1 to p22. 1. AHC is a developmental disorder of the human adrenal cortex and has been proposed to be caused by deletion or mutation of the DAX-1 gene within locus p21.1 to p22.1; DAX-1 is a member of the nuclear hormone receptor superfamily. The Xp21 syndrome should be considered in any infant with adrenal insufficiency. Measurement of serum triglycerides and creatine kinase activity and karyotype screening tests will facilitate early diagnosis. See, e.g., Peter (1998) J. Clin. Endocrinol. Metab. 83(8):2666-2674; Cole (1994) Clin. Chem. 40(11 Pt 1):2099-2103, and the Glycerol kinase deficiency (GKD) discussion, below.

Duchenne/Becker Muscular Dystrophy

In one aspect, the compilations, or sets, libraries or collections, of nucleic acids or arrays of the invention comprise a segment of genomic nucleic acid comprising chromosome X, locus Xp21, and the syndrome detected is Duchenne/Becker Muscular Dystrophy. Cardiac abnormalities, cardiomyopathy and skeletal muscle weakness have been described in female carriers of the Xp21 (Duchenne and Becker) muscular dystrophies. Duchenne and Becker dystrophies have been associated with the absence or altered expression of dystrophin in cardiac and skeletal muscles. They are frequently complicated by cardiac hypertrophy and dilated cardiomyopathy. See, e.g., Grain (2001) Neuromuscul. Disord. 11(2): 186-191; Crilley (2000) J. Am. Coll. Cardiol. 36(6):1953-1958, and the Glycerol kinase deficiency (GKD) discussion, below.

Glycerol Kinase Deficiency (GKD)

In one aspect, the compilations, or sets, libraries or collections, of nucleic acids or arrays of the invention comprise a segment of genomic nucleic acid comprising chromosome X, locus Xp21, and the syndrome detected is Glycerol Kinase Deficiency (GKD). Glycerol kinase deficiency (GKD) is an X-linked recessive disorder having a deletion on the short arm of the X chromosome, locus p21.1 to p22.1. There are two types. an isolated form and a complex form. The clinical and biochemical phenotype of isolated GKD may vary from a life-threatening childhood metabolic crisis to asymptomatic adult 'pseudohypertriglyceridaemia', resulting from hyperglycerolaemia. The complex GKD is an Xp21 contiguous gene syndrome involving the glycerol kinase locus together with the adrenal hypoplasia congenita (AHC) or Duchenne muscular dystrophy (DMD) loci or both. Complex GKD patients can have an "hourglass" appearance of the middle of the face; hypertelorism; rounded palpebral fissures; esotropia; wide, flattened earlobes; and a downturned mouth. See, e.g., Sjarif (2000) J. Inherit. Metab. Dis. 23(6):529-547; Scheuerle (1995) J. Pediatr. 126(5 Pt 1):764-767.

Pelizaeus-Merzbacher Disease (PMD)

In one aspect, the compilations, or sets, libraries or collections, of nucleic acids or arrays of the invention comprise a segment of genomic nucleic acid comprising chromosome X, locus Xp22, and the syndrome detected is Pelizaeus-Merzbacher Disease (PMD). PMD is an X-linked recessive dysmyelinating disorder of the central nervous system. Most patients have point mutations in exons of the proteolipid protein (PLP1) gene or duplication of a genomic region that includes the PLP1 gene, on locus Xp22, on the short arm of the X chromosome. See, e.g., Hobson (2001) Hum. Mutat. 17(2):152; Hodes (2000) Am. J. Hum. Genet. 67(1):14-22; Inoue (1999) Ann. Neurol. 45(5):624-632.

Steroid Sulfatase Deficiency

In one aspect, the compilations, or sets, libraries or collections, of nucleic acids or arrays of the invention comprise a segment of genomic nucleic acid comprising chromosome X, locus Xp22.3, and the syndrome detected comprises steroid sulfatase deficiency. X chromosome deletions in the Xp22.3 region can result in steroid sulfatase deficiency and X-linked ichthyosis. In one patient, an interstitial deletion in Xp22.3 involved the Kallmann (KAL) gene, the steroid sulfatase (STS) gene and a putative mental retardation locus (MRX). X-linked ichthyosis (XLI) is an inborn error of metabolism due to steroid sulfatase (STS) deficiency. X-linked ichthyosis is a disorder of keratinization characterized by a generalized desquamation of large, adherent, dark brown scales. Extracutaneous manifestations include corneal opacity and cryptorchidism. See, e.g., Weissortel (1998) Clin. Genet. 54(1): 45-51; Santolaya-Forgas (1997) Fetal Diagn. Ther. 12(1):36-39; Valdes-Flores (2001) Am. J. Med. Genet. 102(2):146-148.

Abnormalities of the SRY Locus

In one aspect, the compilations, or sets, libraries or collections, of nucleic acids or arrays of the invention comprise a segment of genomic nucleic acid comprising chromosome Y, locus SRY locus/Yp, and the syndrome detected comprises abnormalities of the SRY (sex-determining region on the Y chromosome) locus. SRY has been identified at band Yp11.31p11.32 in normal XY males and in woman with XY gonadal dysgenesis. SRY signals have also been identified on Xp22 in one XX male. Ullrich-Turner syndrome (UTS) has been associated with Y fragments and gonadoblastomas. Thus, some clinicians have suggested that UTS patients should be examined for Y chromosome material, and that positive cases should have their dysgenic gonads excised due to the high risk of malignancy. See, e.g., Kadandale (2000) Am. J. Med. Genet. 95(1):71-74; Damiani (1999) J. Pediatr. Endocrinol. Metab. 12(6):827-83 1; Kadandale (2000) Microb. Comp. Genomics 5(2):71-74.

Sex Reversal (DSS)

In one aspect, the compilations, or sets, libraries or collections, of nucleic acids or arrays of the invention comprise a segment of genomic nucleic acid comprising chromosome X, locus Xp21, and the syndrome detected is Sex Reversal (DSS). The Xp21 locus contains the gene Ahch, also known as Dax1. Ahch encodes a transcription factor that has been implicated in sex determination and gonadal differentiation. Mutations in human AHC cause X-linked, adrenal hypoplasia congenita (AHC) and hypogonadotropic hypogonadism (HH). Studies have found Xp duplications in patients with sex reversal, with female or ambiguous genitalia occurring in spite of an intact Yp or SRY gene. Five different exchanges have been described two or more times: t(X;Y)(p21;q11), t(X;Y)(p22;p11), t(X;Y)(p22;q11-12), t(X;Y)(q22;q12), and t(X;Y)(q28;q12). See, e.g., Yu (1998) Nat. Genet. 20(4):353-7; Vasquez (1999) Genet. Couns. 10(3):301-334.

Kallman's Disease or Kallmann's Syndrome (KS)

In one aspect, the compilations, or sets, libraries or collections, of nucleic acids or arrays of the invention comprise a segment of genomic nucleic acid comprising chromosome X, locus Xp22.3, and the syndrome detected is Kallman's Disease or Kallmann's syndrome (KS). KS is characterized by hypogonadotrophic hypogonadism in association with anosmia or hyposmia. KS can be associated with X-linked ichthyosis (XLI) in a contiguous gene syndrome comprising a genetic defect in the Xp22.3 region. KS has also been associated with olfactory neuroblastoma. See, e.g., Maya-Nunez (1999) Clin. Endocrinol. (Oxf) 50(2):157-162; Zappia (1992) J. Otolaryngol. 21(1):16-19.

17p11.2 Duplication Syndrome and Birt-Hogg-Dube Syndrome (BHD)

In one aspect, the compilations, or sets, libraries or collections, of nucleic acids or arrays of the invention comprise a segment of genomic nucleic acid comprising chromosome 17, locus 17p11.2, and the syndrome detected is 17p11.2 Duplication Syndrome. Duplication of locus 17p11.2 may be associated with Birt-Hogg-Dube syndrome (BHD), an autosomal dominant neoplasia syndrome characterized mainly by benign skin tumors (e.g., benign tumors of the hair follicle), and to a lesser extent, renal tumors, lung cysts, and spontaneous pneumothorax. The gene for BHD may associated with renal neoplasia and for lung and hair-follicle developmental defects. See, e.g., Schmidt (2001) Am. J. Hum. Genet. 69(4): 876-82; Khoo (2001) Oncogene 20(37):5239-5242.

Idiopathic Epilepsy and Paroxysmal Dyskinesia

In one aspect, the compilations, or sets, libraries or collections, of nucleic acids or arrays of the invention comprise a segment of genomic nucleic acid comprising chromosome 16, pericentromeric region, and the syndrome detected is idiopathic epilepsy and paroxysmal dyskinesia. This is a homogeneous syndrome of autosomal dominant infantile convulsions and paroxysmal (dystonic) choreoathetosis (ICCA). Use of the arrays and methods of the invention may be particularly useful because motor manifestations of epilepsy and of paroxysmal dyskinesia may be difficult to differentiate clinically. See, e.g., Guerrini (2001) Epilepsia 42 Suppl 3:36-41.

Hirschsprung Disease Type 2 and Waardenburg Syndrome

In one aspect, the compilations, or sets, libraries or collections, of nucleic acids or arrays of the invention comprise a segment of genomic nucleic acid comprising chromosome 13, locus 13q22, and the syndrome detected is Hirschsprung disease, including Hirschsprung disease type 2, and Waardenburg syndrome. Hirschsprung disease is a developmental disorder resulting from the arrest of the craniocaudal migration of enteric neurons from the neural crest along gastrointestinal segments of variable length. Waardenburg-Shah syndrome is an auditory pigmentary disorder. Hirschsprung disease, malrotation, isochromia, a profound sensorineural hearing loss, and several other anomalies were found in an infant with an interstitial deletion of 13q, see, e.g., Shanske (2001) Am. J. Med. Genet. 102(3):231-236.

Branchio-Oto-Renal (BOR) Syndrome

In one aspect, the compilations, or sets, libraries or collections, of nucleic acids or arrays of the invention comprise a segment of genomic nucleic acid comprising 8, locus 8q13.3, and the syndrome detected is branchio-oto-renal (BOR) syndrome. Branchio-oto-renal (BOR) syndrome is an autosomal dominant disorder involving hearing loss, branchial defects, ear pits and renal abnormalities. The arrays and methods of the invention can be used to distinguish it from oto-facio-cervical (OFC) syndrome, which is clinically similar to BOR syndrome, with clinical features in addition to those of BOR syndrome. See, e.g., Rickard (2001) Hum. Genet. 108(5): 398-403.

Smith-Magenis Syndrome (SMS)

In one aspect, the compilations, or sets, libraries or collections, of nucleic acids or arrays of the invention comprise a segment of genomic nucleic acid comprising chromosome 1, locus 7p 11.2, and the syndrome detected is Smith-Magenis syndrome (SMS). Smith-Magenis syndrome (SMS) is a multiple congenital anomaly/mental retardation (MCA/MR) syndrome link to a contiguous-gene deletion syndrome, involving chromosome 1 7p 11.2,whose incidence is estimated to be 1:25,000 live births. SMS is characterized by a specific physical, behavioral and developmental pattern. The main clinical features consist of a broad flat midface with brachycefaly, broad nasal bridge, brachydactily, speech delay, hoarse deep voice and peripheral neuropathy. See, e.g., Di Cicco (2001 Int. J. Pediatr. Otorhinolaryngol. 59(2):147-150.

Leri-Weill Syndrome

In one aspect, the compilations, or sets, libraries or collections, of nucleic acids or arrays of the invention comprise a segment of genomic nucleic acid comprising chromosome X, locus Xp22.3, and the syndrome detected is Leri-Weill syndrome. Leri-Weill syndrome is characterized by short stature (SHOX), chondrodysplasia punctata (ARSE), bilateral Madelung deformity and mental retardation. See, e.g., Spranger (1999) Am. J. Med. Genet. 83(5):367-371.

Chromosome abnormalities are common causes of congenital malformations and spontaneous abortions. They include structural abnormalities, polyploidy, trisomy, and mosaicism. Very few autosomal trisomies survive to birth, the three most common being those for chromosome 13, 18 and 21 giving rise to the syndromes named Patau, Edward's and Down's respectively (see, e.g., Moore (2000) Eur. J. Hum. Genet. 8:223-228). Thus, in alternative aspects, the arrays methods of the invention are used to diagnose Patau Syndrome, Edward's Syndrome and Down's Syndrome. See, e.g., Djalali (2000) Prenat. Diagn. 20:934-935. Table 1 shows a set of exemplary chromosomal disorders that can be diagnosed by the compilations, or sets, libraries or collections, of nucleic acids, arrays and methods of the invention:

TABLE 1

Chromosome Loci Profiles of Contiguous Gene Syndromes

| Chromosome number | Locus | Syndrome |
| --- | --- | --- |
| 1 | 1p36 | 1p Deletion Syndrome |
| 3 | 3p25 - pter | 3p Deletion Syndrome |
| 3 | 3p21 - pter | 3p Duplication Syndrome |
| 4 | 4p16.3 | Wolf-Hirschhorn Syndrome |
| 4 | 4p15.2 - 16.1 | 4p Duplication Syndrome |
| 5 | 5p15.2 - pter | Cri du Chat Syndrome |
| 7 | 7p13.3 | Miller-Dieker Syndrome |
| 7 | 7p11.23 | William's Syndrome |
| 8 | 8q24.1 | Langer-Giedion Syndrome (LGS) |
| 8 | 8q24.1 | Trichorhinophalangeal Syndrome (TRPS) |
| 9 | 9p, usually 9p22 - pter | 9p Deletion Syndrome |
| 10 | 10p13p14 | DiGeorge Syndrome II |
| 11 | 11p13 | WAGR Syndrome |
| 11 | 11p15.5 | Beckwith-Wiedemann Syndrome |
| 11 | 11p11.2 | Potocki-Shaffer Syndrome (Multiple Exostoses II Locus) |
| 15 | 15q12 | Angelman Syndrome |
| 15 | 15q12 | Prader-Willi Syndrome |
| 16 | Distal 16p13.3 | Rubinstein-Taybi Syndrome |
| 17 | 17p12 | Charcot-Marie-Tooth Disease Type 1A(CMT-1A) |
| 17 | 17p12 | Hereditary Neuropathy with Liability to Pressure Palsies |
| 17 | 17p13.3 | Miller-Dieker Syndrome/Isolated Lissencephaly |
| 17 | 17p11.2 | Smith-Magenis Syndrome |
| 20 | 20p11.2p12 | Alagille Syndrome |
| 22 | 22q11.2 (also see 1-p13p14) | Digeoege/Velocardiofacial Syndrome |
| X | Xp21 | Adrenal Hypoplasia Congenita (AHC) |
| X | Xp21 | Duchenne/Becker Muscular Dystrophy |
| X | Xp21 | Glycerol Kinase Deficiency |
| X | Xp22 | Pelizaeus-Merzbacher Disease |
| X | Xp22.3 | Steroid Sulfatase Deficiency |
| Y | SRY locus/Yp | Abnormalities of the SRY locus |

The sets of nucleic acids, arrays and methods of the invention can also be used to detect aneuploidy of chromosomes 13, 18, 21, X, and Y from genomic DNA from newborn uncultured blood samples (see, e.g., Jalal (1997) Mayo Clin. Proc. 72:705-710). Chromosomal abnormalities have been reported to occur in approximately 1%-2% of viable pregnancies studied by chorionic villus sampling at 9-11 weeks of gestation. See, e.g., Harrison (1993) Hum. Genet. 92:353-358.

In in vitro fertilization (IVF) programs, preimplantation genetic diagnosis (PGD) of oocytes and embryos has become the technique of choice to select against abnormal embryos before embryo transfer. Thus, in alternative aspects, the compilations, or sets, libraries or collections, of nucleic acids, arrays and methods of the invention are used for preimplantation genetic diagnosis and the diagnosis of chromosomal abnormalities and structural abnormalities in oocytes and embryos. See, e.g., Fung (2001) J. Histochem. Cytochem. 49:797-798. Thus, in alternative aspects, the compilations, or sets, libraries or collections, of nucleic acids, arrays and methods of the invention are used with chorionic villus sampling (CVS) and fetal karyotyping. See, e.g., Sanz (2001) Fetal Diagn. Ther. 16:95-97.

Genetic defects are frequent among transgenic animals produced by pronuclear microinjection. A successful method for the screening of founder animals for a chromosomal abnormality prior to mating would greatly reduce the costs associated with the propagation of the transgenic lines, and improve the efficiency of transgenic livestock production. Thus, in alternative aspects, the compilations, or sets, libraries or collections, of nucleic acids, arrays and methods of the invention are used in the production of transgenic animals, particularly, the screening of founder animals for gene defects prior to mating. See, e.g., Ibanez (2001) Mol. Reprod. Dev. 58:166-172.

Comparative Genomic Hybridization (CGH)

In one aspect, sets of nucleic acids of the invention, and/or the arrays and methods of the invention incorporate array-based comparative genomic hybridization (CGH) reactions to detect chromosomal abnormalities, e.g., contiguous gene abnormalities, in cell populations, such as tissue, e.g., biopsy or body fluid samples. CGH is a molecular cytogenetics approach that can be used to detect regions in a genome undergoing quantitative changes, e.g., gains or losses of sequence or copy numbers. Analysis of genomes of tumor cells can detect a region or regions of anomaly under going gains and/or losses.

CGH reactions compare the genetic composition of test versus controls samples; e.g., whether a test sample of genomic DNA (e.g., from a cell population suspected of having one or more subpopulations comprising different, or cumulative, genetic defects) has amplified or deleted or mutated segments, as compared to a "negative" control, e.g., "normal" or "wild type" genotype, or "positive" control, e.g., a known cancer cell or a cell with a known defect, e.g., a translocation or deletion or amplification or the like.

Making and using the compilations, or sets, libraries or collections, of nucleic acids, arrays and practicing the methods of the invention can incorporate all known methods and means and variations thereof for carrying out comparative genomic hybridization, see, e.g., U.S. Pat. Nos. 6,197,501; 6,159,685; 5,976,790; 5,965,362; 5,856,097; 5,830,645; 5,721,098; 5,665,549; 5,635,351; and, Diago (2001) American J. of Pathol. May; 158(5):1623-1631; Theillet (2001) Bull. Cancer 88:261-268; Werner (2001) Pharmacogenomics 2:25-36; Jain (2000) Pharmacogenomics 1:289-307.

Arrays or "BioChips"

The invention provides articles of manufacture, such as arrays, comprising the nucleic acid compilations, or sets, libraries or collections of the invention. For example, in one aspect, invention provides an article of manufacture comprising, or consisting of, at least one, or all, of the nucleic acid segments described in Table 1. Making and using the compilations, or sets, libraries or collections, of nucleic acids, arrays and practicing the methods of the present invention can incorporate any known "array," also referred to as a "microarray" or "DNA array" or "nucleic acid array" or "biochip," or variation thereof. Arrays are generically a plurality of "target elements," or "spots," each target element comprising a defined amount of one or more biological molecules, e.g., polypeptides, nucleic acid molecules, or probes, immobilized on a defined location on a substrate surface. Typically, the immobilized biological molecules are contacted with a sample for specific binding, e.g., hybridization, between molecules in the sample and the array. Immobilized nucleic acids can contain sequences from specific messages (e.g., as cDNA libraries) or genes (e.g., genomic libraries), including, e.g., substantially all or a subsection of a chromosome or substantially all of a genome, including a human genome. Other target elements can contain reference sequences, such as positive and negative controls, and the like. The target elements of the arrays may be arranged on the substrate surface at different sizes and different densities. Different target elements of the arrays can have the same molecular species, but, at different amounts, densities, sizes, labeled or unlabeled, and the like. The target element sizes and densities will depend upon a number of factors, such as the nature of the label (the immobilized molecule can also be labeled), the substrate support (it is solid, semi-solid, fibrous, capillary or porous), and the like. Each target element may comprise substantially the same nucleic acid sequences, or, a mixture of nucleic acids of different lengths and/or sequences. Thus, for example, a target element may contain more than one copy of a cloned piece of DNA, and each copy may be broken into fragments of different lengths, as described herein. The length and complexity of the nucleic acid fixed onto the array surface is not critical to the invention. The array can comprise nucleic acids immobilized on any substrate, e.g., a solid surface (e.g., nitrocellulose, glass, quartz, fused silica, plastics and the like). See, e.g., U.S. Pat. No. 6,063,338 describing multi-well platforms comprising cycloolefin polymers if fluorescence is to be measured. Arrays used in the methods of the invention can comprise housing comprising components for controlling humidity and temperature during the hybridization and wash reactions.

In making and using the compilations, or sets, libraries or collections, of nucleic acids, arrays and practicing the methods of the invention, known arrays and methods of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765. The present invention can use any known array, e.g., GeneChips™, Affymetrix, Santa Clara, Calif.; SPECTRALCHIP™ Mouse BAC Arrays, SPECTRALCHIP™ Human BAC Arrays and Custom Arrays of Spectral Genomics, Houston, Tex., and their accompanying manufacturer's instructions.

In alternative embodiments, the compilations, or sets, libraries or collections, of nucleic acids of the invention, and the articles of manufacture, such as arrays, of the invention, can comprise one, several or all of the human genomic nucleic acid segments set forth below in FIGS. 1-24. These clones are identified by RP, GS, CTC or other CT clone names; the descriptors for clones are in Nature 409:953-958 (2001), "Integration of cytogenetic landmarks into the draft sequence of the human genome." The BAC Resource Consortium. A second column gives the cytological position of each as a marker on either the short arm, p, or long arm, q, of the chromosome indicated, e.g. 8p23.3 is at the p arm telomere of chromosome 8, as shown in the ideogram of the chromosome in FIG. 8. The numbers in the third column of each Fig. indicate the linear position of the cloned nucleic acid segment on the chromosome in megabases (Mb). These figures show clones that represent all 24 human chromosomes at a resolution of about or less than about 1 Mb resolution. The resolution is determined in part by the number of different cloned portions in a given length of a chromosome selected to be spotted on the array, and the nature of the cloned portions, i.e., whether they are overlapping or non-overlapping, and if non-overlapping, the extent of the gap between the cloned portions.

Substrate Surfaces

The nucleic acid compilations, or sets, libraries or collections of the invention can be immobilized (directly or indirectly, covalently or by other means) to any substrate surface. The arrays of the invention can incorporate any substrate surface, e.g., a substrate means. The substrate surfaces can be of a rigid, semi-rigid or flexible material. The substrate surfaces can be flat or planar, be shaped as wells, raised regions, etched trenches, pores, beads, filaments, or the like. Substrates can be of any material upon which a nucleic acid (e.g., a "capture probe") can be directly or indirectly bound. For example, suitable materials can include paper, glass (see, e.g., U.S. Pat. No. 5,843,767), ceramics, quartz or other crystalline substrates (e.g. gallium arsenide), metals, metalloids, polacryloylmorpholide, various plastics and plastic copolymers, Nylon™, Teflon™, polyethylene, polypropylene, poly (4-methylbutene), polystyrene, polystyrene/latex, polymethacrylate, poly(ethylene terephthalate), rayon, nylon, poly(vinyl butyrate), polyvinylidene difluoride (PVDF) (see, e.g., U.S. Pat. No. 6,024,872), silicones (see, e.g., U.S. Pat. No. 6,096,817), polyformaldehyde (see, e.g., U.S. Pat. Nos. 4,355,153; 4,652,613), cellulose (see, e.g., U.S. Pat. No. 5,068,269), cellulose acetate (see, e.g., U.S. Pat. No. 6,048,457), nitrocellulose, various membranes and gels (e.g., silica aerogels, see, e.g., U.S. Pat. No. 5,795,557), paramagnetic or superparamagnetic microparticles (see, e.g., U.S. Pat. No. 5,939,261) and the like. Reactive functional groups can be, e.g., hydroxyl, carboxyl, amino groups or the like. Silane (e.g., mono- and dihydroxyalkylsilanes, aminoalkyltrialkoxysilanes, 3-aminopropyl-triethoxysilane, 3-aminopropyltrimethoxysilane) can provide a hydroxyl functional group for reaction with an amine functional group.

Multi-Array Surfaces

Multi-array surfaces provided herein have on each surface a plurality of copies of the micro-array, i.e., micro-arrays (arrays) of biological molecules, for example, nucleic acids. The term "multi-array surface" or "surface" as used herein means an article of manufacture having a plurality of micro-arrays applied to a side or a face of a substrate. In general the micro-arrays are printed or spotted or otherwise deposited on the face of the substrate, in an arrangement such that the micro-arrays are non-contiguous, i.e., the arrays are distal from each other on the surface, or are not in contact, compared to the size of each array and the spacings of the spots within each array.

A multi-array surface having a plurality of arrays is desirable for the following procedures: hybridizations are conducted in duplicate or triplicate on a single surface. Previous to the present invention, duplicate or triplicate or even a greater number of replicated spots have been described that are present on a single surface, however all spots were exposed to hybridization of a single hybridization mixture. The hybridization mixture is a solution that typically contains a nucleic acid sample from a test subject labeled with a fluorescent dye, or a mixture of two different samples of nucleic acids of different origins, each labeled with the same or a different dye. The hybridization mixture is formed prior to hybridization with the spots of the array on the surface, for example, the mixture includes nucleic acids from test subject labeled with a first fluorescent dye and nucleic acids that are a reference sample, labeled with a different dye. The reference sample can be nucleic acids from a normal individual of the same species as the test subject, or can be nucleic acids of a different species, or nucleic acids from a single BAC clone or from a mixture of BAC clones. For BAC clones, NCBI maintains a human BAC resource, which provides genome-wide information concerning large-insert clones that integrate cytogenetic, radiation-hybrid, linkage, and sequence maps of the genome. See www.ncbi.nlm.nih.gov/genome/cyto/hrbc.shtml.

It is often desirable, in analyzing such data, to perform the hybridization in two different formats that reverse the fluorescent labels, what is commonly described as a "label reversal", "label swap" or "dye swap" analysis. In a dye swap analysis, at least two nucleic acid samples are to be compared, and at least two mixtures are made. In the first mixture, a first label such as a first fluorescent dye is used to identify the reference nucleic acid probe, and a second label such as a second fluorescent dye is used to identify the test sample, and after labeling each, the mixture is made. Then the labels are reversed, i.e., a second mixture is made in which the reference nucleic acid probe carries the second dye and the test sample carries the first dye. Each of the two mixtures provides a reference for the purpose of plotting amounts of hybridization of each solution nucleic acid, reference and test sample, to each of the immobilized cloned nucleic acids. The results are plotted as a function of the linear position of each of the cloned immobilized nucleic acids on a chromosome. Then a representation is made of a portion or of an entire chromosome, or of a plurality of chromosomes, or of a complete set of chromosomes (autosomes with or without sex chromosomes), i.e., of the entire genome. Results obtained from analyzing both sets of data are combined to reveal changes that would otherwise be undetectable if label reversal was not used. This is because small fluctuations from a ratio of 1.0 become statistically significant when the dye swap data are plotted together, which might not be significant if only a single mixture was used.

Further, it is often desirable to compare multiple test subjects with the same reference sample. In any of these uses, multiple identical arrays are necessary.

Prior to the methods and surfaces as described herein, it has been necessary to conduct such analyses using a plurality of different replicas of the printed surfaces. For example, a dye swap analysis was performed with two mixtures, the first being a mixture of the test nucleic acid labeled with the first dye and mixed with the reference nucleic acid labeled with the second dye, and the second being the test nucleic acid labeled with the second dye mixed with the reference nucleic acid labeled with the first dye, the two mixtues then being analyzed using two different surfaces.

The use of separate hybridizations on different surfaces can be a source of variability, e.g., in efficiency of binding of spots to each surface, hybridization due to variability in conditions, minor variations in concentration of each nucleic acid, variation in concentrations, different efficiencies in elution of non-specifically bound materials due to minor variations in washing procedures or solutions, at the time of hybridization to each separate surface, or variations in photomultiplier settings in a scanner used to visualize and evaluate the array, after hybridization to each separate surface. Accordingly, the present surfaces provided herein address this problem in the prior common usage by having multi-arrays, which are a plurality of arrays on a single surface.

In a non-limiting example, two arrays are located at distal ends of a planar substrate such as a standard glass microscope slide, however alternative shapes and sizes of substrates, and shapes and sizes of arrays, are within the scope of surfaces, kits and methods envisioned herein. For example, a substrate may be a one inch by 3 inch microscope slide, and may have a plurality of arrays such as two arrays, one at either end, or four arrays in a linear arrangement. A larger substrate such as a square slide may have four arrays, one in each corner, or nine arrays with three arrays on each side and one in the middle.

Further, barriers to maintain separation of fluids deposited on each array during hybridization may be used, the barriers being placed between each of the arrays, in addition to embodiments of the surface in the absence of barriers, as described herein. The barriers are physical "dykes" or "dams" having a height above the plane of the substrate face or surface, and such barriers include raised portions of the substrate as manufactured, or as added subsequently. Alternatively, the barriers may be hydrophobic materials that are printed on the substrate to produce a "strip" which can prevent the flow of an aqueous solution from one array to another. The barriers can be added before or after printing or depositing the micro-arrays, to produce the multi-array surfaces.

The barriers are comprised of a material that is not soluble in aqueous solution, and the material hydrophobic. Exemplary hydrophobic materials for barrier construction or printing include: polyethylene, silicone, paraffin, and Teflon®.

Hybridization using the "multi-array surfaces" having multiple arrays on a single surface of a single substrate, is conducted by adding the hybridization mixture to the array and protecting the hybridization mixture with a cover to prevent loss of volume of solution by evaporation, and to confine each hybridization of a particular sample or mixture of samples, labeled with one or more dyes as described above, to the appropriate micro-array. A pre-determined amount of hybridization mixture is deposited above the array, such that addition of a cover, for example placed directly on the fluid, yields a resulting thin layer of fluid above the array in which the sample nucleic acids can hybridize to complementary sequences within the array. Hybridization for each array on the surface is conducted under a separate cover.

Conditions for hybridization can be modified, for example, the hybridization solution can be altered, to assure fluid separation of the multiple hybridizations on the surface. For example, viscosity of the hybridization fluid may be increased to reduce fluidity by adding one or more solutes that do not interact with the nucleic acids during the hybridization. Exemplary solutes include small molecules that are viscous liquids such as glycerol, and polymers of small molecules such as sugars which is exemplified by dextrans and starches such as corn starch, polymers of amino acids which are synthetic polypeptides or naturally occurring proteins such as albumins and gelatins, and synthetic polymers, for example, polyethylene glycol, or polyacrylamide or agarose, each at a concentration sufficient to increase viscosity without significantly affecting mobility of the solute nucleic acids for interaction and hybridization (annealing to form a double stranded complex) to the immobilized nucleic acids. The viscosity increasing solute may be chemically modified to improve its properties, for example, to render it resistant to digestion by extracellular enzymes of bacteria and fungi. Solutions for hybridization may be stored with antibiotic or growth inhibiting materials to retard spoilage during storage.

The multi-array surfaces and methods herein are not limited to performance of dye swap analyses. For example, a multi-array surface having four or nine arrays can be used to analyze multiple samples, for example, a plurality of members of a nuclear family, or multiple siblings and a proband carrying a chromosomal disorder, which can now be analyzed together on a single substrate having multiple micro-arrays, using separate hybridizations. Further, any multiple number of subjects can be analyzed simultaneously on a single substrate, or any one subject can be analyzed in mixtures of different reference samples. Different reference samples can be different species, different known mutations, or different predeteremined single BAC or mixtures of BAC clones.

Chromosomal Analysis using Calibration Spots and Disease-Negative Clones

Calibration spots that act as positive controls for hybridization of a sample, and that are located within an array have been described (see, U.S. patent application 2003-0186250-A1, published Oct. 2, 2003, and incorporated herein in its entirety by reference). In embodiments of the surfaces and methods provided herein, calibration spots may include a subset of cloned nucleic acids, for example, those clones of the human genome carrying sequences not known by any published references to be associated with a chromosomal disorder or disease. These clones are indicated in FIGS. 1-24 by left-pointing arrows, and may be considered to be "non-reactive" or "backbone" clones, which act as positive hybridization controls, i.e., provide portions of the chromosome for any chromosome of interest that will hybridize to nucleic acid from a test subject. The term, "non-reactive" means that the nucleic acid generally hybridizes to a full extent to a genomic nucleic acid from any test subject, i.e., and is "non-reactive" because it does not give a false "positive" diagnosis of a chromosomal disorder. Because the non-reactive or backbone clones are positive controls for hybridization, they are therefore expected to be non-reactive with a test sample for detection of a chromosomal disorder.

A calibration spot may be a mixture of nucleic acids from backbone clones, for any one chromosome, or for all of the chromosomes in the human genome or genome of any other organism. An exemplary calibration spot may comprise a mixture of nucleic acids from backbone clones, for example, from about 10, from about 20, from about 40, or from about 80 backbone or non-reactive clones. An exemplary calibration spot contains 72 non-reactive backbone clones, selected to represent each of the set of autosomes and sex chromosomes. An alternative calibration spot contains nucleic acid from an unrelated heterologous species, such as a fish or amphibian, for purposes of standardizing hybridization, in which case an internal control carrying a recognizable label can be added or "spiked" into each hybridization mixture.

Representation of each chromosome is made by calculating ratios of labels in each of the two double dye-labeled hybridizations (dye swap) and relative amounts are plotted graphically as a function of distance of each cloned chromosomal portion from the p terminus conventionally shown on the left. By convention, one of the two double labeled materials is plotted in a consistent line format (e.g., double line), and the other in a different color line format (e.g., solid line), such that deletion of a portion of nucleic acid in a test subject is displayed using a double line above the 1.0 ratio line (see FIGS. 25A-25F and FIGS. 26A-26F), and an insertion such as an amplification is plotted as solid line above the 1.0 ratio line.

Analyses shown herein have made the unexpected finding that nucleic acid sequences in subjects corresponding to clones carrying nucleotide sequences closely linked to telomeres have a greater extent of association with chromosomal disorders, while clones carrying centromere-linked sequences have the least extent of chromosomal disorders. A calibration spot that is a mixture of exclusively centromere-linked nucleic acids, or substantially having centromere-linked nucleic acids, provides a strong positive control that is useful for one exemplary calibration spot as described herein.

In addition, the arrays provided herein as shown in drawings and examples herein, include cloned nucleic acids from portions of each chromosome that are not associated with any known chromosomal disorders, so that representations of a chromosome of a test subject's DNA is facilitated, and a chromosomal disorder on a given chromosome is more readily distinguished from normal portions of that chromosome.

Nucleic Acids and Detectable Moieties: Incorporating Labels and Scanning Arrays

In making and using the nucleic acid compilations, or sets, libraries or collections of the invention and arrays and practicing the methods of the invention, nucleic acids associated with a detectable label can be made and used and incorporated into the compositions of the invention. The detectable label can be incorporated into, associated with or conjugated to a nucleic acid. Any detectable moiety can be used. The association with the detectable moiety can be covalent or non-covalent. In another aspect, the array-immobilized nucleic acids and sample nucleic acids are differentially detectable, e.g., they have different labels and emit difference signals.

Useful labels include, e.g., $^{32}P$, $^{35}S$, $^{3}H$, $^{14}C$, $^{125}I$, $^{131}I$; fluorescent dyes (e.g., Cy5™, Cy3™, FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, dioxigenin, or haptens and proteins for which antisera or monoclonal antibodies are available. The label can be directly incorporated into the nucleic acid to be detected, or it can be attached to a probe or antibody that hybridizes or binds to the target. A peptide can be made detectable by incorporating (e.g., into a nucleoside base) predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties. See, e.g., Mansfield (1995) Mol Cell Probes 9:145-156. In array-based CGH, fluors can be paired together; for example, one fluor labeling the control (e.g., the "nucleic acid of "known, or normal, karyotype") and another fluor the test nucleic acid (e.g., from a chorionic villus sample or a cancer cell sample). Exemplary pairs are: rhodamine and fluorescein (see, e.g., DeRisi (1996) Nature Genetics 14:458-460); lissamine-conjugated nucleic acid analogs and fluorescein-conjugated nucleotide analogs (see, e.g., Shalon (1996) supra); Spectrum Red™ and Spectrum Green™ (Vysis, Downers Grove, IL.); Cy3™ and Cy5™. Cy3™ and Cy5™ can be used together; both are fluorescent cyanine dyes produced by Amersham Life Sciences (Arlington Heights, IL.). Cyanine and related dyes, such as merocyanine, styryl and oxonol dyes, are particularly strongly light-absorbing and highly luminescent, see, e.g., U.S. Pat. Nos. 4,337,063; 4,404,289; 6,048,982.

Other fluorescent nucleotide analogs can be used, see, e.g., Jameson (1997) Methods Enzymol. 278:363-390; Zhu (1994) Nucleic Acids Res. 22:3418-3422. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

Detectable moieties can be incorporated into sample genomic nucleic acid and, if desired, any member of the compilation of nucleic acids or array-immobilized nucleic acids, by covalent or non-covalent means, e.g., by transcription, such as by random-primer labeling using Klenow polymerase, or "nick translation," or, amplification, or equivalent. For example, in one aspect, a nucleoside base is conjugated to a detectable moiety, such as a fluorescent dye, e.g., Cy3™ or Cy5™, and then incorporated into a sample genomic nucleic acid. Samples of genomic DNA can be incorporated with Cy3™- or Cy5™-dCTP conjugates mixed with unlabeled dCTP. Cy5™ is typically excited by the 633 nm line of HeNe laser, and emission is collected at 680 nm. See also, e.g., Bartosiewicz (2000) Archives of Biochem. Biophysics 376: 66-73; Schena (1996) Proc. Natl. Acad. Sci. USA 93:10614-10619; Pinkel (1998) Nature Genetics 20:207-211; Pollack (1999) Nature Genetics 23:41-46.

In another aspect, when using PCR or nick translation to label nucleic acids, modified nucleotides synthesized by coupling allylamine-dUTP to the succinimidyl-ester derivatives of the fluorescent dyes or haptenes (such as biotin or digoxigenin) are used; this method allows custom preparation of most common fluorescent nucleotides, see, e.g., Henegariu (2000) Nat. Biotechnol. 18:345-348.

In the nucleic acid compilations, libraries, sets, or collections, or arrays and methods of the invention, labeling with a detectable composition (labeling with a detectable moiety) also can include a nucleic acid attached to another biological molecule, such as a nucleic acid, e.g., a nucleic acid in the form of a stem-loop structure as a "molecular beacon" or an "aptamer beacon." Molecular beacons as detectable moieties are well known in the art; for example, Sokol (1998) Proc. Natl. Acad. Sci. USA 95:11538-11543, synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (2001) Biochemistry 40:9387-9395, describing a molecular beacon comprised of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi (2001) Anal. Biochem. 294:126-131; Poddar (2001) Mol. Cell. Probes 15:161-167; Kaboev (2000) Nucleic Acids Res. 28:E94. Aptamer beacons can adopt two or more conformations, one of which allows ligand binding. A fluorescence-quenching pair is used to report changes in conformation induced by ligand binding. See also, e.g., Yamamoto (2000) Genes Cells 5:389-396; Smirnov (2000) Biochemistry 39:1462-1468.

Detecting Dyes and Fluors

In addition to labeling nucleic acids with fluorescent dyes, the invention can be practiced using any apparatus or methods to detect "detectable labels" of a sample nucleic acid, a member of the compilation of nucleic acids, or an array-immobilized nucleic acid, or, any apparatus or methods to detect nucleic acids specifically hybridized to each other. In one aspect, devices and methods for the simultaneous detection of multiple fluorophores are used; they are well known in the art, see, e.g., U.S. Pat. Nos. 5,539,517; 6,049,380; 6,054,279; 6,055,325; 6,294,331. Any known device or method, or variation thereof, can be used or adapted to practice the methods of the invention, including array reading or "scanning" devices, such as scanning and analyzing multicolor fluorescence images; see, e.g., U.S. Pat. Nos. 6,294,331; 6,261,776; 6,252,664; 6,191,425; 6,143,495; 6,140,044; 6,066,459; 5,943,129; 5,922,617; 5,880,473; 5,846,708; 5,790,727; and, the patents cited in the discussion of arrays, herein. See also published U.S. patent applications Nos. 20010018514; 20010007747; published international patent applications Nos. WO0146467 A; WO9960163 A; WO0009650 A; WO0026412 A; WO0042222 A; WO0047600 A; WO0101144 A.

For example a spectrograph can image an emission spectrum onto a two-dimensional array of light detectors; a full spectrally resolved image of the array is thus obtained. Photophysics of the fluorophore, e.g., fluorescence quantum yield and photodestruction yield, and the sensitivity of the detector are read time parameters for an oligonucleotide array. With sufficient laser power and use of Cy5™ and/or Cy3™, which have lower photodestruction yields an array can be read in less than 5 seconds.

When using two or more fluors together (e.g., as in a CGH), such as Cy3™ and Cy5™, it is necessary to create a composite image of all the fluors. To acquire the two or more images, the array can be scanned either simultaneously or sequentially. Charge-coupled devices, or CCDs, are used in microarray scanning systems, including practicing the methods of the invention. Thus, CCDs used in the methods of the invention can scan and analyze multicolor fluorescence images.

Color discrimination can also be based on 3-color CCD video images; these can be performed by measuring hue values. Hue values are introduced to specify colors numerically. Calculation is based on intensities of red, green and blue light (RGB) as recorded by the separate channels of the camera. The formulation used for transforming the RGB values into hue, however, simplifies the data and does not make reference to the true physical properties of light. Alternatively, spectral imaging can be used; it analyzes light as the intensity per wavelength, which is the only quantity by which to describe the color of light correctly. In addition, spectral imaging can provide spatial data, because it contains spectral information for every pixel in the image. Alternatively, a spectral image can be made using brightfield microscopy, see, e.g., U.S. Pat. No. 6,294,331.

Data Analysis

The methods of the invention further comprise data analysis, which can include the steps of determining, e.g., fluorescent intensity as a function of substrate position, removing "outliers" (data deviating from a predetermined statistical distribution), or calculating the relative binding affinity of the targets from the remaining data. The resulting data can be displayed as an image with color in each region varying according to the light emission or binding affinity between targets and probes. See, e.g., U.S. Pat. Nos. 5,324,633; 5,863,504; 6,045,996. The invention can also incorporate a device for detecting a labeled marker on a sample located on a support, see, e.g., U.S. Pat. No. 5,578,832.

Sources of Genomic Nucleic Acid

The invention provides methods of detecting a genetic mosaicism in any sample comprising nucleic acid, such as a cell population or tissue or fluid sample, by performing an array-based comparative genomic hybridization (CGH). The nucleic acid can be derived from (e.g., isolated from, amplified from, cloned from) genomic DNA. The genomic DNA can be from any source.

In one aspect, the cell, tissue or fluid sample from which the nucleic acid sample is prepared is taken from a patient suspected of having a pathology or a condition associated with genetic defects. The causality, diagnosis or prognosis of the pathology or condition may be associated with genetic defects, e.g., with genomic nucleic acid base substitutions, amplifications, deletions and/or translocations. The cell, tissue or fluid can be from, e.g., amniotic samples, chorionic villus samples (CVS), serum, blood, chord blood or urine samples, CSF or bone marrow aspirations, fecal samples, saliva, tears, tissue and surgical biopsies, needle or punch biopsies, and the like.

Methods of isolating cell, tissue or fluid samples are well known to those of skill in the art and include, but are not limited to, aspirations, tissue sections, drawing of blood or other fluids, surgical or needle biopsies, and the like. A "clinical sample" derived from a patient includes frozen sections or paraffin sections taken for histological purposes. The sample can also be derived from supernatants (of cell cultures), lysates of cells, cells from tissue culture in which it may be desirable to detect levels of mosaicisms, including chromosomal abnormalities and copy numbers.

Making Nucleic Acid Arrays

Making BAC Microarrays

Bacterial strains carrying BAC clones having cloned insert DNA of observed sizes greater than about fifty kilobases (50 kb), and up to about 300 kb, are grown in Terrific Broth medium. Cells having BAC clones with larger inserts, e.g., clones >300 kb, and smaller inserts, about 1 to 20 kb, may also be used. DNA is prepared in one embodiment by a modified alkaline lysis protocol (see, e.g., Sambrook), however, any protocol for purifying DNA is within the scope of the method. The DNA is labeled, as described below.

The DNA is then chemically modified as described by U.S. Pat. No. 6,048,695. The modified DNA is then dissolved in proper buffer and printed directly on clean glass surfaces as described by U.S. Pat. No. 6,048,695. Usually multiple spots are printed for each clone.

Nucleic Acid Labeling and Fragmentation

A standard random priming method is used to label genomic DNA before its attachment to the array, see, e.g., Sambrook. Sample nucleic acid is also similarly labeled. Cy3™ or Cy5™ labeled nucleotides are supplemented together with corresponding unlabeled nucleotides at a molar ratio ranging from 0.0 to about 6 (unlabeled nucleotide to labeled nucleotides). Labeling is carried out at 37° C. for 2 to 10 hours. After labeling the reaction mix is heated up to 95° C. to 100° C. for 3 to 5 minutes to inactivate the polymerase and denature the newly generated, labeled "probe" nucleic acid from the template.

The heated sample is then chilled on ice for 5 minutes. "Calibrated" DNase (DNA endonuclease) enzyme is added to fragment the labeled template (generated by random priming). "Trace" amounts of DNase is added (final concentration was 0.2 to 2 ng/ml; incubation time 15 to 30 minutes) to digest/fragment the labeled nucleic acid to segments of about 30 to about 100 bases in size. Alternatively, DNA is fragmented by sonication.

Nucleic acids are alternatively fragmented by sonication. Sonication protocols include establishing standard power levels and times of sonication, to obtain fragments of desired length.

Hybridization of Nucleic Acid Samples to Arrays

The examples set forth herein provide exemplary methods for pretreating nucleic acid samples and hybridizing these samples to arrays. This exemplary hybridization protocol can be used to determine if a nucleic acid segment, such as a genomic clone, is within the scope of the invention (e.g., is a member of a compilation, library, clone set of the invention).

Pretreatment of Sample DNA

Random prime labeling of large sized DNA samples, such as genomic DNA, can be more efficient if the DNA sample is first digested or otherwise treated to produce smaller fragments of more uniform size and mobility in solution. For every test sample to be analyzed, four digests of genomic DNA were performed: two of the test sample and two of an appropriate reference or control sample.

1. Restriction enzyme digest of genomic DNA: on ice, pipet the following into an autoclaved microcentrifuge tube:
   DNA× μl for 1 μg
   React 3 10× Buffer 5 μl
   Eco R1 2 μl (20units)
   Water (orange vial) μl to a final volume of 50 μl
2. After addition of the enzyme and DNA, mix briefly by vortexing and recollect samples by brief centrifugation.
3. Incubate samples overnight (16 hours) at 37° C.
4. Determine the completion of the reaction by removing a 5 μl aliquot from the reaction mix, and analyzing the aliquot by agarose gel electrophoresis (0.8% agarose).
   If the digestion is complete, stop the reaction by incubating in a heating block at 72° C. for 10 minutes. It is recommended to fill the wells of the heating block with water approximately 15 minutes before denaturing the samples so that the tubes are in contact with water at 72° C.
5. Re-purify the digested DNA sample (either by phenol/chloroform extraction/EtOH precipitation or a suitable commercially available 'post-enzyme digestion/PCR clean-up kit' such as Zymo Research's DNA Clean and Concentrator TM-5 Cat No. D4005). Note: It is recommended to requantifying the DNA samples at this juncture to ensure that equitable amounts of the test and reference samples will be labeled in the following step. At least 500 ng of digested DNA of each sample were used for labeling.
   Genomic DNA samples adequately digested with a four base pair (4-bp) cutter restriction enzyme, such as EcoR1, should produce a relatively homogenous smear extending from 20 kb to approximately 600 bp.

Differential Labeling of DNA with Cy3-dCTP and Cy5-dCTP

The objective in this step is to label the test and reference samples with both Cy-3 and Cy-5 to facilitate the co-hybridization between the Cy-3 labeled test and Cy-5 labeled reference samples, and conversely the Cy-5 labeled test and Cy-3 labeled reference samples.

1. To the re-purified DNA samples, add sterile water to bring the total volume to 25 μl. Then add 20 μl of 2.5× random primer/reaction buffer mix (e.g., from Gibco/BRL's BIOPRIME™ labeling kit).
2. Mix the samples well and then boil for 5 minutes.
3. Immediately place the samples on ice and allow to sit for 5 minutes.
4. On ice, add 2.5 μl of SPECTRAL LABELING BUFFER, for use with SPECTRAL CHIP™ (Spectral Genomics, Houston Tex.) to each sample.
5. Add 1.5 μl Cy5-dCTP or Cy3-dCTP to the respective test and reference DNA samples (1 mM stocks).
6. Finally, add 1 μl Klenow Fragment (from the Gibco/BRL BIOPRIME™ labeling kit) to the samples, mix the sample well by tapping, and re-collect by brief centrifugation.
7. Incubate the sample at 37° C for 1½-2 hours. Place the samples on ice and determine the probe size distribution by removing a 5 μl aliquot from the reaction mix, and analyzing the aliquot by agarose gel electrophoresis (0.8% agarose). Note: Optimally, the majority of the probe should range in size between 100-500 bp.
8. Stop the reaction by adding 5 μl 0.5 M EDTA pH8.0 and incubating in a heating block at 72° C. for 10 minutes. Place the samples on ice. The samples can now be used to proceed with hybridization or can be stored at −20° C. until required.

Optimally the majority of the probe should range in size between 100-500 bp.

Hybridizing Labeled DNA to the Array

At this juncture, there should be four tubes, which should correspond to the Cy-3 and Cy-5 labeled test samples and the Cy-3, and Cy-5 labeled reference samples.

1. Combine the Cy3-labeled test DNA sample with the Cy5-labeled reference sample and, conversely, the Cy5-labeled test DNA sample with the Cy3-labeled reference sample. Add 45 μl of SPECTRAL HYBRIDIZATION BUFFER I, for use with SPECTRAL CHIP™ (Spectral Genomics, Houston Tex.) to each of the two tubes.
2. Precipitate the two samples by adding 11.3 μl of 5MNaCl and 101 μl of room temperature isopropanol. Mix the samples well and incubate in the dark at room temperature for 10-15 minutes.
3. Centrifuge the samples at full speed (10,000 g) for 10 minutes.
4. Aspirate the supernatant, avoiding the pellet. Note: The pellets should have a purplish hue, indicating that there are expected amounts of Cy3 and Cy5 labeled DNA. Too pink or too blue a sample, suggests that the corresponding genomic DNA was not appropriately labeled.
5. Rinse the pellets with 500 μl of 70% ethanol and allow the pellets to air-dry briefly in the dark at room temperature.
6. Add 10 μl of sterile water (orange vial) to the pellets. Let stand at room temperature for 5 minutes and then thoroughly resuspend. After ensuring that the pellets are completely resuspended, add 30 μl of SPECTRAL HYBRIDIZATION BUFFER II, for use with SPECTRAL CHIP™ (Spectral Genomics, Houston Tex.) and mix well by repeated pipetting.
7. Denature the samples by incubating in a water bath at 72° C. for 10 minutes. Note: Alternatively, the sample can be denatured in a heating block set at 72° C. We recommend filling the wells of the heating block with water approximately 15 minutes before denaturing the samples so that the tubes are in contact with water at 72° C.

8. After the denaturation of the samples, immediately place the tubes on ice for 5 minutes.
9. Incubate the samples at 37° C. for 30 minutes.
10. Pipette the sample onto the center of the array and cover with a 22×60 cover slip to spread it out. Note: It is imperative that the entire array is covered and that air bubbles are avoided.
11. Place the slide in a hybridization chamber. If a microarray hybridization chamber is used, then add 10 µl of 2×SSC, 50% formamide to either side of the chamber. (H₂O works just as well).
12. Close the chamber and wrap with aluminum foil. Put the chambers in a Kapak Pouch with wet paper and heat seal the bag. Put the bag in a 37° C. incubator for 16 hours. Note: We recommend using a shaking platform incubator to facilitate and maintain even distribution of the probe on the slide.

Post Hybridization Washes

While Coplin jars can be used in the post-hybridization washes, it is recommended to wash each slide in individual Petri dishes in a shaking platform incubator.
1. Pre-warm the following solutions at 50° C. in individual Petri dishes:
2×SSC, 50% deionized Formamide
2×SSC, 0.1% NP-40
0.2×SSC
2. Soak the slide in 2×SSC, 0.5% SDS briefly at room temperature and gently slide off the cover slip using a pair of clean forceps. Avoid peeling off the cover slip by force. (Alternatively, 2×SSC can be used)
3. Using a pair of forceps, transfer the slide to pre-warmed 2×SSC, 50% Formamide. Wash the slides by incubating in the shaking incubator at 50° C. for 20 minutes.
4. Repeat step 3 using pre-warmed 2×SSC, 0.1% NP-40.
5. Repeat step 3 using pre-warmed 0.2×SSC for 10 minutes.
6. Briefly rinse the slides with distilled deionized water. This last wash greatly reduces background fluorescence but should not exceed 10 seconds.
7. Immediately dry the slides under forced air. Do not air dry the slides. The slides are now ready for scanning.

EXAMPLES

Example 1

Analysis of Chromosomal Disorders on Human Chromosome 1

In FIG. 1 is seen an ideogram of chromsome 1. On the right side of the ideogram and in the table are listed three BAC clones carrying nucleic acid sequences corresponding to a syndrom known as 1p36, and six clones associated with a syndrome known as 1q44, which are named for known chromosomal disorders that are associated with known areas of chromosome 1.

Also shown are nine clones carrying portions of chromosome 1 that are not associated with known chromosomal disorders (leftward pointing arrows). Further, some of these clones are closely linked to the centromere of chromosome 1, which is indicated by the constriction in the ideogram between 1p11 and 1q11. Microarrays were prepared on glass slides having DNA from the listed BAC clones in FIG. 1 that contain these loci on chromosome 1, and the slides further had two copies of each of the microarrays.

Example 2

Analysis of Chromosomal Disorders on Human Chromosome 2

Figure 2:
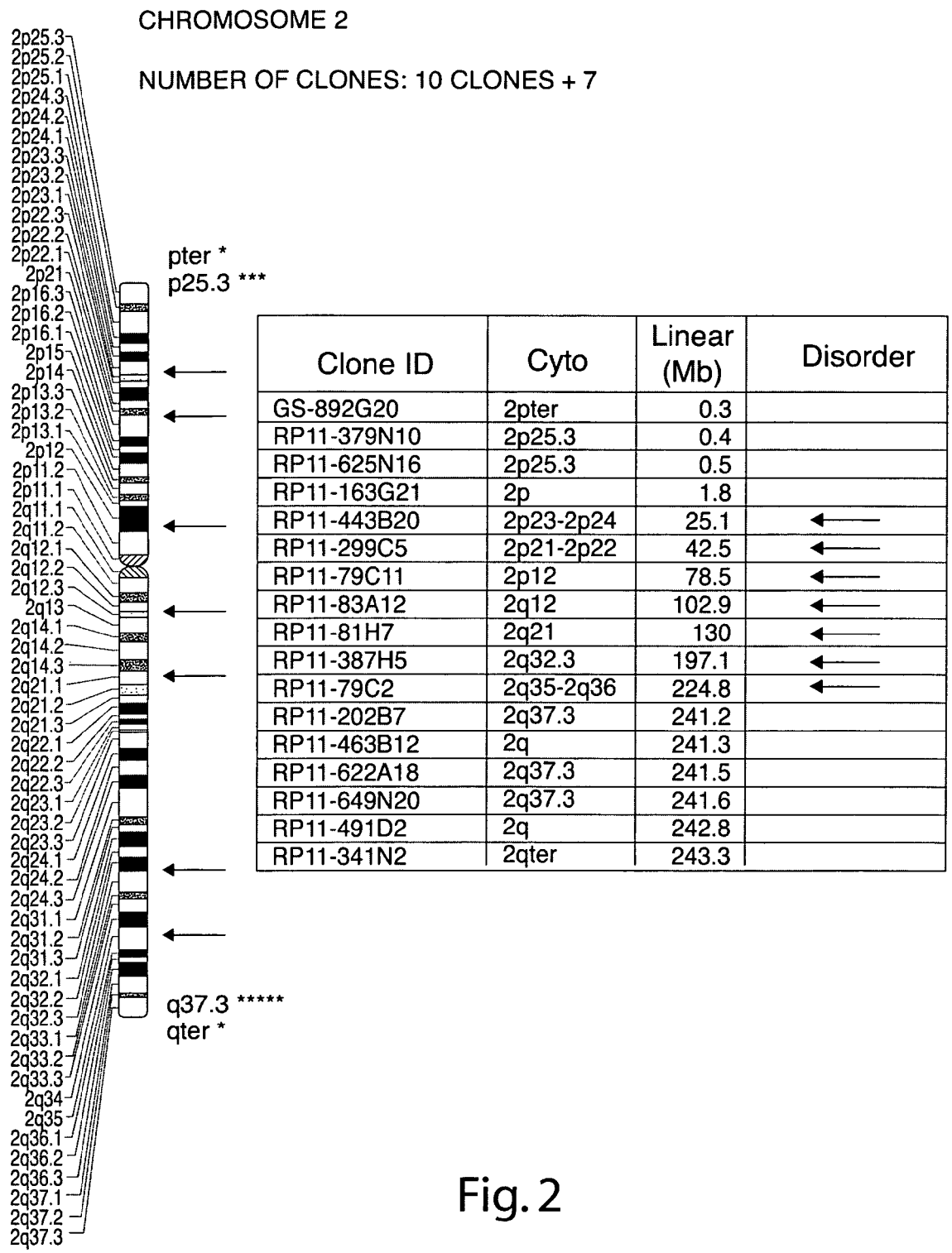

In FIG. 2 is seen an ideogram of chromsome 2. On the right side of the ideogram and in the table are listed two BAC clones carrying nucleic acid sequences corresponding to a syndrom known as 2p25.3, and four clones associated with a syndrome known as 2q37.3, which are named known chromosomal disorders that are associated with known areas of chromosome 2.

Also shown are seven clones carrying portions of chromosome 2 that are not associated with known chromosomal disorders (leftward pointing arrows). Further, some of these clones are closely linked to the centromere of chromosome 2, which is indicated by the constriction in the ideogram between 2p11 and 2q11. Microarrays were prepared on glass slides having DNA from the listed BAC clones in FIG. 2 that contain these loci on chromosome 2, and the slides further had two copies of each of the microarrays.

Example 3

Analysis of Chromosomal Disorders on Human Chromosome 3

Figure 3:
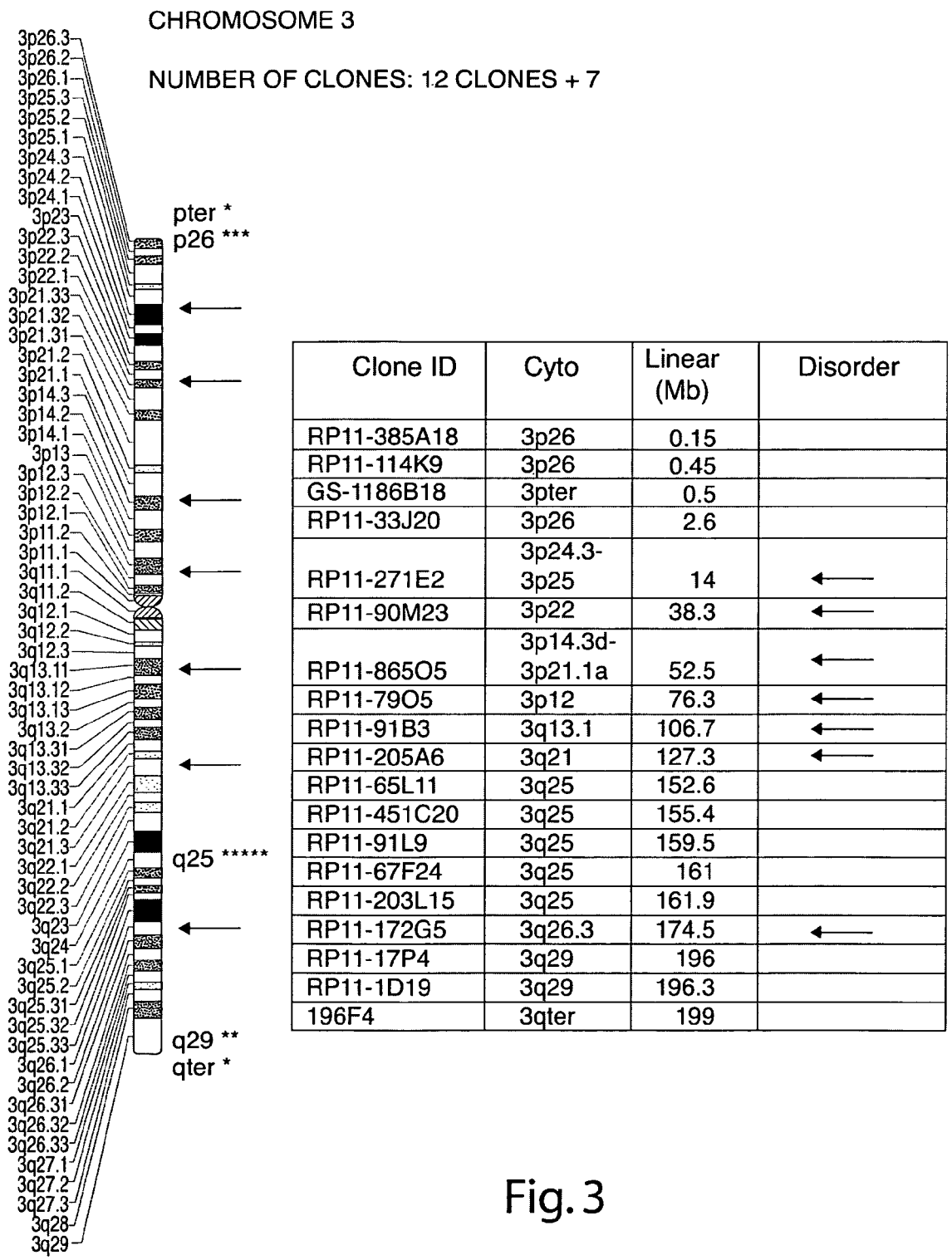

In FIG. 3 is seen an ideogram of chromsome 3. On the right side of the ideogram and in the table are listed four BAC clones carrying nucleic acid sequences corresponding to a syndrome known as 3p26, and five clones associated with a syndrome known as 3q25, and two clones associated with 3q29, which are named for known chromosomal disorders that are associated with known areas of chromosome 3.

Also shown are seven clones carrying portions of chromosome 3 that are not associated with known chromosomal disorders (leftward pointing arrows). Further, some of these clones are closely linked to the centromere of chromosome 3, which is indicated by the constriction in the ideogram between 3p11 and 3q11. Microarrays were prepared on glass slides having DNA from the listed BAC clones in FIG. 3 that contain these loci on chromosome 3, and the slides further had two copies of each of the microarrays.

Example 4

Analysis of Chromosomal Disorders on Human Chromosome 4

Figure 4:
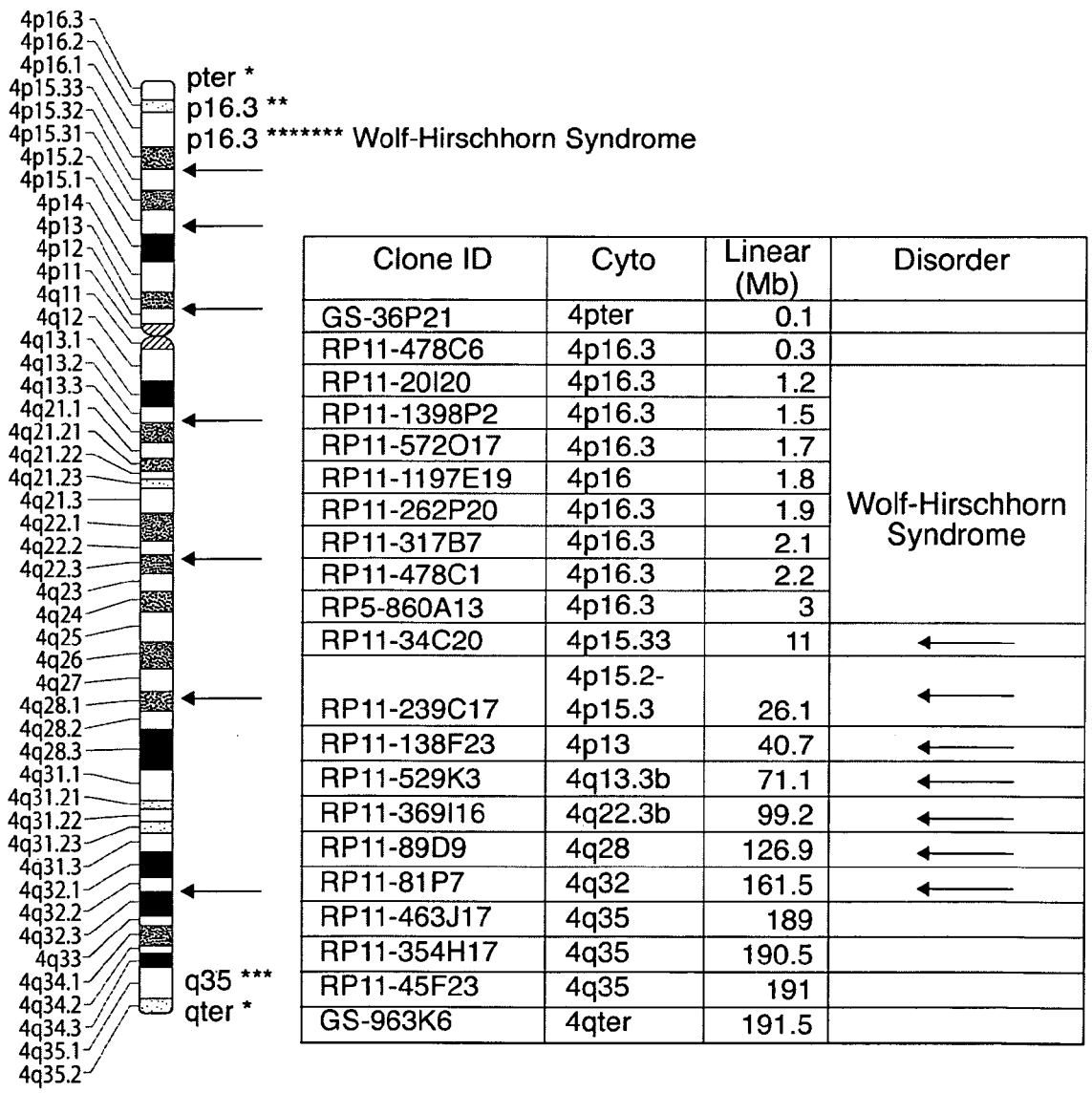

In FIG. 4 is seen an ideogram of chromsome 4. On the right side of the ideogram and in the table are listed ten BAC clones carrying nucleic acid sequences corresponding to locus 4p16, some of which are associated with a syndrome known as Wolf-Hirschhom syndrome, and sev clones associated with a syndrome known as 3q25, and two clones associated with 4q35, which are named for known chromosomal disorders that are associated with known areas of chromosome 4.

Also shown are seven clones carrying portions of chromosome 4 that are not associated with known chromosomal disorders (leftward pointing arrows). Further, some of these clones are closely linked to the centromere of chromosome 4, which is indicated by the constriction in the ideogram between 4p11 and 4q11. Microarrays were prepared on glass slides having DNA from the listed BAC clones in FIG. 4 that contain these loci on chromosome 4, and the slides further had two copies of each of the microarrays.

Example 5

Analysis of Chromosomal Disorders on Human Chromosome 5

Figure 5:
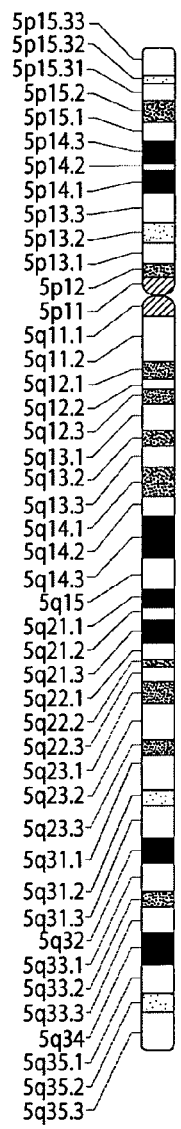

In FIG. 5 is seen an ideogram of chromsome 5. On the right side of the ideogram and in the table are listed ten BAC clones carrying nucleic acid sequences corresponding to locus 5p15, some of which are associated with a syndrome known as Cri-du-Chat syndrome, and seven clones associated with a syndrome at locus 5q35 known as Sotos Syndrom+C92s, which are known chromosomal disorders that are associated with known areas of chromosome 5.

Also shown are seven clones carrying portions of chromosome 5 that are not associated with known chromosomal disorders (leftward pointing arrows). Further, some of these clones are closely linked to the centromere of chromosome 5, which is indicated by the constriction in the ideogram between 5p11 and 5q11. Microarrays were prepared on glass slides having DNA from the listed BAC clones in FIG. 5 that contain these loci on chromosome 5, and the slides further had two copies of each of the microarrays.

Example 6

Analysis of Chromosomal Disorders on Human Chromosome 6

Figure 6:
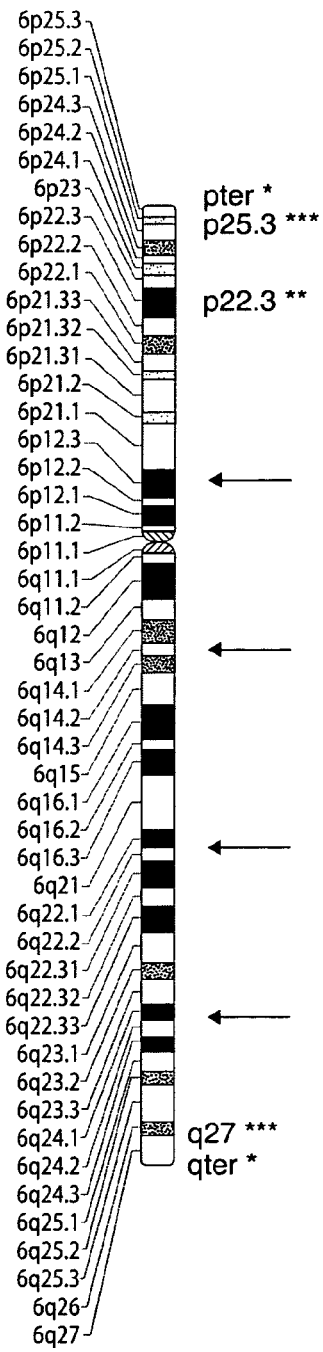

In FIG. 6 is seen an ideogram of chromsome 6. On the right side of the ideogram and in the table are listed ten BAC clones carrying nucleic acid sequences corresponding to locus 6p25, which are associated with a syndrome, and three clones associated with a syndrome at locus 6q27, which are known chromosomal disorders that are associated with known areas of chromosome 6.

Also shown are four clones carrying portions of chromosome 6 that are not associated with known chromosomal disorders (leftward pointing arrows). Further, some of these clones are closely linked to the centromere of chromosome 6, which is indicated by the constriction in the ideogram between 6p11 and 6q11. Microarrays were prepared on glass slides having DNA from the listed BAC clones in FIG. 6 that contain these loci on chromosome 6, and the slides further had two copies of each of the microarrays.

Example 7

Analysis of Chromosomal Disorders on Human Chromosome 7

Figure 7:
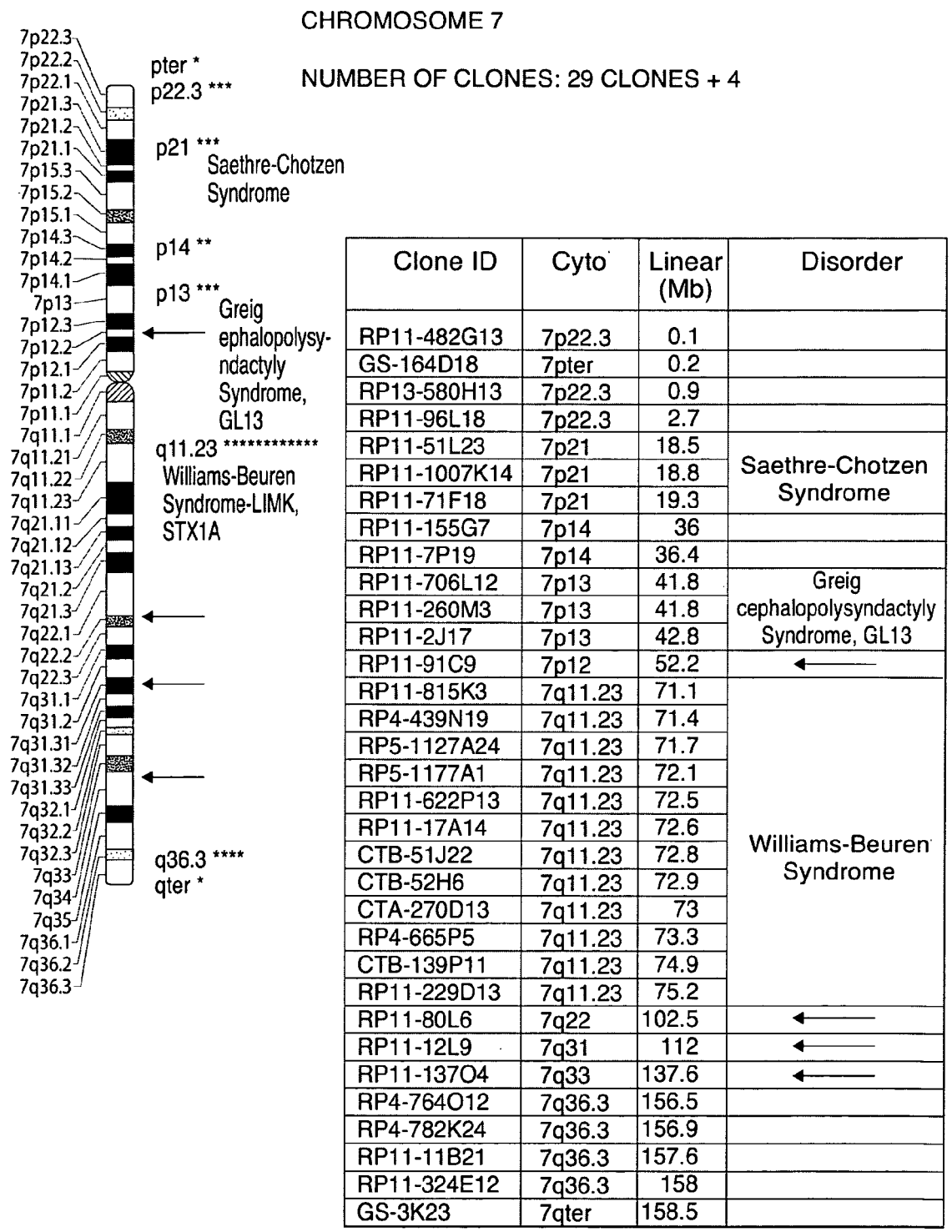

In FIG. 7 is seen an ideogram of chromsome 7. On the right side of the ideogram and in the table are listed five BAC clones carrying nucleic acid sequences corresponding to locus 7p22.3 and 7p21, three of which are associated with a syndrome known as Saethre-Chotzen Syndrom, and three clones associated with a syndrome at locus 7p13 known as Greig cephelopolysyndactyly syndrome, and 13 clones associated with 7q11.23 associated with Williams-Beuren syndrom, and four clones associated with locus 7q36.3, which are known chromosomal disorders that are associated with known areas of chromosome 7.

Also shown are four clones carrying portions of chromosome 7 that are not associated with known chromosomal disorders (leftward pointing arrows). Further, one of these clones are closely linked to the centromere of chromosome 7, which is indicated by the constriction in the ideogram between 7p11 and 7q11. Microarrays were prepared on glass slides having DNA from the listed BAC clones in FIG. 7 that contain these loci on chromosome 7, and the slides further had two copies of each of the microarrays.

Example 8

Analysis of Chromosomal Disorders on Human Chromosome 8

Figure 8:
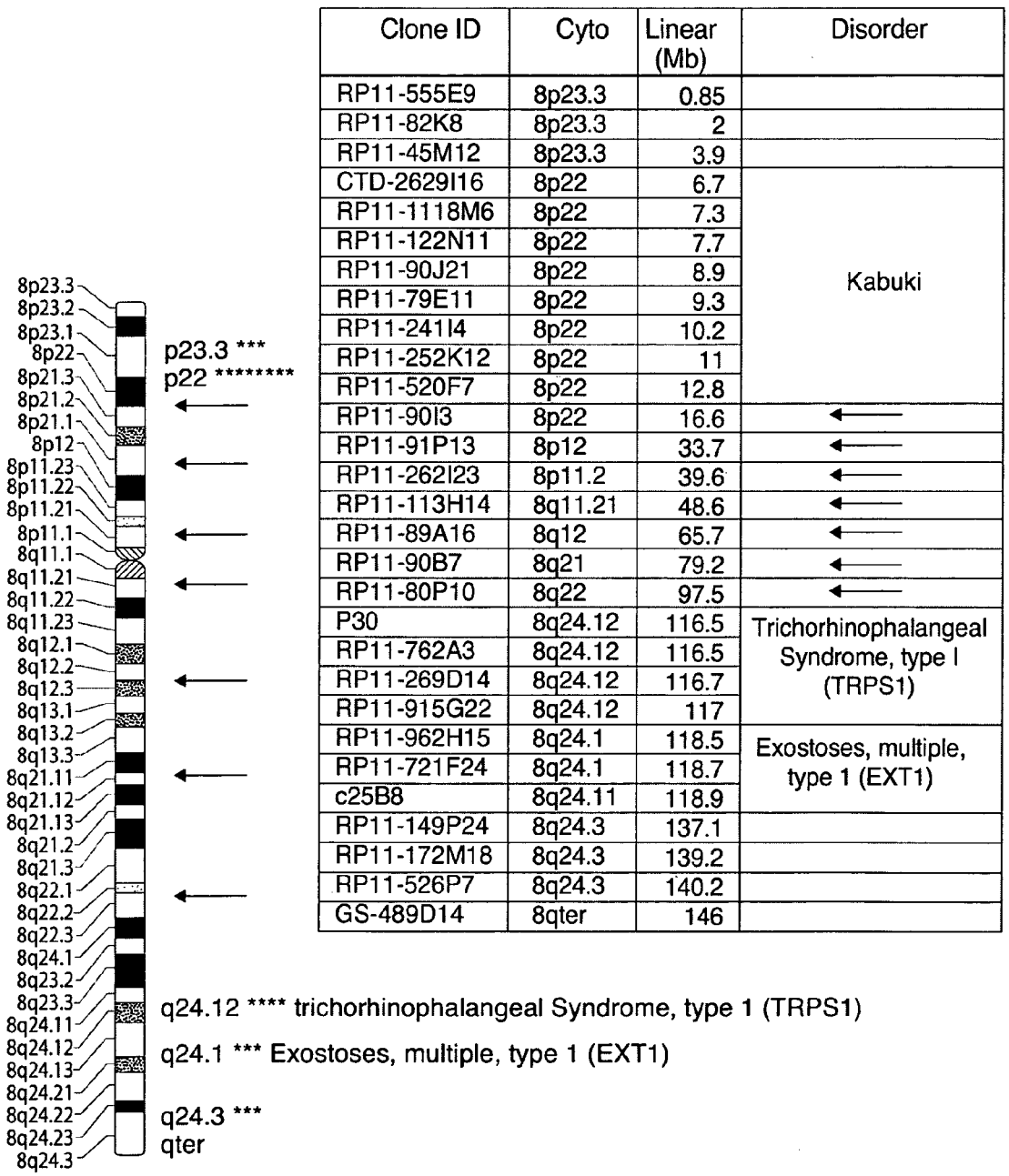

In FIG. 8 is seen an ideogram of chromsome 8. On the right side of the ideogram and in the table are listed eight BAC clones carrying nucleic acid sequences corresponding to locus 8p22, which are associated with a syndrome known as Kabuki syndrome, and four clones associated with a syndrome at locus 8q24.12 associated with Trichorhinophalangeal Syndrome type 1 (TRPS1), and three clones associated with 8q24.12 associated with Exotoses, multiple, type 1 (EXT1) syndrome, and three clones associated with locus 8q24.3, which are known chromosomal disorders that are associated with known areas of chromosome 8.

Also shown are seven clones carrying portions of chromosome 8 that are not associated with known chromosomal disorders (leftward pointing arrows). Further, some of these clones are closely linked to the centromere of chromosome 8, which is indicated by the constriction in the ideogram between 8p11 and 8q11. Microarrays were prepared on glass slides having DNA from the listed BAC clones in FIG. 8 that contain these loci on chromosome 8, and the slides further had two copies of each of the microarrays.

Example 9

Analysis of Chromosomal Disorders on Human Chromosome 9

Figure 9:
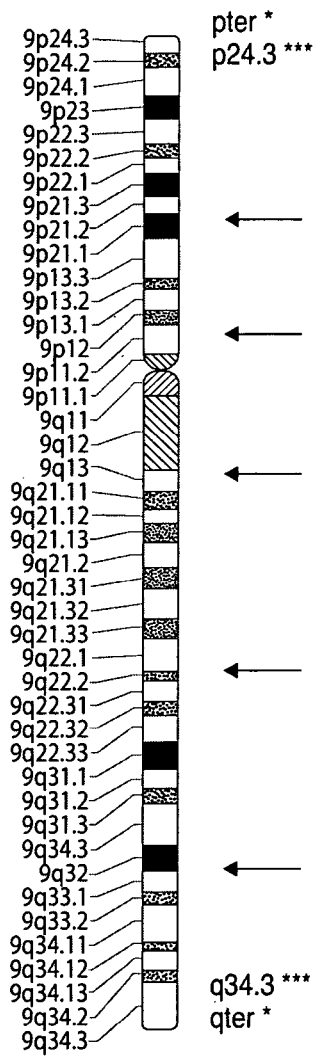

In FIG. 9 is seen an ideogram of chromsome 9. On the right side of the ideogram and in the table are listed three BAC clones carrying nucleic acid sequences corresponding to locus 9p24.3, and three clones associated with a syndrome at locus 9q34.3, which are known chromosomal disorders that are associated with known areas of chromosome 9.

Also shown are five clones carrying portions of chromosome 9 that are not associated with known chromosomal disorders (leftward pointing arrows). Further, some of these clones are closely linked to the centromere of chromosome 9, which is indicated by the constriction in the ideogram between 9p11 and 9q11. Microarrays were prepared on glass slides having DNA from the listed BAC clones in FIG. 9 that contain these loci on chromosome 9, and the slides further had two copies of each of the microarrays.

Example 10

Analysis of Chromosomal Disorders on Human Chromosome 10

Figure 10:
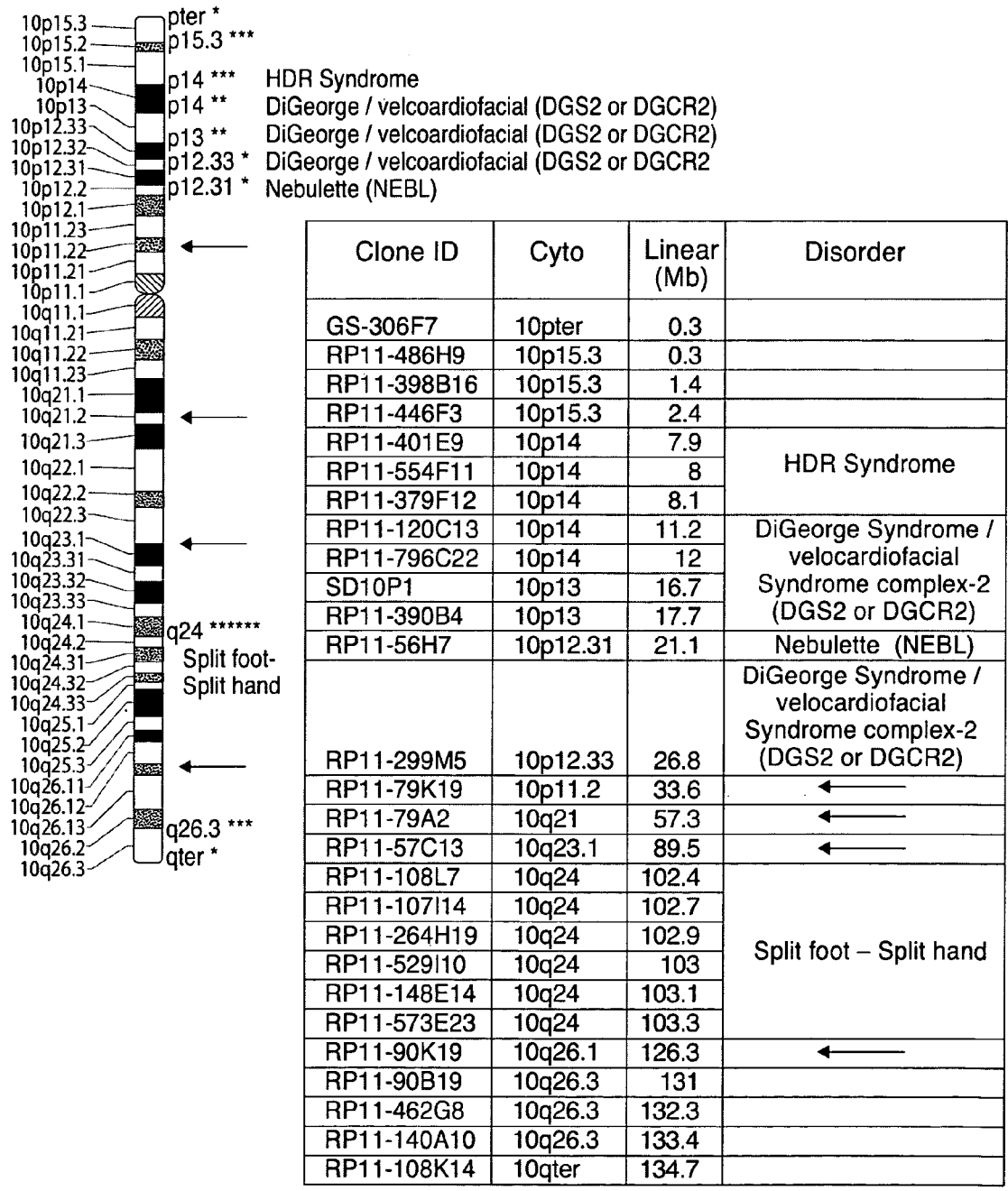

In FIG. 10 is seen an ideogram of chromsome 10. On the right side of the ideogram and in the table are listed three BAC clones carrying nucleic acid sequences corresponding to locus 10p15.3, and three clones associated with a syndrome at locus 10p14 known as HDR syndrome, and five clones associated with a syndrome between loci 10p14 and 10p13 known as DiGeorge Syndrome/velocardiofacial Syndrome complex-2 (DGS2 or DGCR2), and one clone at locus 10p12.31 known as Nebulette (NEBL), and one clone at locus 10p12.33 associated with DGS2 or DGCR2 syndrome, and six lones associated with locus 10q24 known as Split foot-Split Hand syndrome, and three clones at locus 10q26.3, which are known chromosomal disorders that are associated with known areas of chromosome 10.

Also shown are four clones carrying portions of chromosome 10 that are not associated with known chromosomal disorders (leftward pointing arrows). Further, two of these clones are closely linked to the centromere of chromosome 10, which is indicated by the constriction in the ideogram between 10p11 and 10q11. Microarrays were prepared on glass slides having DNA from the listed BAC clones in FIG. 10 that contain these loci on chromosome 10, and the slides further had two copies of each of the microarrays.

Example 11

Analysis of Chromosomal Disorders on Human Chromosome 11

Figure 11:
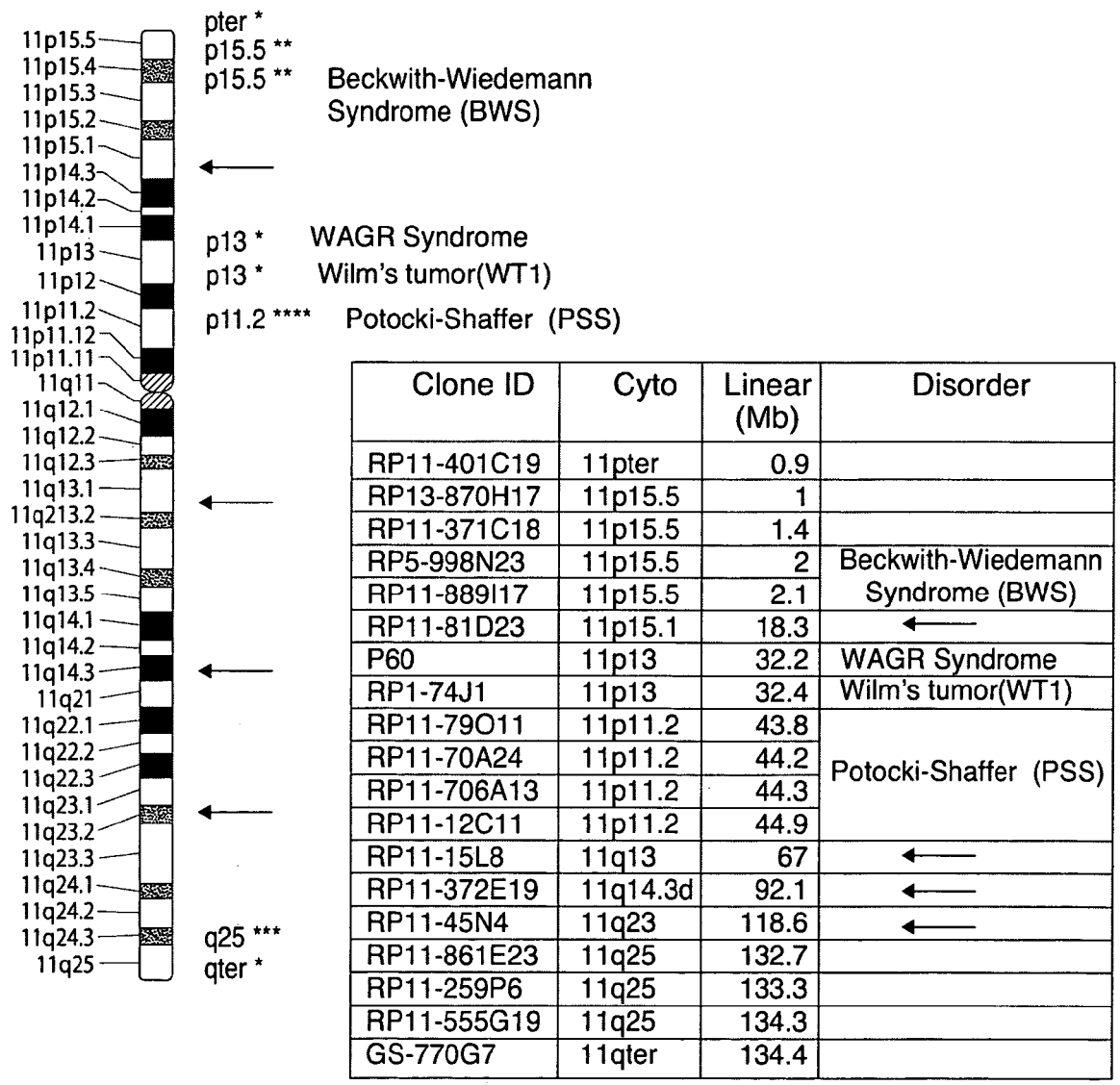

In FIG. 11 is seen an ideogram of chromsome 11. On the right side of the ideogram and in the table are listed four BAC clones carrying nucleic acid sequences corresponding to locus 11p15.5, two of which are associated with Beckwith-Wiedemann Syndrome (BWS), and one clone associated with WAGR syndrome at locus 11p13, and one clone associated with Wilm's Tumor syndrome at locus 11p13, and four clones associated with a syndrome at locus 11p11.2 known as Potocki-Shaffer Syndrome (PSS), and three clones at locus 11q25, which are known chromosomal disorders that are associated with known areas of chromosome 11.

Also shown are four clones carrying portions of chromosome 11 that are not associated with known chromosomal disorders (leftward pointing arrows). Further, one of these clones isclosely linked to the centromere of chromosome 11, which is indicated by the constriction in the ideogram between 11p11 and 11q11. Microarrays were prepared on glass slides having DNA from the listed BAC clones in FIG. 11 that contain these loci on chromosome 11, and the slides further had two copies of each of the microarrays.

Example 12

Analysis of Chromosomal Disorders on Human Chromosome 12

Figure 12:
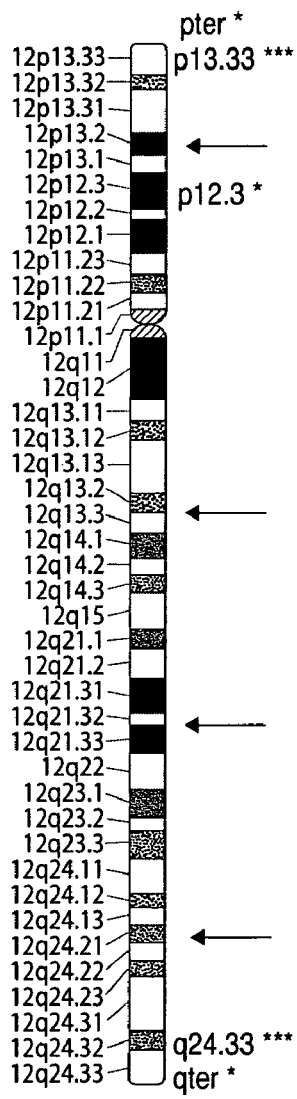

In FIG. 12 is seen an ideogram of chromsome 12. On the right side of the ideogram and in the table are listed four BAC clones carrying nucleic acid sequences corresponding to portions of the chromosome between loci 12p13.33 and 12p13.32, and three clones at locus 12q24.33, which are known chromosomal disorders that are associated with known areas of chromosome 12.

Also shown are four clones carrying portions of chromosome 12 that are not associated with known chromosomal disorders (leftward pointing arrows). Further, one of these clones is closely linked to the centromere of chromosome 12, which is indicated by the constriction in the ideogram between 12p11 and 12q11. Microarrays were prepared on glass slides having DNA from the listed BAC clones in FIG. 12 that contain these loci on chromosome 12, and the slides further had two copies of each of the microarrays.

Example 13

Analysis of Chromosomal Disorders on Human Chromosome 13

Figure 13:
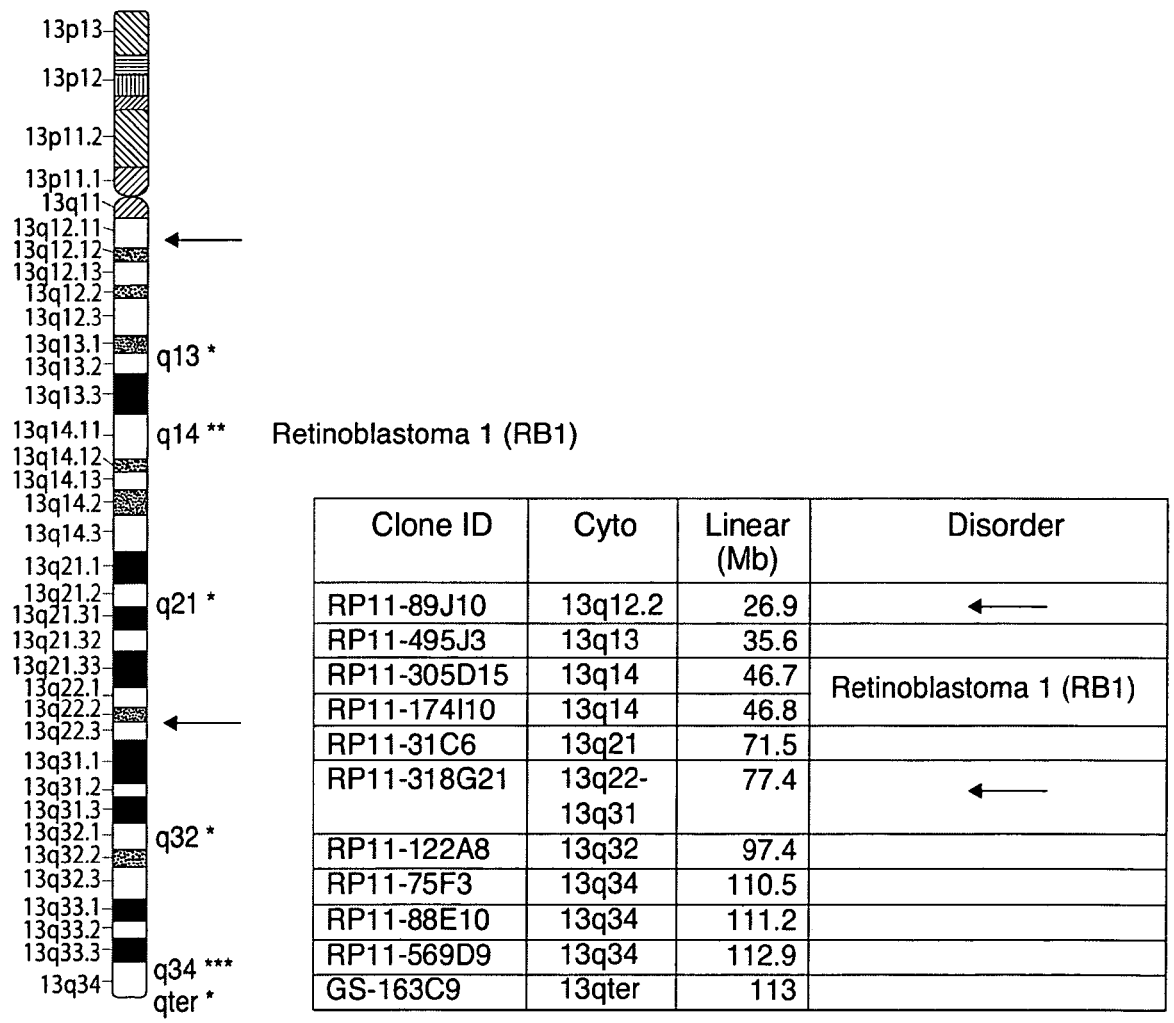

In FIG. 13 is seen an ideogram of chromsome 13. On the right side of the ideogram and in the table are listed two BAC clones carrying nucleic acid sequences corresponding to portions of the chromosome at locus 13q14 and associated with retinoblastoma 1 (RB 1), and four clones associated with loci between 13q32 and 13q34, which are known chromosomal disorders that are associated with known areas of chromosome 13.

Also shown are two clones carrying portions of chromosome 13 that are not associated with known chromosomal disorders (leftward pointing arrows). Further, one of these clones is closely linked to the centromere of chromosome 13, which is indicated by the constriction in the ideogram between 13p11 and 13q11. Microarrays were prepared on glass slides having DNA from the listed BAC clones in FIG. 13 that contain these loci on chromosome 13, and the slides further had two copies of each of the microarrays.

Example 14

Analysis of Chromosomal Disorders on Human Chromosome 14

Figure 14:
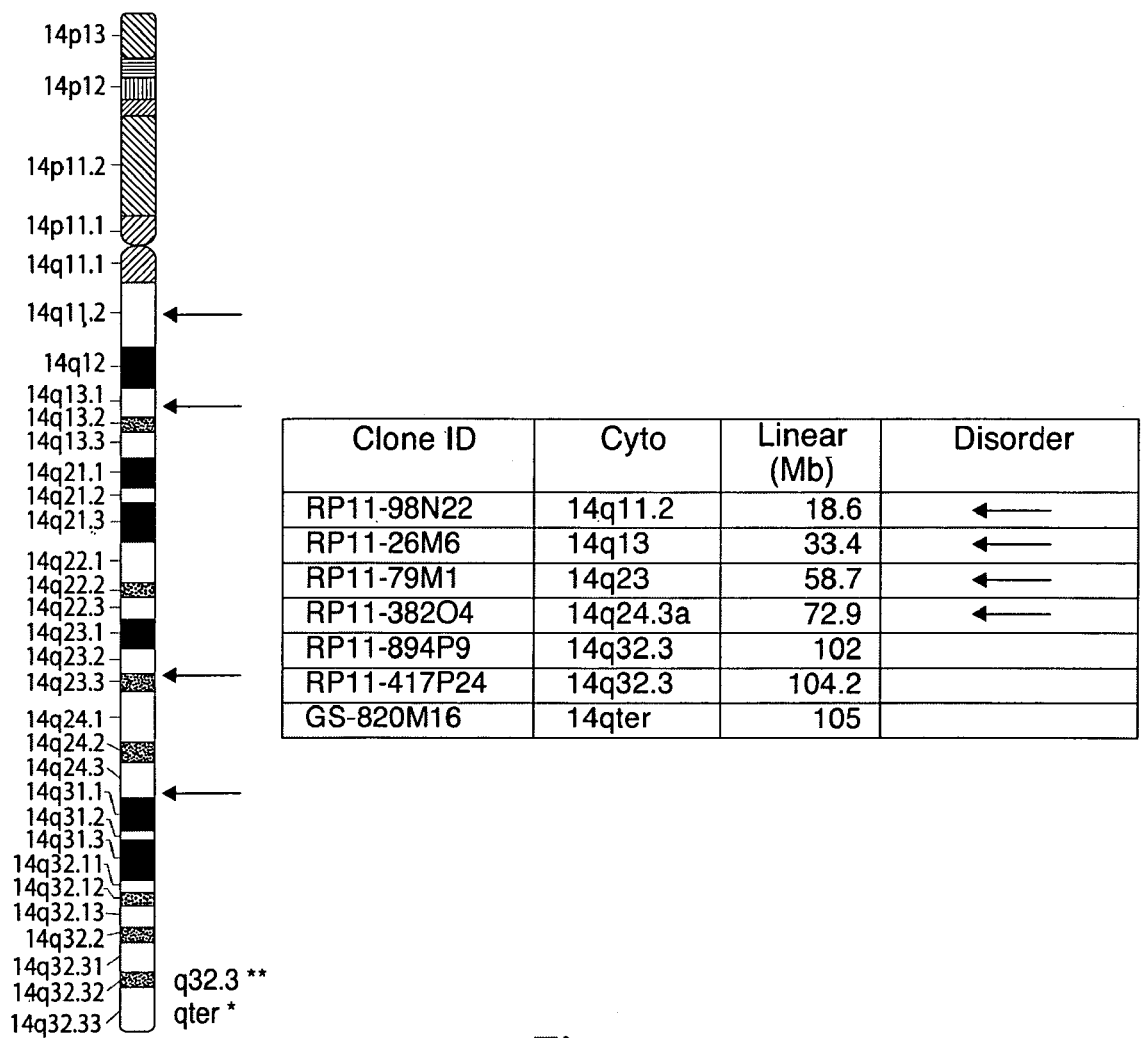

In FIG. 14 is seen an ideogram of chromsome 14. On the right side of the ideogram and in the table are listed two BAC clones carrying nucleic acid sequences corresponding to portions of the chromosome at locus 14q24.3 and associated with known chromosomal disorders that are associated with known areas of chromosome 14.

Also shown are four clones carrying portions of chromosome 14 that are not associated with known chromosomal disorders (leftward pointing arrows). Further, one of these clones is closely linked to the centromere of chromosome 14, which is indicated by the constriction in the ideogram between 14p11 and 14q11. Microarrays were prepared on glass slides having DNA from the listed BAC clones in FIG. 14 that contain these loci on chromosome 14, and the slides further had two copies of each of the microarrays.

Example 15

Analysis of Chromosomal Disorders on Human Chromosome 15

Figure 15:
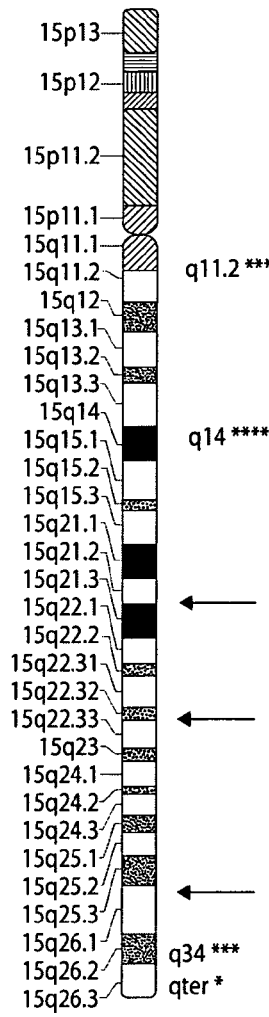

In FIG. 15 is seen an ideogram of chromsome 15. On the right side of the ideogram and in the table are listed six BAC clones carrying nucleic acid sequences corresponding to portions of the chromosome at locus 15p11.2 and associated with known chromosomal disorder Prader-Willi Syndrome (PWS)/Angelman Region (AR), and three clones at locus 15p14, and one clone at locus 15q11.2 and associated with known chromosomal disorder Prader-Willi Syndrome (PWS)/Angelman Region (AR), and one additional clone at 15q14, and three clones at 15q34, that are associated with known areas of chromosome 14.

Also shown are three clones carrying portions of chromosome 15 that are not associated with known chromosomal disorders (leftward pointing arrows). Microarrays were prepared on glass slides having DNA from the listed BAC clones in FIG. 15 that contain these loci on chromosome 15, and the slides further had two copies of each of the microarrays.

Example 16

Analysis of Chromosomal Disorders on Human Chromosome 16

In FIG. 16 is seen an ideogram of chromsome 16. On the right side of the ideogram and in the table are listed two BAC clones carrying nucleic acid sequences corresponding to portions of the chromosome at locus 16p13.3, and three more clones associated with this locus and also associated with known chromosomal disorder Tuberous sclerosis-2 (TSC2)/Polycystic kidney disease adult type (PKD1), and four clones at locus 16p13.3 associated with Rubinstein-Taybi Syndrome (RTS), and three clones carrying portions of DNA from between loci 16q24.2 and 16q24.3, associated with known chromosomal disorders associated with known areas of chromosome 16.

Also shown are five clones carrying portions of chromosome 16 that are not associated with known chromosomal disorders (leftward pointing arrows). Some of these are associated with regions of the chromosome hear the centromer. Microarrays were prepared on glass slides having DNA from the listed BAC clones in FIG. 16 that contain these loci on chromosome 16, and the slides further had two copies of each of the microarrays.

Example 17

Analysis of Chromosomal Disorders on Human Chromosome 17

Figure 17:
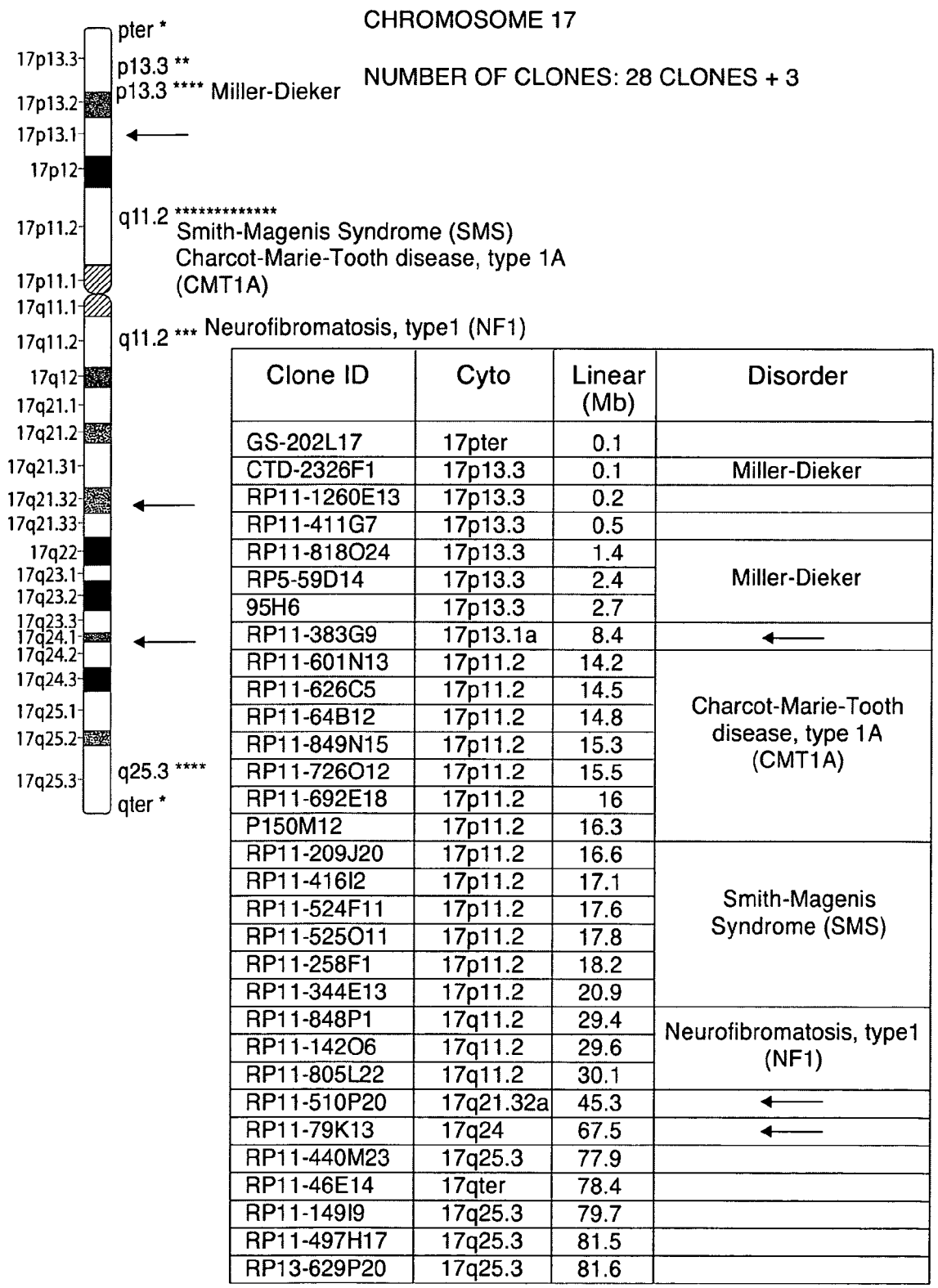

In FIG. 17 is seen an ideogram of chromsome 17. On the right side of the ideogram and in the table are listed six BAC clones carrying nucleic acid sequences corresponding to portions of the chromosome at locus 17p13.3, four of which associated with known chromosomal disorder Miller-Dieker Syndrome, and 16.clones at locus 17p11.2, seven of which are associated with Charcot-Marie-Tooth disease, type 1A (CMT1A), and six clones of which are associated with Smith-Magenis Syndrome (SMS). The ideogram and table further show three additional clones at 17q11.2 associated with Neurofibromatosis, type 1 (NF 1), and fove clones at 17q25.3, that are associated with known areas of chromosome 14 and known chromosomal disorders.

Also shown are three clones carrying portions of chromosome 17 that are not associated with known chromosomal disorders (leftward pointing arrows). Microarrays were prepared on glass slides having DNA from the listed BAC clones in FIG. 17 that contain these loci on chromosome 17, and the slides further had two copies of each of the microarrays.

Example 18

Analysis of Chromosomal Disorders on Human Chromosome 18

Figure 18:
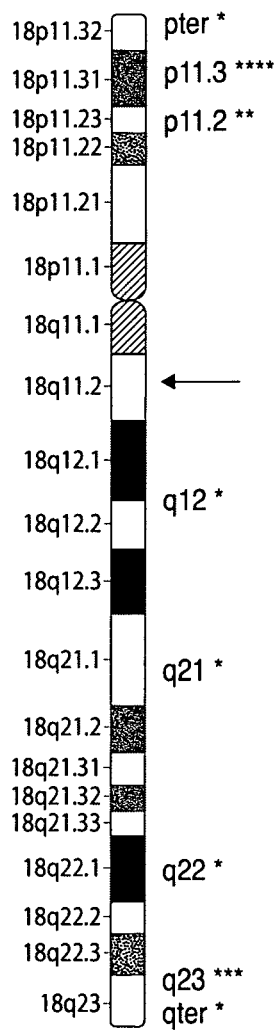

In FIG. 18 is seen an ideogram of chromsome 18. On the right side of the ideogram and in the table are listed six BAC clones carrying nucleic acid sequences corresponding to portions of the chromosome between loci 18p11.3 and 18p11.2, one clone at locus 18q12, and five clones between loci 18q21 and 18q23, which are associated with known areas of chromosome 18 and known chromosomal disorders.

Also shown is one clone carrying a portion of chromosome 18 that is not associated with known chromosomal disorders (leftward pointing arrows). Microarrays were prepared on glass slides having DNA from the listed BAC clones in FIG. 18 that contain these loci on chromosome 18, and the slides further had two copies of each of the microarrays.

Example 19

Analysis of Chromosomal Disorders on Human Chromosome 19

Figure 19:
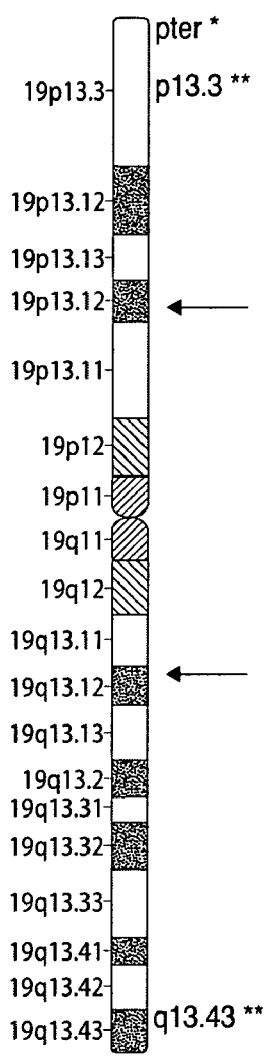

In FIG. 19 is seen an ideogram of chromsome 19. On the right side of the ideogram and in the table are listed two BAC clones carrying nucleic acid sequences corresponding to portions of the chromosome at locus 19p13.3, and two clones for portions of the chromosome between loci 19q13.4 and 19q13.43, which are associated with known areas of chromosome 19 and known chromosomal disorders.

Also shown are two clones carrying portions of chromosome 19 that are not associated with known chromosomal disorders (leftward pointing arrows). Microarrays were prepared on glass slides having DNA from the listed BAC clones in FIG. 19 that contain these loci on chromosome 19, and the slides further had two copies of each of the microarrays.

Example 20

Analysis of Chromosomal Disorders on Human Chromosome 20

Figure 20:
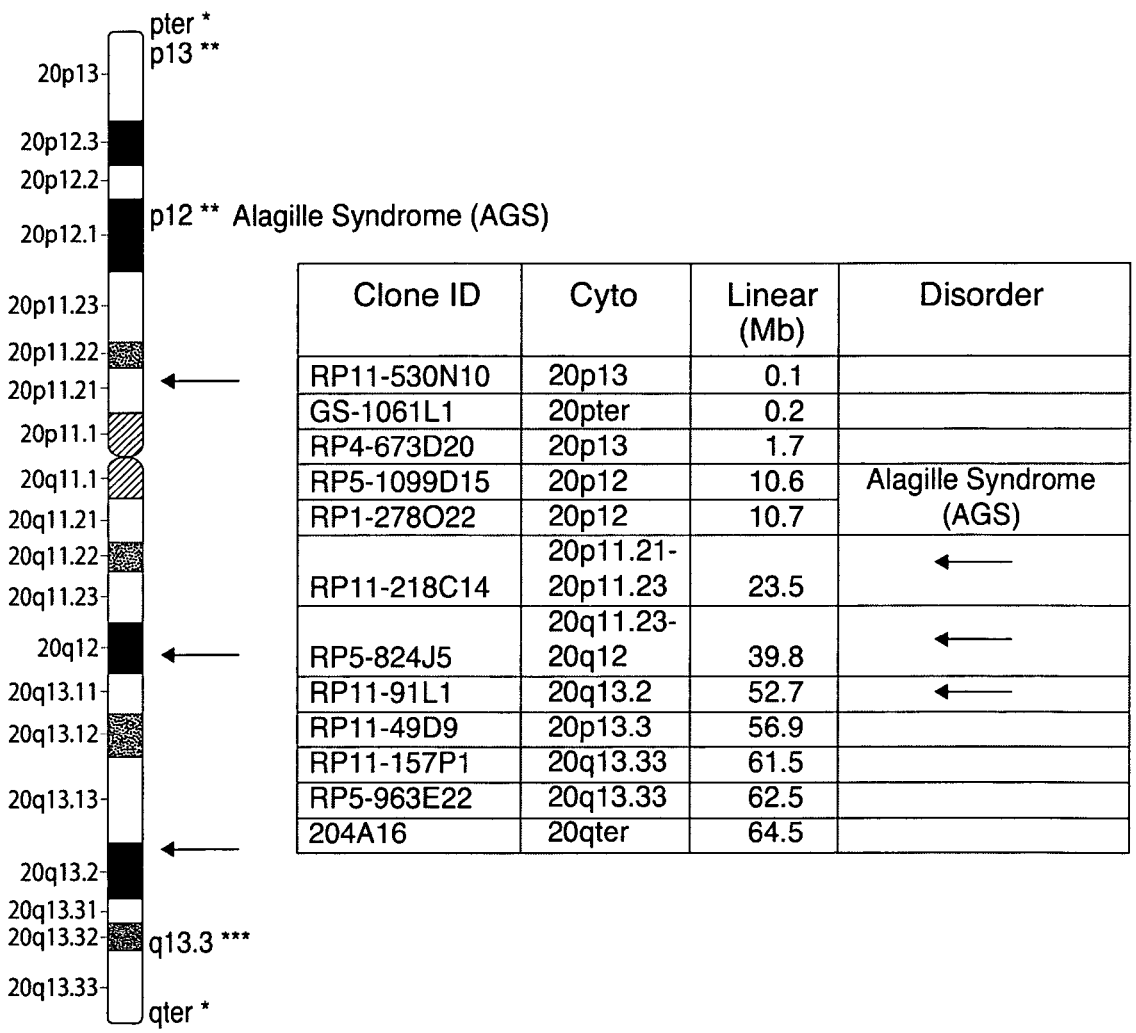

In FIG. 20 is seen an ideogram of chromsome 20. On the right side of the ideogram and in the table are listed two BAC clones carrying nucleic acid sequences corresponding to portions of the chromosome at locus 20p13, and two clones for portions of the chromosome at locus 19q13.4 and 20p12 that correspond to Alagille Syndrome (AGS), and three clones with portions of the choromosome from between loci 20q13.3 and 10q13.33, which are associated with known areas of chromosome 20 and known chromosomal disorders.

Also shown are three clones carrying portions of chromosome 20 that are not associated with known chromosomal disorders (leftward pointing arrows), one of which is closely linked to the centromere of chromosome 20. Microarrays were prepared on glass slides having DNA from the listed BAC clones in FIG. 20 that contain these loci on chromosome 20, and the slides further had two copies of each of the microarrays.

Example 21

Analysis of Chromosomal Disorders on Human Chromosome 21

Figure 21:
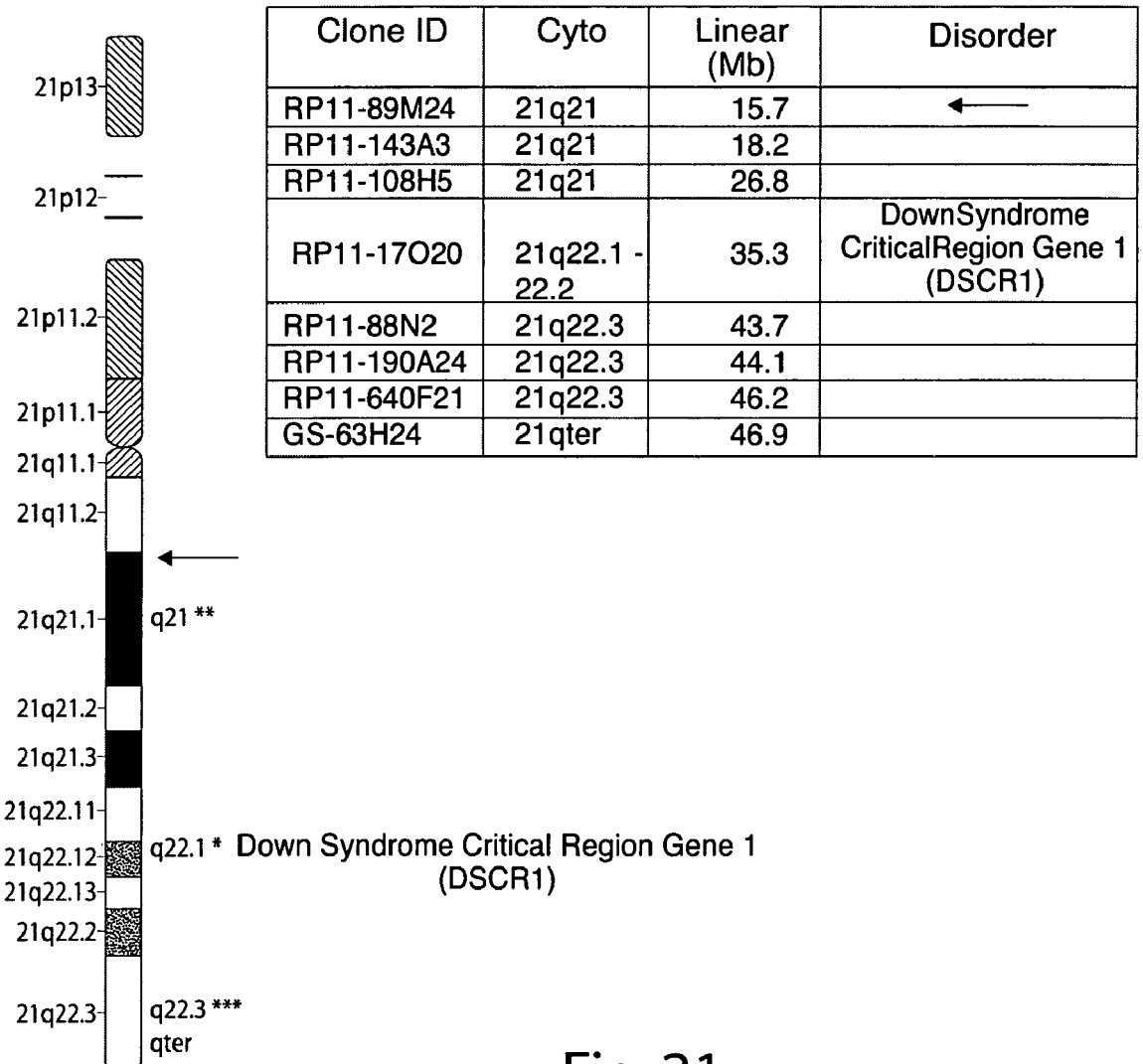

In FIG. 21 is seen an ideogram of chromsome 21. On the right side of the ideogram and in the table are listed six BAC clones carrying nucleic acid sequences corresponding to portions of the chromosome between loci 21q21 and 21q22.3, one of which is associated with Down Syndrome Critical Region Gene 1 (DSCR1), and which are associated with known areas of chromosome 21 and known chromosomal disorders, particularly Down Syndrome.

Also shown is one clone carrying a portion of chromosome 21 that is not associated with known chromosomal disorders (leftward pointing arrows), and which is closely linked to the centromere of chromosome 21. Microarrays were prepared on glass slides having DNA from the listed BAC clones in FIG. 21 that contain these loci on chromosome 21, and the slides further had two copies of each of the microarrays.

Example 22

Analysis of Chromosomal Disorders on Human Chromosome 22

Figure 22:
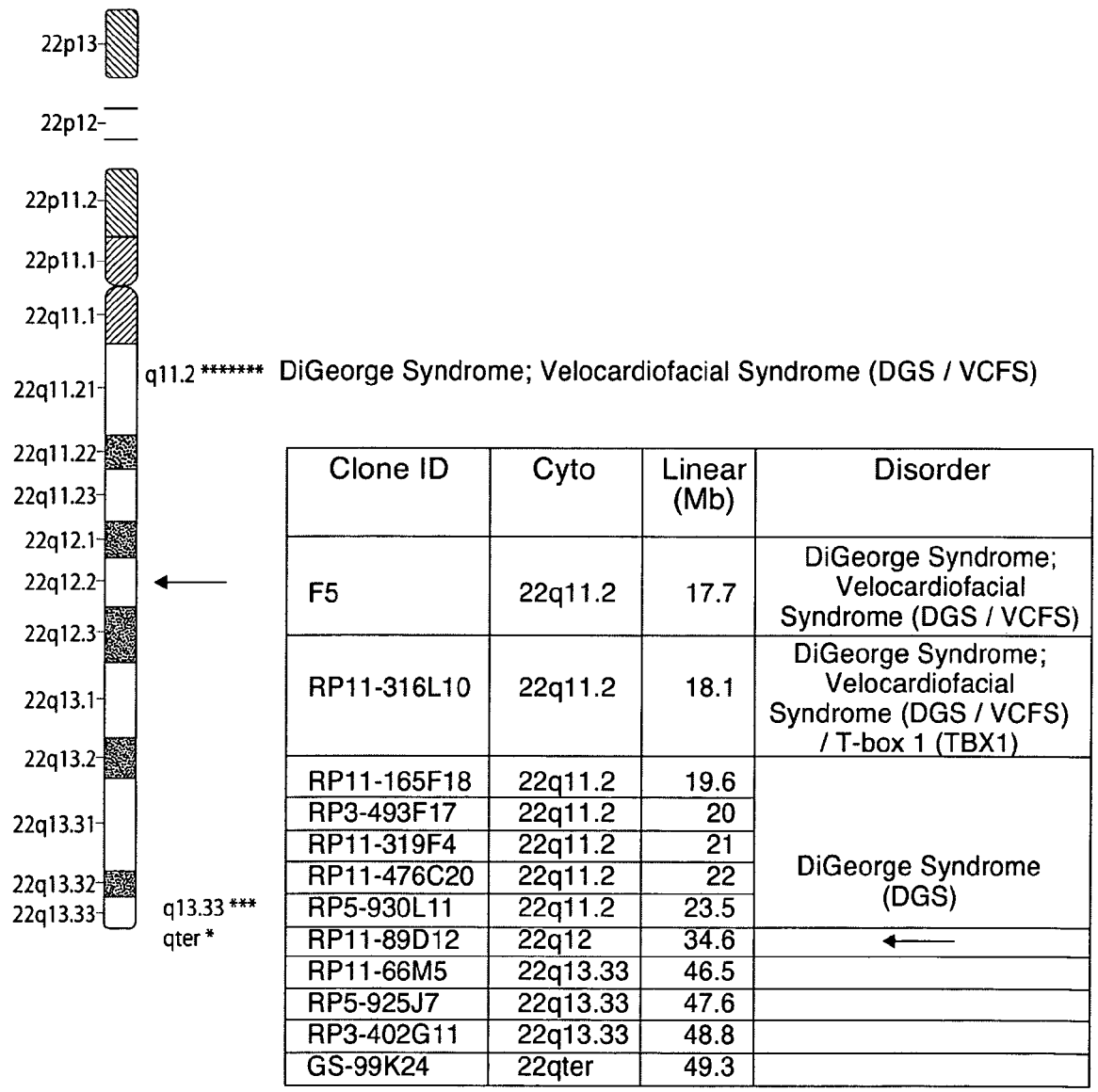

In FIG. 22 is seen an ideogram of chromsome 22. On the right side of the ideogram and in the table are listed eleven BAC clones carrying nucleic acid sequences corresponding to portions of the chromosome between loci 22q11.2 and 22q13.33, one of which is associated with DiGeorge Syndrome Velocardiofacial Syndrome (DGS/VCFS), one of which is associated with DiGeorge Syndrome Velocardiofacial Syndrome (DGS/VCFS)/T-box 1 (TBX1), and five of which are associated with DiGeorge Syndrome (DGS). Further, four clones contain portions of chromosome 22 at locus 22q13.33 and are associated with chromosomal disorders at this site.

Also shown is one clone carrying a portion of chromosome 22 that is not associated with known chromosomal disorders (leftward pointing arrows). Microarrays were prepared on glass slides having DNA from the listed BAC clones in FIG. 22 that contain these loci on chromosome 22, and the slides further had two copies of each of the microarrays.

Example 23

Analysis of Chromosomal Disorders on Human Chromosome X

Figure 23A:
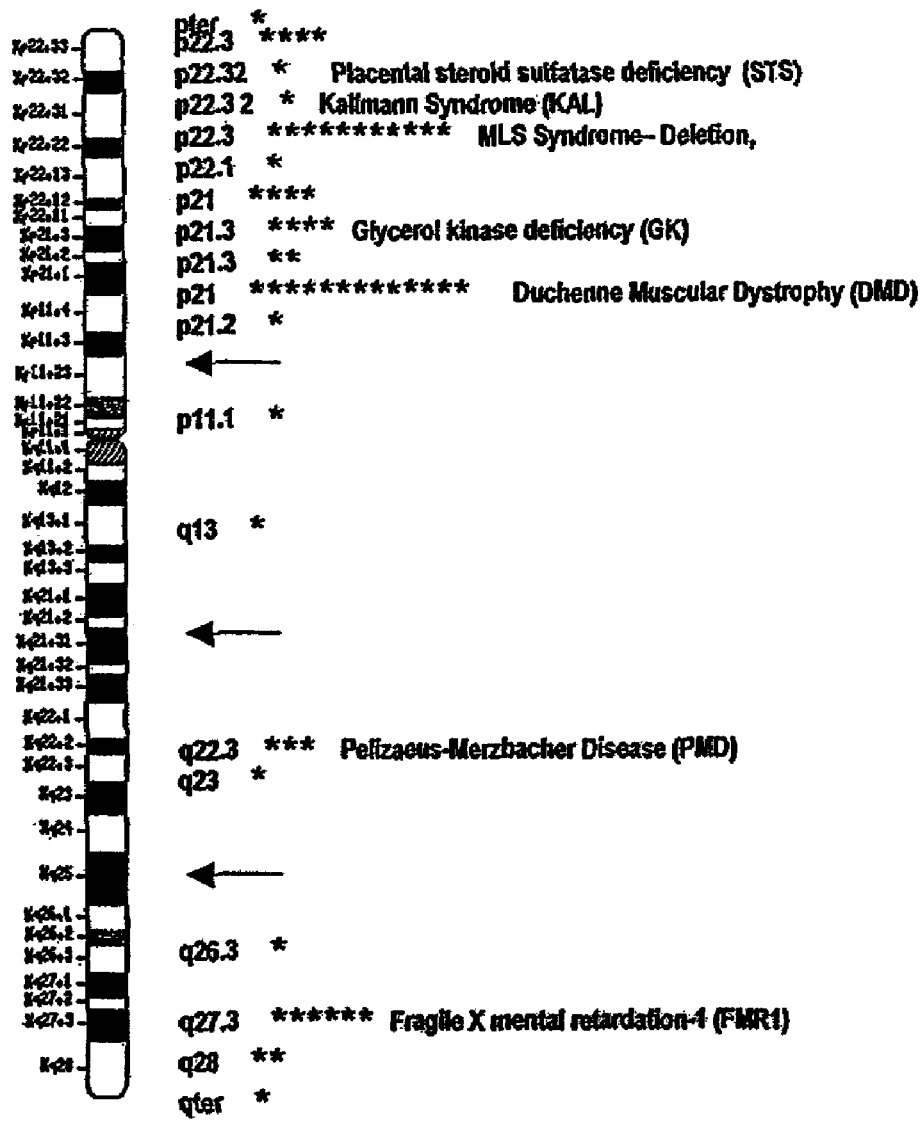
FIG. 23A is a drawing of human chromosome X, with arms, loci, positions and clones marked as indicated for FIG. 1.

In FIG. 23A is seen an ideogram of chromsome X. On the right side of the ideogram and in the table of FIG. 23B are listed 59 BAC clones carrying nucleic acid sequences corresponding to portions of the chromosome between loci Xp22.33 and Xq27.3. These clones are associated with a large number of chromosomal disorders, including: Placental steroid sulfatase deficiency (STS) at locus Xp22.32; Kallmann Syndrome (KAL) at locus Xp22.32; MLS syndrome deletion at loci Xp22.22 and locus Xp22.32; Glycerol Kinase deficiency at locus Xp21.3; Glycerol Kinase deficiency/Adrenal hypoplasia, congenital (AHC) also at locus Xp21.3; Duchenne Muscular Dystrophy (DMD) from locus Xp21.3 to Xp21.2; Pelizaeus-Merzbacher Disease (PMD) at locus Xq22.2; and Fragile X mental retardafion-1 (FMR1) at locus Xq27.3.

Also shown are three clones carrying portions of chromosome X that are not associated with known chromosomal disorders (leftward pointing arrows), one of which is closely linked to the centromere. Microarrays were prepared on glass slides having DNA from the listed BAC clones in FIGS. 23A-23B that contain these loci on chromosome X, and the slides further had two copies of each of the microarrays.

Example 24

Analysis of Chromosomal Disorders on Human Chromosome Y

Figure 24:
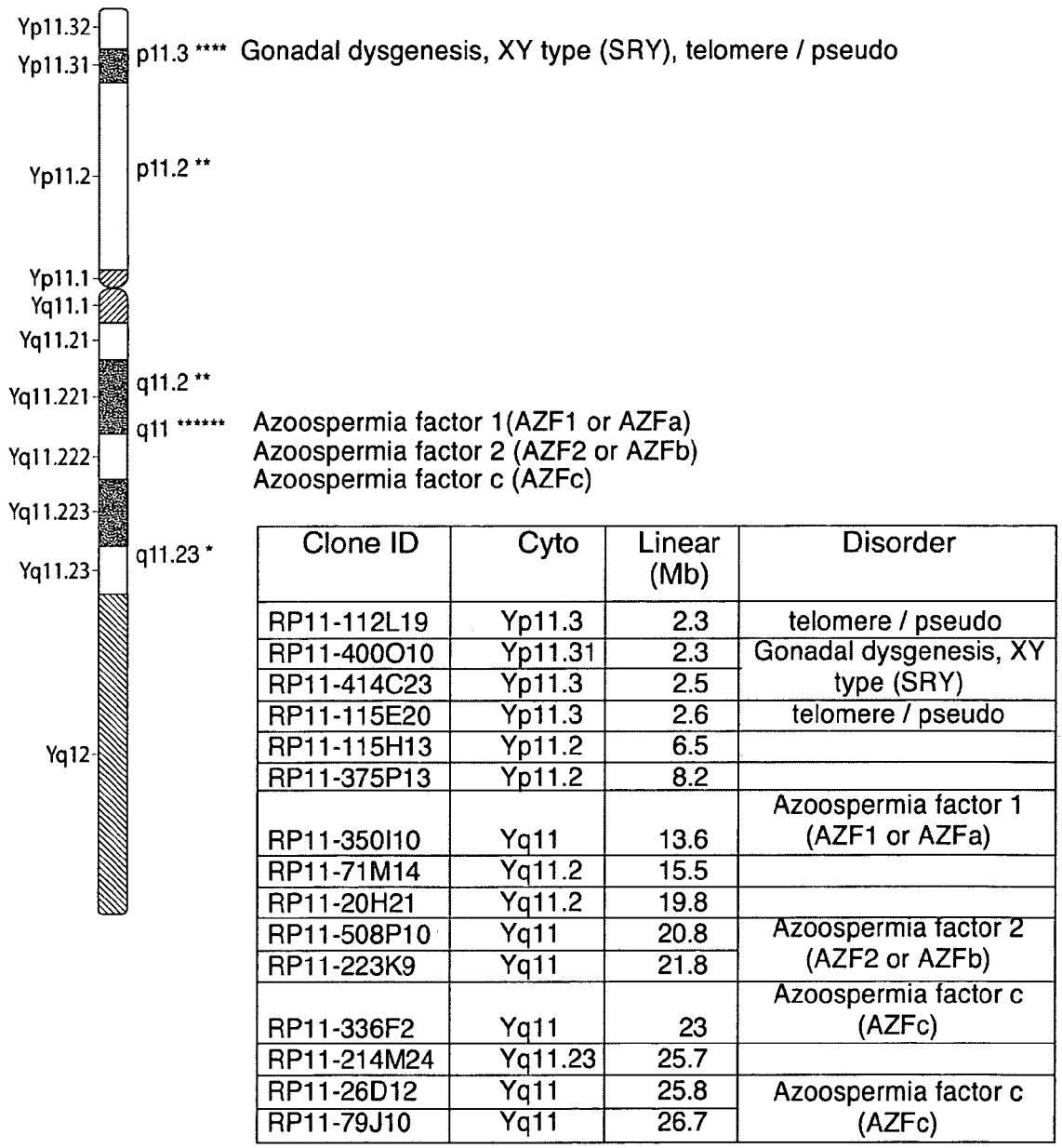
Figure 25A:
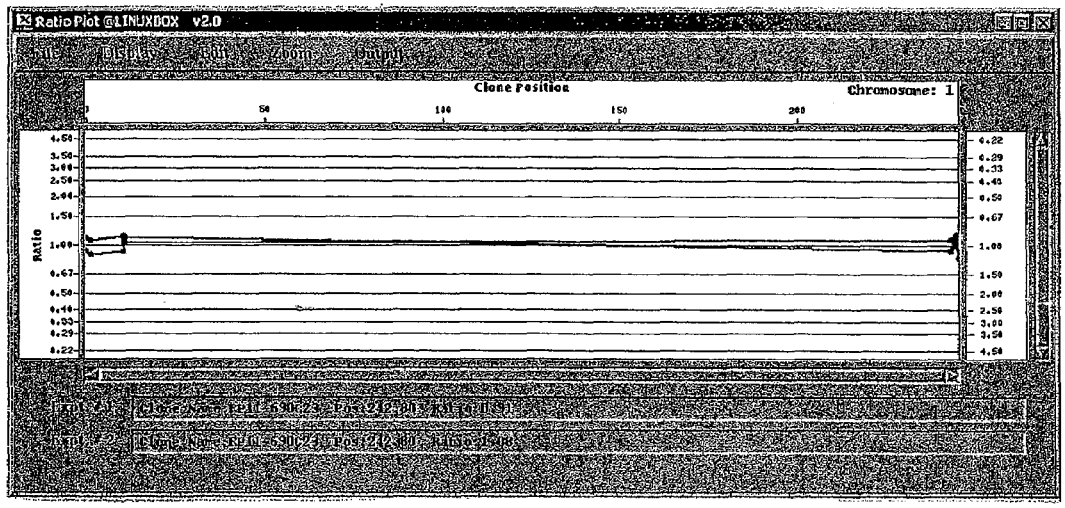
FIGS. 25A-25F shows a representation of human chromosomes 1-6 obtained by multiple label reversal ("dye swap") analysis, of a Wolf-Hirschhorn patient as the test sample, and a reference sample of a subject not known to have any chromosomal disorders, the test sample and reference sample each labeled with a fluorescent dye, and then mixed and hybridized to an array of telomere-linked markers associated with chromosomal disorders, for each chromosome. For the graph of each chromosome, only chromosomes 1-6 being shown herein, plots were obtained in which with distal short arm, the p terminus, was positioned on the left, and the distal long arm, the q terminus on the right. Plots were actual ratios generated using the SpectralWare program (Spectral Genomics, Inc., Houston, Tex.). A ratio of 1.0 would be theoretically obtained when equal quantities of binding of test sample and reference sample nucleic acids to the spot having the cloned nucleic acid are obtained as a result of comparing the amount of binding of each nucleic acid to each spot. For ratio plots, each of the two sets of dye-swap data can indicate insertion or deletion of genetic material, as shown here and in FIGS. 26A-26F. Divergence of what the software prints as open squares connected by a solid line below 1.0 on the ordinate, and what the software prints as black circles connected by a solid line below 1.0, indicates a loss of genetic material at the locus on the chromosome of the immobilized cloned nucleic acid as indicated on the abscissa. Similarly, divergence of the solid line above the 1.0 ratio line and the double line below 1.0 indicates a presence of an amplification or insertion of nucleic acid of the test sample nucleic acid, at the locus in the chromosome corresponding to the cloned nucleic acid indicated on the abscissa.
Figure 25B:
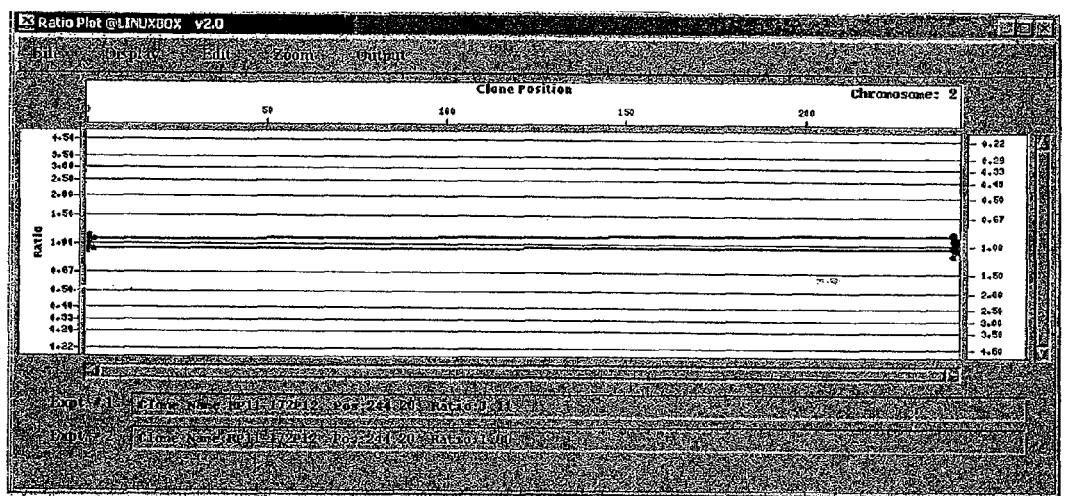
Figure 25C:
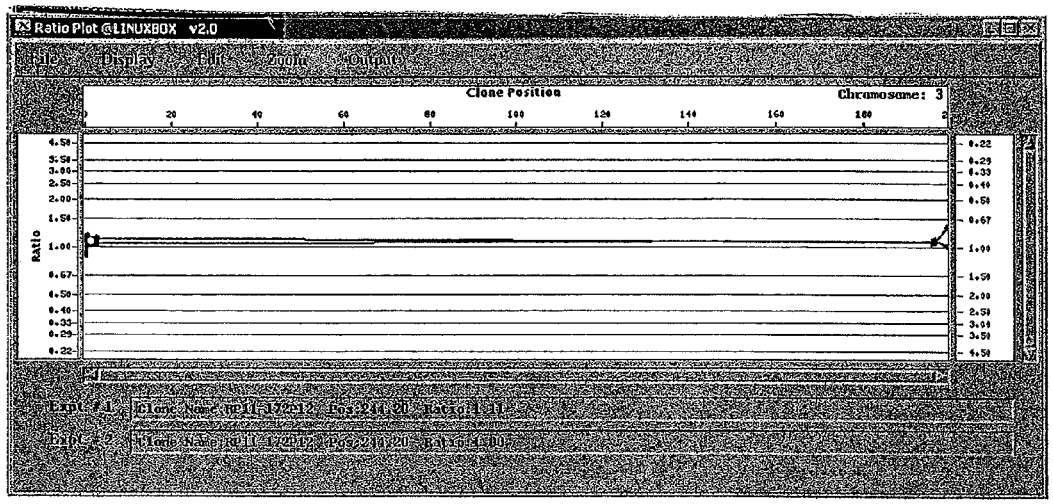
Figure 25D:
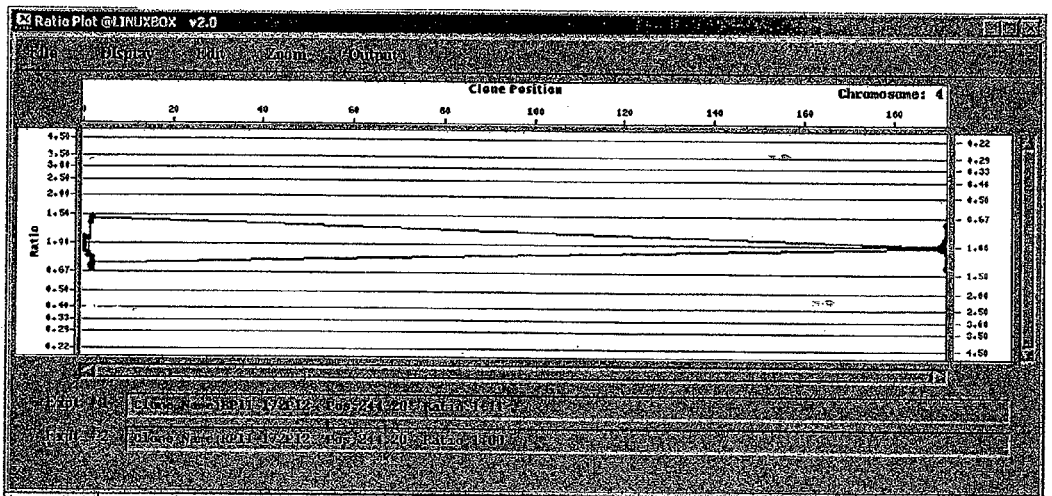
Figure 25E:
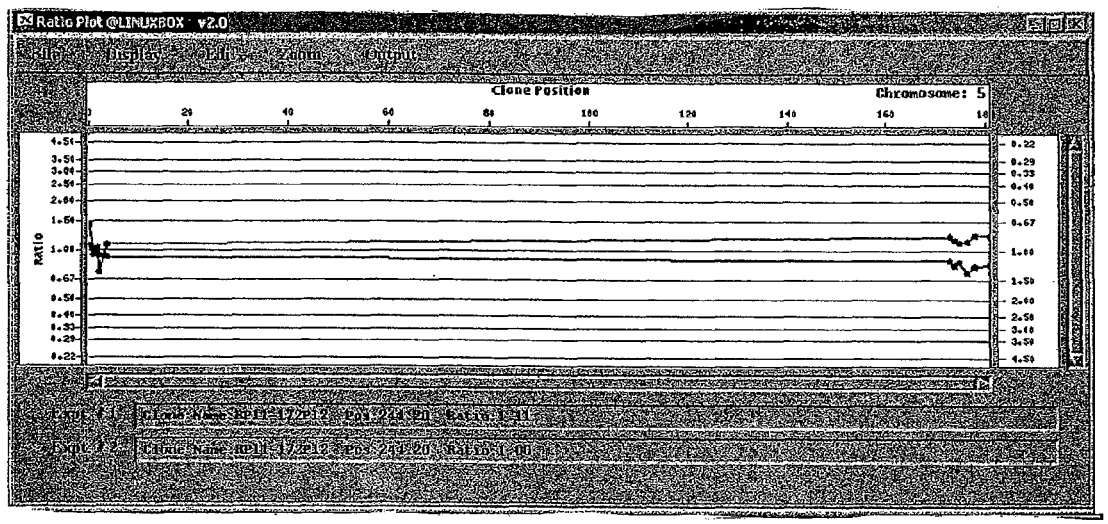
Figure 25F:
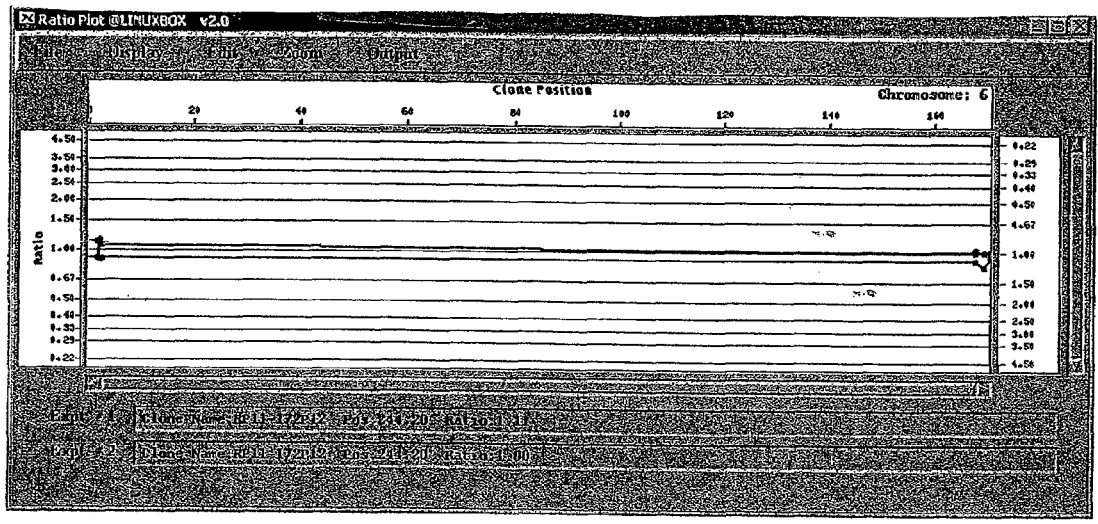
Figure 26A:
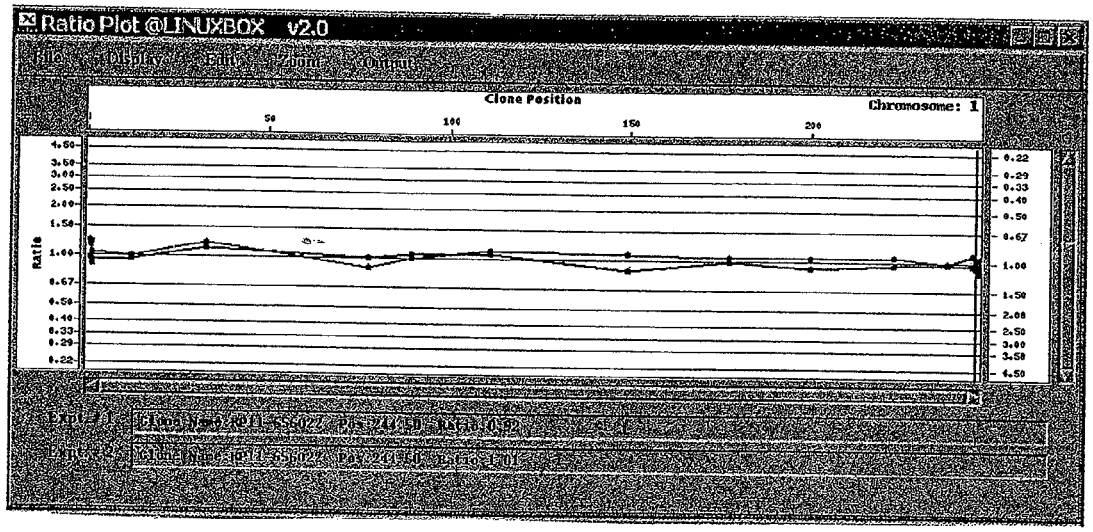
FIGS. 26A-26F are representation of human chromosomes obtained by multiple dye swap analysis, using telomere-linked cloned loci associated with chromosomal disorders, for each chromosome, and control loci that are not associated with known chromosomal disorders. Other determinations are as shown in FIGS. 25A-25F.
Figure 26B:
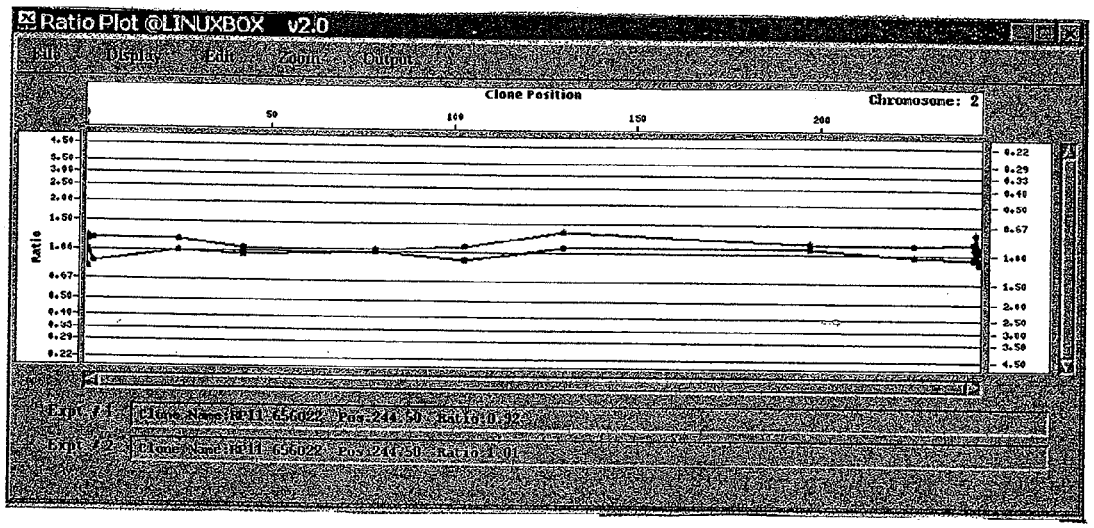
Figure 26C:
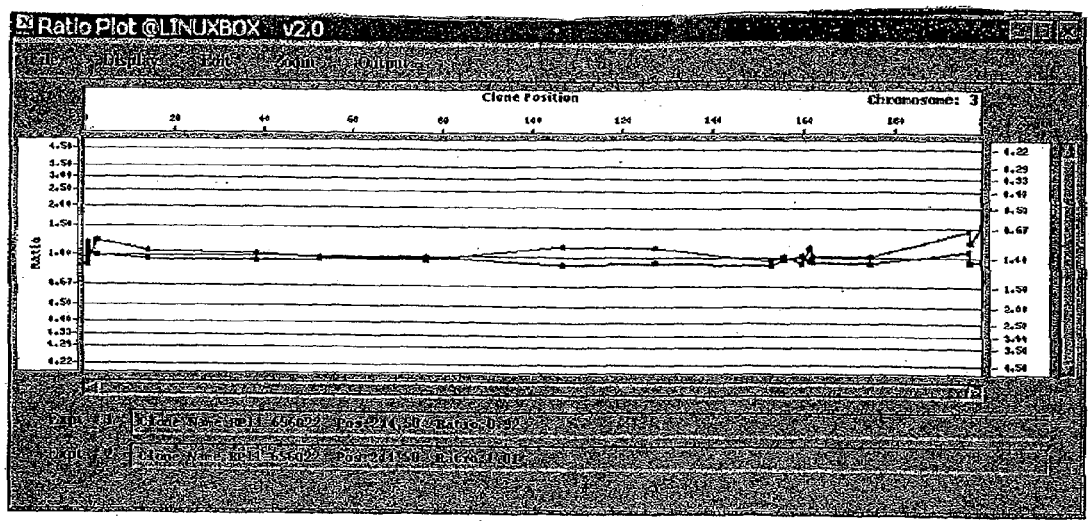
Figure 26D:
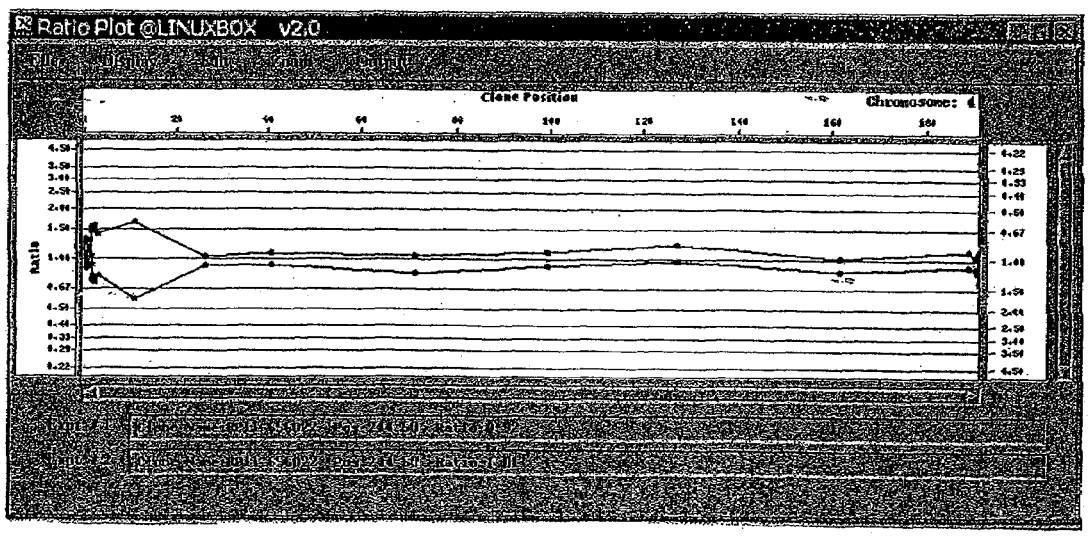
Figure 26E:
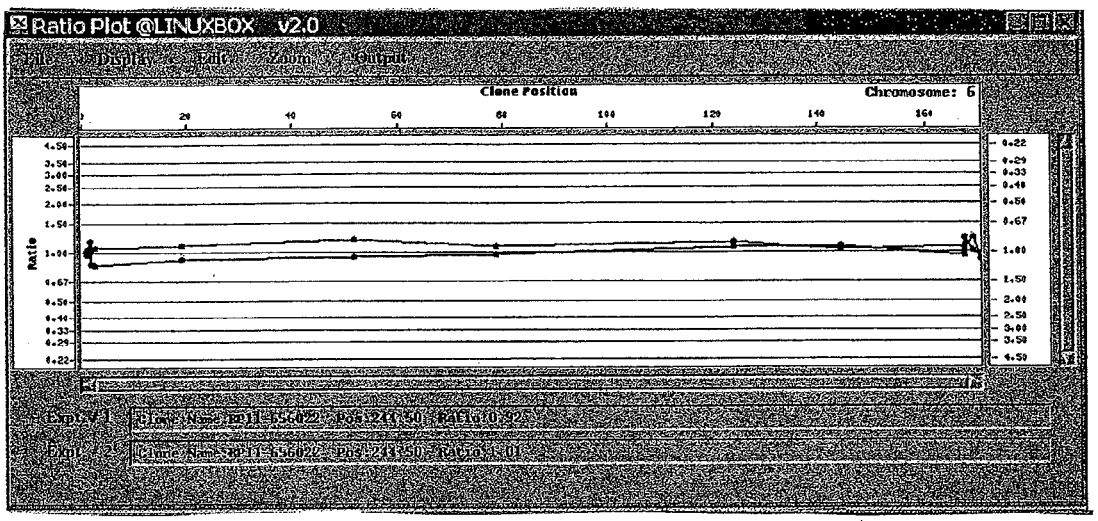
Figure 26F:
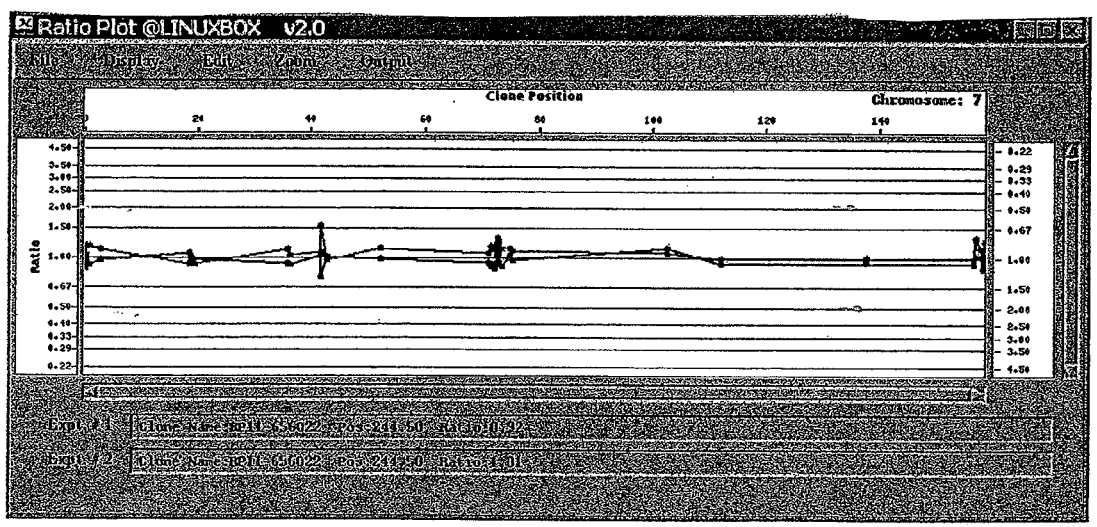

In FIG. 24 is seen an ideogram of chromsome Y. On the right side of the ideogram and in the table are listed BAC clones carrying nucleic acid sequences corresponding to portions of the Y chromosome and associated with chromosomal disorders, most of which have a phenotype affecting gonadal development (associated with locus Yq3 or Yq21) or sperm formation (Azoospermia factors 1, 2, and c, associated with locus Yq11).

Microarrays were prepared on glass slides having DNA from the listed BAC clones in FIG. 24 that contain these loci on chromosome Y, and the slides further had two copies of each of the microarrays.

Example 26

Analysis of Test Sample Nucleic Acid with Telomere-Linked Clones for a Disease FIGS. 25A-25F are representation of exemplary human chromosomes 1-6, using data obtained from dye swap analysis using the multiple single surface technique as described herein. For each chromosome indicated in the upper right hand corner of the computer generated data, the p terminus is on the left, and the q terminus on the right. A line parallel to the abscissa having a ratio of 1.0 indicates equal quantities of binding of test sample and reference sample nucleic acids to the spot having the cloned nucleic acid. Comparison of the two sets of dye-swap data at each point is used to produce the two lines. Deviation from a ratio of 1.0 for both lines is associated with insertion or deletion of genetic material.

The p terminus of chromosome 4 shown in FIGS. 25A-25F was found to have a substantial deviation from a ratio of 1.0. A typical software analysis indicates open squares connected by a double line above the 1.0 ratio for a chromosomal disorder that indicates a deletion of material. In fact the sample nucleic acid is from a patient having Wolf-Hirschhorn Syndrome.

Example 27

Analysis of Test Sample Nucleic Acid Using Telomere- and Centromere-Linked Clones Initially, only disease-associated and telomere-linked markers associated with chromosomal disorders, for each chromosome, were used to form the array, and the data are shown in FIGS. 25A-25F.

The data in FIGS. 26A-26F form a representation of human chromosomes 1-6. obtained by multiple array format dye swap analysis, using both telomere-linked cloned loci associated with chromosomal disorders, for each chromosome, and control loci that are not associated with known chromosomal disorders, including control loci that are linked to the centromeres for each of the chromosomes. The test sample is from the same patient as the data shown in Example 26.

For chromosome 4, it can be seen that the deletion is confined to the p terminus, and that the remainder of the chromosome appears to have the normal complement of sequence material compared to the normal reference nucleic acid sample.

A number of embodiments of the invention have been described. Nevertheless, it will be understood that various modifications may be made without departing from the spirit and scope of the invention. Accordingly, other embodiments are within the scope of the following claims.

What is claimed is:

1. A surface for detecting a genetic syndrome of a subject, the surface comprising a plurality of non-contiguous microarrays, wherein each microarray comprises a plurality of cloned genomic nucleic acids immobilized on the surface at discrete and known spots, and each microarray comprises a first set of spots having nucleic acids selected to detect a genetic syndrome and a second set of spots having control nucleic acids for at least part of a chromosome of the subject.

2. A combination comprising the surface according to claim 1, and a cover for at least one of the plurality of microarrays.

3. The combination according to claim 2, wherein the cover separates fluid of the at least one microarray from other microarrays in the plurality of microarrays.

4. The combination according to claim 3, wherein the surface is planar, and the cover is planar or arcuate in cross section.

5. The surface according to claim 1, wherein the surface is selected from the group consisting of a metal, silicon, a polymer plastic, paper, ceramic, quartz, gallium arsenide, a metalloid, cellulose, cellulose acetate, nitrocellulose, and a glass.

6. The surface according to claim 5, wherein the plastic is selected from the group consisting of nylon, polycarbonate, polyethylene, polystyrene, polytetrafluoroethylene, polypropylene, poly(4-methylbutene), polystyrene, latex, polymethacrylate, poly(ethylene terephthalate), rayon, polyvinylbutyrate, polyvinylidene difluoride, and combinations thereof.

7. The surface according to claim 1, wherein the cloned genomic nucleic acids of the microarray comprise nucleic acids of a plurality of chromosomes.

8. The surface according to claim 7, wherein the plurality of chromosomes comprises the genome of the subject.

9. The surface according to claim 7, wherein the plurality of chromosomes comprises autosomes.

10. The surface according to claim 7, wherein the plurality of chromosomes comprises at least one sex chromosome.

11. The surface according to claim 1, wherein the cloned genomic nucleic acids of the microarray comprise nucleic acids of a single chromosome.

12. The surface according to claim 1, wherein the microarray comprises a plurality of cloned genomic nucleic acids selected to detect a genetic syndrome and a plurality of cloned control genomic nucleic acids.

13. The surface according to claim 12, wherein the plurality of cloned nucleic acids selected to detect a genetic syndrome are located on a single chromosome.

14. The surface according to claim 12, wherein the plurality of cloned nucleic acids selected to detect a genetic syndrome are located on a plurality of chromosomes.

15. The surface according to claim 12, wherein the plurality of cloned genomic nucleic acids selected to detect a genetic syndrome and the plurality of cloned control genomic nucleic acids are distributed among a plurality of chromosomes of the subject.

16. The surface according to claim 1, wherein the microarray further contains a plurality of cloned nucleic acids selected to detect a plurality of genetic syndromes.

17. The surface according to claim 16, wherein the plurality is at least 5 genetic syndromes.

18. The surface according to claim 16, wherein the plurality is at least 40 genetic syndromes.

19. The surface according to claim 16, wherein the plurality is less than 1,000 genetic syndromes.

20. The surface according to claim 1, wherein the microarray further comprises at least one calibration spot.

21. The surface according to claim 20, wherein the calibration spot comprises a mixture of the plurality of cloned genomic control nucleic acids.

22. The surface according to claim 20, wherein the calibration spot comprises cloned genomic nucleic acids selected to detect a genetic syndrome and located on the chromosome closely linked to centromere.

23. The surface according to claim 1, wherein the surface further comprises at least one fluid barrier located between at least two of the microarrays, wherein the barrier separates a fluid above at least one of the microarrays from fluid above at least another microarray of the plurality.

24. The surface according to claim 23, wherein the barrier is selected from an elevated structure of hydrophobic composition contiguous with the surface and a hydrophobic strip printed on the surface.

25. The surface according to claim 23, wherein the elevated structure is a glass barrier.

26. The surface according to claim 21, wherein the elevated structure comprises a hydrophobic polymer.

27. The surface according to claim 21, wherein the hydrophobic strip is selected from the group of polyethylene, silicone, paraffin, and polytetrafluoroethylene.

28. A kit comprising the surface of any of claims 1-27, a container, and instructions for use.

29. The kit according to claim 28, further comprising nucleic acid of a reference subject.

30. The kit according to claim 29, further comprising a first detectable label and a second detectable label.

* * * * *